(12) United States Patent
Kuyler

(10) Patent No.: US 12,727,889 B2
(45) Date of Patent: Sep. 8, 2026

(54) REVERSIBLE COMPRESSOR-DISTRACTOR FOR BONE REALIGNMENT PROCEDURES

(71) Applicant: Treace Medical Concepts, Inc., Ponte Vedra, FL (US)

(72) Inventor: Adriaan Kuyler, Ponte Vedra, FL (US)

(73) Assignee: Treace Medical Concepts, Inc., Ponte Vedra, FL (US)

(*) Notice: Subject to any disclaimer, the term of this patent is extended or adjusted under 35 U.S.C. 154(b) by 193 days.

(21) Appl. No.: 18/467,453

(22) Filed: Sep. 14, 2023

(65) Prior Publication Data

US 2024/0081834 A1 Mar. 14, 2024

Related U.S. Application Data

(60) Provisional application No. 63/406,436, filed on Sep. 14, 2022.

(51) Int. Cl.
*A61B 17/17* (2006.01)
*A61B 17/15* (2006.01)
(Continued)

(52) U.S. Cl.
CPC ........ *A61B 17/151* (2013.01); *A61B 17/1775* (2016.11); *A61B 17/6425* (2013.01); *A61B 17/66* (2013.01); *A61B 2017/565* (2013.01)

(58) Field of Classification Search
CPC .............. A61B 17/151; A61B 17/1775; A61B 17/6425; A61B 17/66; A61B 2017/565
See application file for complete search history.

(56) References Cited

U.S. PATENT DOCUMENTS 2,251,209 A 7/1941 Stader
2,432,695 A 12/1947 Speas
(Continued)

FOREIGN PATENT DOCUMENTS

AU 2009227957 B2 7/2014
CA 2491824 A1 9/2005
(Continued)

OTHER PUBLICATIONS

Rodriguez et al., "Ilizarov method of fixation for the management of pilon and distal tibial fractures in the compromised diabetic patient: A technique guide," The Foot and Ankle Journal Online, vol. 7, No. 2, 2014, 9 pages.
(Continued)

*Primary Examiner* — Ellen C Hammond
(74) *Attorney, Agent, or Firm* — Fredrikson & Byron, P.A.

(57) ABSTRACT

A reversible compressor-distractor device may be used during a surgical procedure, such as a surgical procedure to correct a bunion deformity. In some examples, the reversible compressor-distractor is configured to be interchangeably used on right and left feet by reversing the orientation of the compressor-distractor. For example, the compressor-distractor may include a first engagement arm having at least two oppositely orientated pin-receiving holes on different sides of the engagement arm. The compressor-distractor may also include a second engagement arm having at least one pin-receiving hole. In use, the clinician can select an orientation of the compressor-distractor and engage pin-receiving holes associated with the selected orientation.

18 Claims, 19 Drawing Sheets

(51) Int. Cl.

| | |
|---|---|
| ***A61B 17/56*** | (2006.01) |
| ***A61B 17/64*** | (2006.01) |
| ***A61B 17/66*** | (2006.01) |

(56) References Cited

U.S. PATENT DOCUMENTS 3,664,022 A 5/1972 Small
4,069,824 A 1/1978 Weinstock
4,159,716 A 7/1979 Borchers
4,187,840 A 2/1980 Watanabe
4,187,841 A 2/1980 Knutson
4,335,715 A 6/1982 Kirkley
4,338,927 A 7/1982 Volkov et al.
4,349,018 A 9/1982 Chambers
4,409,973 A 10/1983 Neufeld
4,440,168 A 4/1984 Warren
4,501,268 A 2/1985 Comparetto
4,502,474 A 3/1985 Comparetto
4,509,511 A 4/1985 Neufeld
4,565,191 A 1/1986 Slocum
4,570,624 A 2/1986 Wu
4,627,425 A 12/1986 Reese
4,628,919 A 12/1986 Clyburn
4,632,102 A 12/1986 Comparetto
4,664,102 A 5/1987 Comparetto
4,708,133 A 11/1987 Comparetto
4,730,608 A 3/1988 Schlein
4,736,737 A 4/1988 Fargie et al.
4,750,481 A 6/1988 Reese
4,754,746 A 7/1988 Cox
4,757,810 A 7/1988 Reese
4,895,141 A 1/1990 Koeneman et al.
4,952,214 A 8/1990 Comparetto
4,959,066 A 9/1990 Dunn et al.
4,978,347 A 12/1990 Ilizarov
4,988,349 A 1/1991 Pennig
4,995,875 A 2/1991 Coes
5,021,056 A 6/1991 Hofmann et al.
5,035,698 A 7/1991 Comparetto
5,042,983 A 8/1991 Rayhack
5,049,149 A 9/1991 Schmidt
5,053,039 A 10/1991 Hofmann et al.
5,078,719 A 1/1992 Schreiber
5,112,334 A 5/1992 Alchermes et al.
5,147,364 A 9/1992 Comparetto
5,176,685 A 1/1993 Rayhack
5,207,676 A 5/1993 Canadell et al.
5,246,444 A 9/1993 Schreiber
5,254,119 A 10/1993 Schreiber
5,304,177 A 4/1994 Pennig
5,312,412 A 5/1994 Whipple
5,358,504 A 10/1994 Paley et al.
5,364,402 A 11/1994 Mumme et al.
5,374,271 A 12/1994 Hwang
5,413,579 A 5/1995 Tom Du Toit
5,415,663 A 5/1995 Luckman et al.
5,417,694 A 5/1995 Marik et al.
5,449,360 A 9/1995 Schreiber
5,470,335 A 11/1995 Du Toit
5,490,854 A 2/1996 Fisher et al.
5,529,075 A 6/1996 Clark
5,540,695 A 7/1996 Levy
5,578,038 A 11/1996 Slocum
5,586,564 A 12/1996 Barrett et al.
5,601,565 A 2/1997 Huebner
5,611,802 A 3/1997 Samuelson et al.
5,613,969 A 3/1997 Jenkins, Jr.
5,620,442 A 4/1997 Bailey et al.
5,620,448 A 4/1997 Puddu
D380,548 S 7/1997 Koros et al.
5,643,270 A 7/1997 Combs
5,667,510 A 9/1997 Combs
H1706 H 1/1998 Mason
5,722,978 A 3/1998 Jenkins, Jr.
5,749,875 A 5/1998 Puddu
5,779,709 A 7/1998 Harris, Jr. et al.
5,788,695 A 8/1998 Richardson
5,792,159 A 8/1998 Amin
5,803,924 A 9/1998 Oni et al.
5,810,822 A 9/1998 Mortier
D403,066 S 12/1998 Defonzo
5,843,085 A 12/1998 Graser
5,893,553 A 4/1999 Pinkous
5,911,724 A 6/1999 Wehrli
5,935,128 A 8/1999 Carter et al.
5,941,877 A 8/1999 Viegas et al.
5,951,556 A 9/1999 Faccioli et al.
D417,276 S 11/1999 Defonzo
5,980,526 A 11/1999 Johnson et al.
5,984,931 A 11/1999 Greenfield
6,007,535 A 12/1999 Rayhack et al.
6,027,504 A 2/2000 Mcguire
6,030,391 A 2/2000 Brainard et al.
6,162,223 A 12/2000 Orsak et al.
6,171,309 B1 1/2001 Huebner
6,203,545 B1 3/2001 Stoffella
D443,059 S 5/2001 Endo
6,248,109 B1 6/2001 Stoffella
6,391,031 B1 5/2002 Toomey
6,416,465 B2 7/2002 Brau
6,478,799 B1 11/2002 Williamson
6,511,481 B2 1/2003 Von Hoffmann et al.
6,547,793 B1 4/2003 Mcguire
6,676,662 B1 1/2004 Bagga et al.
6,719,773 B1 4/2004 Boucher et al.
6,743,233 B1 6/2004 Baldwin et al.
6,755,838 B2 6/2004 Trnka
6,796,986 B2 9/2004 Duffner
6,859,661 B2 2/2005 Tuke
6,964,645 B1 11/2005 Smits
7,018,383 B2 3/2006 Mcguire
7,033,361 B2 4/2006 Collazo
7,097,647 B2 8/2006 Segler
7,112,204 B2 9/2006 Justin et al.
7,153,310 B2 12/2006 Ralph et al.
7,182,766 B1 2/2007 Mogul
7,241,298 B2 7/2007 Nemec et al.
7,282,054 B2 10/2007 Steffensmeier et al.
D566,271 S 4/2008 Gao et al.
7,377,924 B2 5/2008 Raistrick et al.
7,465,303 B2 12/2008 Riccione et al.
7,540,874 B2 6/2009 Trumble et al.
D597,666 S 8/2009 George et al.
7,572,258 B2 8/2009 Stiernborg
7,578,822 B2 8/2009 Rezach et al.
7,618,424 B2 11/2009 Wilcox et al.
7,641,660 B2 1/2010 Lakin et al.
D610,257 S 2/2010 Horton
7,686,811 B2 3/2010 Byrd et al.
7,691,108 B2 4/2010 Lavallee
7,763,026 B2 7/2010 Egger et al.
D629,900 S 12/2010 Fisher
7,967,823 B2 6/2011 Ammann et al.
7,972,338 B2 7/2011 O'Brien
D646,389 S 10/2011 Claypool et al.
8,057,478 B2 11/2011 Kuczynski et al.
8,062,301 B2 11/2011 Ammann et al.
D651,315 S 12/2011 Bertoni et al.
D651,316 S 12/2011 May et al.
8,080,010 B2 12/2011 Schulz et al.
8,080,045 B2 12/2011 Wotton
8,083,746 B2 12/2011 Novak
8,123,753 B2 2/2012 Poncet
D656,610 S 3/2012 Kleiner
8,137,406 B2 3/2012 Novak et al.
8,147,530 B2 4/2012 Strnad et al.
8,167,918 B2 5/2012 Strnad et al.
8,172,848 B2 5/2012 Tomko et al.
8,192,441 B2 6/2012 Collazo
8,197,487 B2 6/2012 Poncet et al.
8,231,623 B1 7/2012 Jordan
8,231,663 B2 7/2012 Kay et al.
8,236,000 B2 8/2012 Ammann et al.
8,246,561 B1 8/2012 Agee et al.

(56) References Cited

U.S. PATENT DOCUMENTS

D666,721 S 9/2012 Wright et al.
8,262,664 B2 9/2012 Justin et al.
8,277,459 B2 10/2012 Sand et al.
8,282,644 B2 10/2012 Edwards
8,282,645 B2 10/2012 Lawrence et al.
8,292,966 B2 10/2012 Morton
8,303,596 B2 11/2012 Plaky et al.
8,313,492 B2 11/2012 Wong et al.
8,323,289 B2 12/2012 Re
8,337,503 B2 12/2012 Lian
8,343,159 B2 1/2013 Bennett
8,377,105 B2 2/2013 Bscher
D679,395 S 4/2013 Wright et al.
8,409,209 B2 4/2013 Ammann et al.
8,435,246 B2 5/2013 Fisher et al.
8,475,462 B2 7/2013 Thomas et al.
8,496,662 B2 7/2013 Novak et al.
8,518,045 B2 8/2013 Szanto
8,523,870 B2 9/2013 Green, II et al.
8,529,571 B2 9/2013 Horan et al.
8,540,777 B2 9/2013 Ammann et al.
8,545,508 B2 10/2013 Collazo
D694,884 S 12/2013 Mooradian et al.
D695,402 S 12/2013 Dacosta et al.
8,652,142 B2 2/2014 Geissler
8,657,820 B2 2/2014 Kubiak et al.
D701,303 S 3/2014 Cook
8,672,945 B2 3/2014 Lavallee et al.
8,696,716 B2 4/2014 Kartalian et al.
8,702,715 B2 4/2014 Ammann et al.
D705,929 S 5/2014 Frey
8,715,363 B2 5/2014 Ratron et al.
8,728,084 B2 5/2014 Berelsman et al.
8,758,354 B2 6/2014 Habegger et al.
8,764,760 B2 7/2014 Metzger et al.
8,764,763 B2 7/2014 Wong et al.
8,771,279 B2 7/2014 Philippon et al.
8,777,948 B2 7/2014 Bernsteiner
8,784,427 B2 7/2014 Fallin et al.
8,784,457 B2 7/2014 Graham
8,795,286 B2 8/2014 Sand et al.
8,801,727 B2 8/2014 Chan et al.
8,808,303 B2 8/2014 Stemniski et al.
8,828,012 B2 9/2014 May et al.
8,858,602 B2 10/2014 Weiner et al.
8,882,778 B2 11/2014 Ranft
8,882,816 B2 11/2014 Kartalian et al.
8,888,785 B2 11/2014 Ammann et al.
D720,456 S 12/2014 Dacosta et al.
8,900,247 B2 12/2014 Tseng et al.
8,906,026 B2 12/2014 Ammann et al.
8,945,132 B2 2/2015 Play et al.
8,998,903 B2 4/2015 Price et al.
8,998,904 B2 4/2015 Zeetser et al.
9,023,052 B2 5/2015 Lietz et al.
9,044,250 B2 6/2015 Olsen et al.
9,060,822 B2 6/2015 Wright et al.
9,078,710 B2 7/2015 Thoren et al.
9,089,376 B2 7/2015 Medoff et al.
9,101,421 B2 8/2015 Blacklidge
9,107,715 B2 8/2015 Blitz et al.
9,113,920 B2 8/2015 Ammann et al.
D740,424 S 10/2015 Dacosta et al.
D747,479 S 1/2016 Knight
D765,844 S 9/2016 Dacosta
D766,434 S 9/2016 Dacosta
D766,437 S 9/2016 Dacosta
D766,438 S 9/2016 Dacosta
D766,439 S 9/2016 Dacosta
9,452,057 B2 9/2016 Dacosta et al.
9,522,023 B2 12/2016 Haddad et al.
9,592,084 B2 3/2017 Grant
9,622,805 B2 4/2017 Santrock et al.
D796,671 S 9/2017 Khouri
9,750,538 B2 9/2017 Soffiatti et al.
9,770,272 B2 9/2017 Thoren et al.
9,785,747 B2 10/2017 Geebelen
9,924,969 B2 3/2018 Triplett et al.
9,936,994 B2 4/2018 Smith et al.
9,980,760 B2 5/2018 Dacosta et al.
10,028,750 B2 7/2018 Rose
10,064,631 B2 9/2018 Dacosta et al.
10,159,499 B2 12/2018 Dacosta et al.
10,292,713 B2 5/2019 Fallin et al.
10,327,829 B2 6/2019 Dacosta et al.
10,376,268 B2 8/2019 Fallin et al.
D865,173 S 10/2019 Hartson et al.
10,470,779 B2 11/2019 Fallin et al.
10,524,808 B1 1/2020 Hissong et al.
10,779,867 B2 9/2020 Penzimer et al.
D904,609 S 12/2020 Dacosta et al.
10,939,939 B1 3/2021 Gil et al.
D915,588 S 4/2021 Dacosta et al.
D931,449 S 9/2021 Tanabe
D943,741 S 2/2022 Hartson et al.
D945,610 S 3/2022 Wilson et al.
11,304,705 B2 4/2022 Fallin et al.
D956,227 S 6/2022 Dacosta et al.
11,889,998 B1 * 2/2024 Treace ................ A61B 17/685
12,279,794 B2 * 4/2025 Treace ................ A61B 17/025
2002/0099381 A1 7/2002 Maroney
2002/0107519 A1 8/2002 Dixon et al.
2002/0165552 A1 11/2002 Duffner
2002/0198531 A1 12/2002 Millard et al.
2004/0010259 A1 1/2004 Keller et al.
2004/0039394 A1 2/2004 Conti et al.
2004/0097946 A1 5/2004 Dietzel et al.
2004/0138669 A1 7/2004 Horn
2005/0004676 A1 1/2005 Schon et al.
2005/0021040 A1 1/2005 Bertagnoli
2005/0059978 A1 3/2005 Sherry et al.
2005/0070909 A1 3/2005 Egger et al.
2005/0075641 A1 4/2005 Singhatat et al.
2005/0101961 A1 5/2005 Huebner et al.
2005/0149042 A1 7/2005 Metzger
2005/0203509 A1 9/2005 Chinnaian et al.
2005/0228389 A1 10/2005 Stiernborg
2005/0251147 A1 11/2005 Novak
2005/0267482 A1 12/2005 Hyde
2005/0273112 A1 12/2005 Mcnamara
2006/0122597 A1 6/2006 Jones et al.
2006/0129163 A1 6/2006 Mcguire
2006/0206044 A1 9/2006 Simon
2006/0217733 A1 9/2006 Plassky et al.
2006/0229604 A1 10/2006 Olsen et al.
2006/0229621 A1 10/2006 Cadmus
2006/0235383 A1 10/2006 Hollawell
2006/0241607 A1 10/2006 Myerson et al.
2006/0241608 A1 10/2006 Myerson et al.
2006/0247649 A1 11/2006 Rezach et al.
2006/0264961 A1 11/2006 Murray-Brown
2007/0010818 A1 1/2007 Stone et al.
2007/0055233 A1 3/2007 Brinker
2007/0123857 A1 5/2007 Deffenbaugh et al.
2007/0233138 A1 10/2007 Figueroa et al.
2007/0265634 A1 11/2007 Weinstein
2007/0276383 A1 11/2007 Rayhack
2008/0009863 A1 1/2008 Bond et al.
2008/0015603 A1 1/2008 Collazo
2008/0039850 A1 2/2008 Rowley et al.
2008/0091197 A1 4/2008 Coughlin
2008/0140081 A1 6/2008 Heavener et al.
2008/0147073 A1 6/2008 Ammann et al.
2008/0172054 A1 7/2008 Claypool et al.
2008/0195215 A1 8/2008 Morton
2008/0208252 A1 8/2008 Holmes
2008/0262500 A1 10/2008 Collazo
2008/0269908 A1 10/2008 Warburton
2008/0288004 A1 11/2008 Schendel
2009/0036893 A1 2/2009 Kartalian et al.
2009/0036931 A1 2/2009 Pech et al.
2009/0054899 A1 2/2009 Ammann et al.
2009/0093849 A1 4/2009 Grabowski
2009/0105767 A1 4/2009 Reiley

(56) References Cited

U.S. PATENT DOCUMENTS

2009/0118733 A1 5/2009 Orsak et al.
2009/0187189 A1 7/2009 Mirza et al.
2009/0198244 A1 8/2009 Leibel
2009/0198279 A1 8/2009 Zhang et al.
2009/0216089 A1 8/2009 Davidson
2009/0222047 A1 9/2009 Graham
2009/0254092 A1 10/2009 Albiol Llorach
2009/0254126 A1 10/2009 Orbay et al.
2009/0287309 A1 11/2009 Walch et al.
2010/0030283 A1 2/2010 King et al.
2010/0069910 A1 3/2010 Hasselman
2010/0121334 A1 5/2010 Couture et al.
2010/0130981 A1 5/2010 Richards
2010/0152782 A1 6/2010 Stone et al.
2010/0168799 A1 7/2010 Schumer
2010/0185245 A1 7/2010 Paul et al.
2010/0249779 A1 9/2010 Hotchkiss et al.
2010/0256687 A1 10/2010 Neufeld et al.
2010/0318088 A1 12/2010 Warne et al.
2010/0324556 A1 12/2010 Tyber et al.
2011/0009865 A1 1/2011 Orfaly
2011/0093084 A1 4/2011 Morton
2011/0118739 A1 5/2011 Tyber et al.
2011/0172662 A1 7/2011 Keilen
2011/0178524 A1 7/2011 Lawrence et al.
2011/0245835 A1 10/2011 Dodds et al.
2011/0288550 A1 11/2011 Orbay et al.
2011/0301648 A1 12/2011 Lofthouse et al.
2012/0016426 A1 1/2012 Robinson
2012/0065689 A1 3/2012 Prasad et al.
2012/0078258 A1 3/2012 Lo et al.
2012/0123420 A1 5/2012 Honiball
2012/0123484 A1 5/2012 Lietz et al.
2012/0130376 A1 5/2012 Loring et al.
2012/0130382 A1 5/2012 Lannotti et al.
2012/0130383 A1 5/2012 Budoff
2012/0184961 A1 7/2012 Johannaber
2012/0185056 A1 7/2012 Warburton
2012/0191199 A1 7/2012 Raemisch
2012/0239045 A1 9/2012 Li
2012/0253350 A1 10/2012 Anthony et al.
2012/0265301 A1 10/2012 Demers et al.
2012/0277745 A1 11/2012 Lizee
2012/0303033 A1 11/2012 Weiner et al.
2012/0330135 A1 12/2012 Millahn et al.
2013/0012949 A1 1/2013 Fallin et al.
2013/0035694 A1 2/2013 Grimm et al.
2013/0085499 A1 4/2013 Lian
2013/0085502 A1 4/2013 Harrold
2013/0096563 A1 4/2013 Meade et al.
2013/0131821 A1 5/2013 Cachia
2013/0150900 A1 6/2013 Haddad et al.
2013/0150903 A1 6/2013 Vincent
2013/0158556 A1 6/2013 Jones et al.
2013/0165936 A1 6/2013 Myers
2013/0165938 A1 6/2013 Chow et al.
2013/0172942 A1 7/2013 Wright et al.
2013/0184714 A1 7/2013 Kaneyama et al.
2013/0190765 A1 7/2013 Harris et al.
2013/0190766 A1 7/2013 Harris et al.
2013/0204259 A1 8/2013 Zajac
2013/0204261 A1* 8/2013 Eschle ................ C04B 35/6455 606/88
2013/0226248 A1 8/2013 Hatch et al.
2013/0226252 A1 8/2013 Mayer
2013/0231668 A1 9/2013 Olsen et al.
2013/0237987 A1 9/2013 Graham
2013/0237989 A1 9/2013 Bonutti
2013/0267956 A1 10/2013 Terrill et al.
2013/0310836 A1 11/2013 Raub et al.
2013/0325019 A1 12/2013 Thomas et al.
2013/0325076 A1 12/2013 Palmer et al.
2013/0331845 A1 12/2013 Horan et al.
2013/0338785 A1 12/2013 Wong
2014/0005672 A1 1/2014 Edwards et al.
2014/0025127 A1 1/2014 Richter
2014/0039501 A1 2/2014 Schickendantz et al.
2014/0039561 A1 2/2014 Weiner et al.
2014/0046387 A1 2/2014 Waizenegger
2014/0074099 A1 3/2014 Vigneron et al.
2014/0074101 A1 3/2014 Collazo
2014/0094861 A1 4/2014 Fallin
2014/0094924 A1 4/2014 Hacking et al.
2014/0135775 A1 5/2014 Maxson et al.
2014/0163563 A1 6/2014 Reynolds et al.
2014/0171953 A1 6/2014 Gonzalvez et al.
2014/0180342 A1 6/2014 Lowery et al.
2014/0188139 A1 7/2014 Fallin et al.
2014/0194884 A1 7/2014 Martin et al.
2014/0194999 A1 7/2014 Orbay et al.
2014/0207144 A1 7/2014 Lee et al.
2014/0228899 A1 8/2014 Thoren et al.
2014/0243825 A1 8/2014 Yapp et al.
2014/0249537 A1 9/2014 Wong et al.
2014/0257308 A1 9/2014 Johannaber
2014/0257509 A1 9/2014 Dacosta et al.
2014/0276815 A1 9/2014 Riccione
2014/0276853 A1 9/2014 Long et al.
2014/0277176 A1 9/2014 Buchanan et al.
2014/0277214 A1 9/2014 Helenbolt et al.
2014/0288562 A1 9/2014 Von Zabern et al.
2014/0296995 A1 10/2014 Reiley et al.
2014/0303621 A1 10/2014 Gerold et al.
2014/0336658 A1 11/2014 Luna et al.
2014/0343555 A1 11/2014 Russi et al.
2014/0350561 A1 11/2014 Dacosta et al.
2015/0032168 A1 1/2015 Orsak et al.
2015/0045801 A1 2/2015 Axelson, Jr. et al.
2015/0045839 A1 2/2015 Dacosta et al.
2015/0051650 A1 2/2015 Verstreken et al.
2015/0057667 A1 2/2015 Ammann et al.
2015/0066088 A1 3/2015 Brinkman et al.
2015/0066094 A1 3/2015 Anderson et al.
2015/0112446 A1 4/2015 Melamed et al.
2015/0119944 A1 4/2015 Geldwert
2015/0142064 A1 5/2015 Perez et al.
2015/0150608 A1 6/2015 Sammarco
2015/0182273 A1 7/2015 Stemniski et al.
2015/0223851 A1 8/2015 Hill et al.
2015/0230843 A1 8/2015 Palmer et al.
2015/0245858 A1 9/2015 Weiner et al.
2016/0015426 A1 1/2016 Dayton
2016/0022315 A1 1/2016 Soffiatti et al.
2016/0135858 A1 5/2016 Dacosta et al.
2016/0151165 A1 6/2016 Fallin et al.
2016/0175089 A1 6/2016 Fallin et al.
2016/0192950 A1* 7/2016 Dayton ................. A61B 17/15 606/87
2016/0192970 A1 7/2016 Dayton et al.
2016/0199076 A1 7/2016 Fallin et al.
2016/0213384 A1 7/2016 Fallin et al.
2016/0235414 A1 8/2016 Hatch et al.
2016/0242791 A1 8/2016 Fallin et al.
2016/0256204 A1 9/2016 Patel et al.
2016/0270800 A1 9/2016 Sanders
2016/0324532 A1 11/2016 Montoya et al.
2016/0354127 A1 12/2016 Lundquist et al.
2017/0014143 A1 1/2017 Dayton et al.
2017/0042598 A1 2/2017 Santrock et al.
2017/0042599 A1 2/2017 Bays et al.
2017/0079669 A1 3/2017 Bays et al.
2017/0135706 A1 5/2017 Frey et al.
2017/0143511 A1 5/2017 Cachia
2017/0164989 A1 6/2017 Weiner et al.
2017/0290614 A1 10/2017 Weiner et al.
2018/0021145 A1 1/2018 Seavey et al.
2018/0132868 A1 5/2018 Dacosta et al.
2018/0235765 A1 8/2018 Welker et al.
2018/0344334 A1 12/2018 Kim et al.
2019/0099189 A1 4/2019 Fallin et al.
2019/0336140 A1 11/2019 Dacosta et al.
2019/0350598 A1 11/2019 Jacobson
2020/0015856 A1 1/2020 Treace et al.
2020/0060721 A1 2/2020 Cermak

(56) References Cited

U.S. PATENT DOCUMENTS

2020/0253641 A1* 8/2020 Treace ................. A61B 17/025
2021/0236180 A1 8/2021 Decarbo et al.
2021/0244443 A1 8/2021 Coyne et al.
2021/0361330 A1 11/2021 Mcaleer et al.
2022/0117611 A1 4/2022 Milella, Jr. et al.
2022/0211387 A1 7/2022 Perler et al.
2022/0257267 A1 8/2022 Decarbo et al.
2022/0323085 A1 10/2022 Hales et al.
2022/0370082 A1 11/2022 Kuyler et al.
2023/0043129 A1 2/2023 Mcaleer et al.
2023/0200855 A1* 6/2023 Treace ............... A61B 17/6425 606/57
2023/0218318 A1* 7/2023 Treace ............... A61B 17/1775 606/86 R
2023/0263536 A1* 8/2023 Kuyler ................... A61B 17/66 606/57
2023/0371965 A1* 11/2023 Lebrija ............. A61B 17/1739

FOREIGN PATENT DOCUMENTS

CA 2854997 A1 5/2013
CH 695846 A5 9/2006
CN 2930668 Y 8/2007
CN 201558162 U 8/2010
CN 201572172 U 9/2010
CN 201586060 U 9/2010
CN 201912210 U 8/2011
CN 101237835 B 11/2012
CN 202801773 U 3/2013
CN 103462675 A 12/2013
CN 103505276 A 1/2014
CN 203458450 U 3/2014
CN 102860860 B 5/2014
CN 203576647 U 5/2014
CN 104490460 A 4/2015
CN 104510523 A 4/2015
CN 104523327 A 4/2015
CN 104546102 A 4/2015
CN 204379413 U 6/2015
CN 204410951 U 6/2015
CN 204428143 U 7/2015
CN 204428144 U 7/2015
CN 204428145 U 7/2015
CN 204446081 U 7/2015
DE 202006010241 U1 3/2007
DE 102007053058 B3 4/2009
EP 685206 B1 9/2000
EP 1508316 B1 5/2007
EP 1897509 B1 7/2009
EP 2124772 A1 12/2009
EP 2124832 B1 8/2012
EP 2632349 A1 9/2013
EP 2665428 A1 11/2013
EP 2742878 A1 6/2014
EP 2750617 A1 7/2014
EP 2849684 A1 3/2015
EP 2932925 A1 10/2015
EP 2624764 B1 12/2015
EP 3023068 A2 5/2016
FR 2362616 A1 3/1978
FR 2764183 B1 11/1999
FR 2953120 B1 1/2012
FR 3030221 A1 6/2016
GB 2154143 A 9/1985
GB 2154144 A 9/1985
GB 2334214 B 1/2003
IN 200903719 P1 4/2010
IN 200904479 P2 5/2010
IN 2004/KOLNP/2013 P2 1/2013
IN 140/DELNP/2012 P1 2/2013
JP 63005739 A 1/1988
JP 2004174265 A 6/2004
JP 2006158972 A 6/2006
JP 4134243 B2 8/2008
JP 4162380 B2 10/2008
JP 2011092405 A 5/2011
JP 2011523889 A 8/2011
JP 4796943 B2 10/2011
JP 5466647 B2 4/2014
JP 2014511207 A 5/2014
JP 2014521384 A 8/2014
JP 5628875 B2 11/2014
JP 2018525111 A 9/2018
JP 2018528008 A 9/2018
KR 100904142 B1 6/2009
MD 756 B1 7/1997
RU 2098036 C1 12/1997
RU 2195892 C2 1/2003
RU 2320287 C1 3/2008
RU 2321366 C2 4/2008
RU 2321369 C1 4/2008
RU 2346663 C2 2/2009
RU 2412662 C1 2/2011
SU 1333328 A2 8/1987
WO 0166022 A1 9/2001
WO 03075775 A1 9/2003
WO 2004089227 A2 10/2004
WO 2005009209 A2 2/2005
WO 2005122923 A1 12/2005
WO 2008051064 A1 5/2008
WO 2009029798 A1 3/2009
WO 2009032101 A2 3/2009
WO 2011037885 A1 3/2011
WO 2012029008 A1 3/2012
WO 2013090392 A1 6/2013
WO 2013134387 A1 9/2013
WO 2013169475 A1 11/2013
WO 2014020561 A1 2/2014
WO 2014022055 A1 2/2014
WO 2014035991 A1 3/2014
WO 2014085882 A1 6/2014
WO 2014147099 A1 9/2014
WO 2014152219 A2 9/2014
WO 2014152535 A1 9/2014
WO 2014177783 A1 11/2014
WO 2014200017 A1 12/2014
WO 2015094409 A1 6/2015
WO 2015105880 A1 7/2015
WO 2015127515 A2 9/2015
WO 2016134160 A1 8/2016
WO 2017134486 A1 8/2017

OTHER PUBLICATIONS

Rx-Fix Mini Rail External Fixator, Wright Medical Technology, Brochure, Aug. 15, 2014, 2 pages.

Saltzman et al., “Prospective Controlled Trial of STAR Total Ankle Replacement Versus Ankle Fusion: Initial Results,” Foot & Ankle International, vol. 30, No. 7, Jul. 2009, pp. 579-596.

Sammarco, “Surgical Strategies: Mau Osteotomy for Correction of Moderate and Severe Hallux Valgus Deformity,” Foot & Ankle International, vol. 28, No. 7, Jul. 2007, pp. 857-864.

Sandhu et al., “Digital Arthrodesis With a One-Piece Memory Nitinol Intramedullary Fixation Device: A Retrospective Review,” Foot and Ankle Specialist, vol. 6, No. 5, Oct. 2013, pp. 364-366.

Santrock et al., “Hallux Valgus Deformity and Treatment: A Three-Dimensional Approach: Lapiplasty,” Foot & Ankle Clinics, vol. 23, No. 2, 2018, pp. 281-295.

Scanlan et al. “Technique Tip: Subtalar Joint Fusion Using a Parallel Guide and Double Screw Fixation,” The Journal of Foot and Ankle Surgery, vol. 49, Issue 3, May-Jun. 2010, pp. 305-309, (Abstract Only).

Schon et al., “Cuneiform-Metatarsal Arthrodesis for Hallux Valgus,” The Foot and Ankle, Second Edition, Chapter 8, 2002, pp. 99-117.

Scranton Jr. et al., “Anatomic Variations in the First Ray: Part I. Anatomic Aspects Related to Bunion Surgery,” Clinical Orthopaedics and Related Research, vol. 151, Sep. 1980, pp. 244-255.

Shima et al., “Operative Treatment for Hallux Valgus With Moderate to Severe Metatarsus Adductus,” Foot & Ankle International, vol. 40, No. 6, 2019, pp. 641-647.

(56) References Cited

OTHER PUBLICATIONS

Shurnas et al., "Proximal Metatarsal Opening Wedge Osteotomy," Operative Techniques in Foot and Ankle Surgery, Section I, Chapter 13, 2011, pp. 73-78.
Siddiqui et al. "Fixation Of Metatarsal Fracture With Bone Plate In A Dromedary Heifer," Open Veterinary Journal, vol. 3, No. 1, 2013, pp. 17-20.
Sidekick Stealth Rearfoot Fixator, Wright Medical Technology, Surgical Technique, Dec. 2, 2013, 20 pages.
Simons et al., "Short-Term Clinical Outcome of Hemiarthroplasty Versus Arthrodesis for End-Stage Hallux Rigidus," The Journal of Foot & Ankle Surgery, vol. 54, 2015, pp. 848-851.
Simpson et al., "Computer-Assisted Distraction Ostegogenesis By Ilizarov's Method," International Journal of Medical Robots and Computer Assisted Surgery, vol. 4, No. 4, Dec. 2008, pp. 310-320, (Abstract Only).
Small Bone External Fixation System, Acumed, Surgical Technique, Effective date Sep. 2014, 8 pages.
Smith et al., "Intraoperative Multiplanar Alignment System to Guide Triplanar Correction of Hallux Valgus Deformity," Techniques in Foot & Ankle Surgery, 2017, 8 pages.
Smith et al., "Opening Wedge Osteotomies for Correction of Hallux Valgus: A Review of Wedge Plate Fixation," Foot and Ankle Specialist, vol. 2, No. 6, Dec. 2009, pp. 277-282.
Smith et al., "Understanding Frontal Plane Correction in Hallux Valgus Repair," Clinics in Podiatric Medicine and Surgery, vol. 35, 2018, pp. 27-36.
Sokoloff, "Lapidus Procedure," Textbook of Bunion Surgery, Chapter 15, 1981, pp. 277-287.
Stableloc External Fixation System, Acumed, Product Overview, Effective date Sep. 2015, 4 pages.
Stahl et al., "Derotation Of Post-Traumatic Femoral Deformities By Closed Intramedullary Sawing," Injury, vol. 37, No. 2, Feb. 2006, pp. 145-151, (Abstract Only).
Stamatis et al., "Mini Locking Plate as Medial Buttress for Oblique Osteotomy for Hallux Valgus," Foot & Ankle International, vol. 31, No. 10, Oct. 2010, pp. 920-922.
Talbot et al., "Assessing Sesamoid Subluxation: How Good is the AP Radiograph?," Foot and Ankle International, vol. 19, No. 8, Aug. 1998, pp. 547-554.
TempFix Spanning the Ankle Joint Half Pin and Transfixing Pin Techniques, Biomet Orthopedics, Surgical Technique, 2012, 16 pages.
Toth et al., "The Effect of First Ray Shortening in the Development of Metatarsalgia in the Second Through Fourth Rays After Metatarsal Osteotomy," Foot & Ankle International, vol. 28, No. 1, Jan. 2007, pp. 61-63.
Tricot et al., "3D-corrective osteotomy using surgical guides for posttraumatic distal humeral deformity," Acta Orthopaedica Belgica, vol. 78, No. 4, 2012, pp. 538-542.
Use for BME Speed Nitinol Staple Fixation for the Lapidus Procedure, "date unknown, 1 page."
Vaida et al., "Effect on Foot Width With Triplanar Tarsometatarsal Arthrodesis for Hallux Valgus," Foot & Ankle Orthopaedics, vol. 5, No. 3, 2020, pp. 1-5.
Vitek et al., "Die Behandlung des Hallux rigidus mit Cheilektomie und Akin-Moberg-Osteotomie unter Verwendung einer neuen Schnittlehre und eines neuen Schraubensystems," Orthopadische Praxis, vol. 44, Nov. 2008, pp. 563-566, including English Abstract on p. 564.
Vitek, "Neue Techniken in der Fuchirurgie Das V-tek-System," ABW Wissenschaftsverlag GmbH, 2009, 11 pages, including English Abstract.
Walker et al., "The Role of First Ray Insufficiency in the Development of Metatarsalgia," Foot and Ankle Clinics, vol. 24, No. 4, Dec. 2019, published online: Sep. 5, 2019, pp. 641-648.
Weber et al., "A Simple System For Navigation Of Bone Alignment Osteotomies Of The Tibia," International Congress Series, vol. 1268, Jan. 2004, pp. 608-613, (Abstract Only).
Weber et al., "Use of the First Ray Splay Test to Assess Transverse Plane Instability Before First Metatarsocuneiform Fusion," The Journal of Foot and Ankle Surgery, vol. 45, No. 4, Jul./Aug. 2006, pp. 278-282.
Weigelt et al., "Risk Factors for Nonunion After First Metatarsophalangeal Joint Arthrodesis With a Dorsal Locking Plate and Compression Screw Construct: Correction of Hallux Valgus Is Key," The Journal of Foot & Ankle Surgery, vol. 60, No. 6, Nov./Dec. 2021, pp. 1179-1183.
Weil et al., "Anatomic Plantar Plate Repair Using the Weil Metatarsal Osteotomy Approach," Foot & Ankle Specialist, vol. 4, No. 3, 2011, pp. 145-150.
Wendl et al., "Navigation in der Knieendoprothetik," OP-Journal, vol. 17, 2002, pp. 22-27, including English Abstract.
Whipple et al., "Zimmer Herbert Whipple Bone Screw System: Surgical Techniques for Fixation of Scaphoid and Other Small Bone Fractures," Zimmer, 2003, 59 pages.
Wienke et al., "Bone Stimulation For Nonunions: What the Evidence Reveals," Podiatry Today, vol. 24, No. 9, Sep. 2011, pp. 52-57.
Williams et al., "Metatarsus adductus: Development of a non-surgical treatment pathway," Journal of Paediatrics and Child Health, vol. 49, 2013, pp. E428-E433.
Wukich et al., "Hypermobility of the First Tarsometatarsal Joint," Foot and Ankle Clinics, vol. 10, No. 1, Mar. 2005, pp. 157-166.
Yakacki et al. "Compression Forces of Internal and External Ankle Fixation Devices with Simulated Bone Resorption," Foot and Ankle International, vol. 31, No. 1, Jan. 2010, pp. 76-85, (Abstract Only).
Yasuda et al., "Proximal Supination Osteotomy of the First Metatarsal for Hallux Valgus," Foot and Ankle International, vol. 36, No. 6, Jun. 2015, pp. 696-704.
Dobbe et al. "Patient-Tailored Plate For Bone Fixation And Accurate 3D Positioning In Corrective Osteotomy," Medical and Biological Engineering and Computing, vol. 51, No. 1-2, Feb. 2013, pp. 19-27, (Abstract Only).
Doty et al., "Hallux valgus and hypermobility of the first ray: facts and fiction," International Orthopaedics, vol. 37, 2013, pp. 1655-1660.
Easley et al., "Current Concepts Review: Hallux Valgus Part I: Pathomechanics, Clinical Assessment, and Nonoperative Management," Foot and Ankle International, vol. 28, No. 5, May 2007, pp. 654-659.
Easley et al., "Current Concepts Review: Hallux Valgus Part II: Operative Treatment," Foot and Ankle International, vol. 28, No. 6, Jun. 2007, pp. 748-758.
Easley et al., "What is the Best Treatment for Hallux Valgus?," Evidence-Based Orthopaedics - The Best Answers to Clinical Questions, Chapter 73, 2009, pp. 479-491.
EBI Extra Small Rail Fixator, Biomet Trauma, retrieved Dec. 19, 2014, from the Internet: <http://footandanklefixation.com/product/biomet-trauma-ebi-extra-small-rail-fixator>, 7 pages.
Eustace et al., "Hallux valgus, first metatarsal pronation and collapse of the medial longitudinal arch—a radiological correlation," Skeletal Radiology, vol. 23, 1994, pp. 191-194.
Fallin et al., US Provisional Application Entitled Indexed Tri-Planar Osteotomy Guide and Method, U.S. Appl. No. 62/118,378, filed Feb. 19, 2015, 62 pages.
Fazal et al., "First metatarsophalangeal joint arthrodesis with two orthogonal two hole plates," Acta Orthopaedica et Traumatologica Turcica, vol. 52, 2018, pp. 363-366.
Feilmeier et al., "Incidence of Surgical Site Infection in the Foot and Ankle with Early Exposure and Showering of Surgical Sites: A Prospective Observation," The Journal of Foot and Ankle Surgery, vol. 53, 2014, pp. 173-175.
Feilmeier et al., "Reduction of Intermetatarsal Angle after First Metatarsophalangeal Joint Arthrodesis in Patients with Hallux Valgus," The Journal of Foot and Ankle Surgery, vol. 53, 2014, pp. 29-31.
Ferrari et al., "A Radiographic Study of the Relationship Between Metatarsus Adductus and Hallux Valgus," The Journal of Foot and Ankle Surgery, vol. 42, No. 1, 2003, pp. 9-14.
Ferreyra et al., "Can we correct first metatarsal rotation and sesamoid position with the 3D Lapidus procedure?," Foot and Ankle Surgery, vol. 28, No. 3, Apr. 2022, pp. 313-318.

(56) References Cited

OTHER PUBLICATIONS

Fishco, "A Straightforward Guide To The Lapidus Bunionectomy," Podiatry Today, Retrieved online from <https://www.hmpglobal-learningnetwork.com/site/podiatry/blogged/straightforward-guide-lapidus-bunionectomy>, dated Sep. 6, 2013, 5 pages.
Fishco, "Making the Lapidus Easy," The Podiatry Institute, Update 2014, Chapter 14, 2014, pp. 91-93.
Flavin et al., "Arthrodesis of the First Metatarsophalangeal Joint Using a Dorsal Titanium Contoured Plate," Foot & Ankle International, vol. 25, No. 11, Nov. 2004, pp. 783-787.
Fleming et al., "Results of Modified Lapidus Arthrodesis Procedure Using Medial Eminence as an Interpositional Autograft," The Journal of Foot & Ankle Surgery, vol. 50, 2011, pp. 272-275.
Fraissler et al., "Treatment of hallux valgus deformity," Efort Open Reviews, vol. 1, Aug. 2016, pp. 295-302.
Fuhrmann, "Arthrodesis of the First Tarsometatarsal Joint for Correction of the Advanced Splayfoot Accompanied by a Hallux Valgus," Operative Orthopadie und Traumatologie, No. 2, 2005, pp. 195-210.
Galli et al., "Enhanced Lapidus Arthrodesis: Crossed Screw Technique With Middle Cuneiform Fixation Further Reduces Sagittal Mobility," The Journal of Foot & Ankle Surgery, vol. 54, vol. 3, May/Jun. 2015, published online: Nov. 21, 2014, pp. 437-440.
Garthwait, "Accu-Cut System Facilitates Enhanced Precision," Podiatry Today, vol. 18, No. 6, Jun. 2005, 6 pages.
Gerard et al., "The Modified Lapidus Procedure," Orthopedics, vol. 31, No. 3, Mar. 2008, 7 pages.
Ghali et al., "The Management of Metatarsus Adductus et Supinatus," The Journal of Bone and Joint Surgery, vol. 66-B, No. 3, May 1984, pp. 376-380.
Giannoudis et al., "Hallux Valgus Correction," Practical Procedures in Elective Orthopaedic Surgery, Pelvis and Lower Extremity, Chapter 38, 2012, 22 pages.
Gonzalez Del Pino et al., "Variable Angle Locking Intercarpal Fusion System for Four-Corner Arthrodesis: Indications and Surgical Technique," Journal of Wrist Surgery, vol. 1, No. 1, Aug. 2012, pp. 73-78.
Gotte, "Entwicklung eines Assistenzrobotersystems fr die Knieendoprothetik," Forschungsberichte, Technische Universitat Munchen, 165, 2002, 11 pages, including partial English Translation.
Gould et al., "A Prospective Evaluation of First Metatarsophalangeal Fusion Using an Innovative Dorsal Compression Plating System," The Journal of Foot & Ankle Surgery, vol. 60, 2021, pp. 891-896.
Gregg et al., "Plantar plate repair and Weil osteotomy for metatarsophalangeal joint instability," Foot and Ankle Surgery, vol. 13, 2007, pp. 116-121.
Greiner, "The Jargon of Pedal Movements," Foot & Ankle International, vol. 28, No. 1, Jan. 2007, pp. 109-125.
Grondal et al., "A Guide Plate for Accurate Positioning of First Metatarsophalangeal Joint during Fusion," Operative Orthopdie Und Traumatologie, vol. 16, No. 2, 2004, pp. 167-178 (Abstract Only).
Groves, "Functional Position Joint Sectioning: Pre-Load Method for Lapidus Arthrodesis," The Podiatry Institute, Update 2015, Chapter 6, 2015, pp. 23-29.
Groves, "Operative Report," St. Tammany Parish Hospital, Date of Procedure, Mar. 26, 2014, 2 pages.
Gutteck et al., "Comparative study of Lapidus bunionectomy using different osteosynthesis methods," Foot and Ankle Surgery, vol. 19, 2013, pp. 218-221.
Gutteck et al., "Is it feasible to rely on intraoperative X ray in correcting hallux valgus?," Archives of Orthopaedic and Trauma Surgery, vol. 133, 2013, pp. 753-755.
Hardy et al., "Observations on Hallux Valgus," The Journal of Bone and Joint Surgery, vol. 33B, No. 3, Aug. 1951,pp. 376-391.
Hatch et al., "Analysis of Shortening and Elevation of the First Ray With Instrumented Triplane First Tarsometatarsal Arthrodesis," Foot & Ankle Orthopaedics, vol. 5, No. 4, 2020, pp. 1-8.
Hatch et al., "Triplane Hallux Abducto Valgus Classification," The Journal of Foot & Ankle Surgery, vol. 57, No. 5, Sep./Oct. 2018, published online: May 18, 2018, pp. 972-981.
Hetherington et al., "Evaluation of surgical experience and the use of an osteotomy guide on the apical angle of an Austin osteotomy," The Foot, vol. 18, 2008, pp. 159-164.
Hirao et al., "Computer assisted planning and custom-made surgical guide for malunited pronation deformity after first metatarsophalangeal joint arthrodesis in rheumatoid arthritis: A case report," Computer Aided Surgery, vol. 19, Nos. 1-3, 2014, pp. 13-19.
Ho et al., "Hallux rigidus," Efort Open Reviews, vol. 2, Jan. 2017, pp. 13-20.
Holmes, Jr., "Correction of the Intermetatarsal Angle Component of Hallux Valgus Using Fiberwire-Attached Endo- buttons," Revista Internacional de Ciencias Podologicas, vol. 6, No. 2, 2012, pp. 73-79.
Hunt et al., "Locked Versus Nonlocked Plate Fixation For Hallux MTP Arthrodesis," Foot and Ankle International, vol. 32, No. 7, Jul. 2011, pp. 704-709.
Integra, "Integra Large Qwix Positioning and Fixation Screw, Surgical Technique," 2012, 16 pages.
Klos et al., "Modified Lapidus arthrodesis with plantar plate and compression screw for treatment of hallux valgus with hypermobility of the first ray: A preliminary report," Foot and Ankle Surgery, vol. 19, 2013, pp. 239-244.
Jackson III et al., "The Surgical Learning Curve for Modified Lapidus Procedure for Hallux Valgus Deformity," Foot & Ankle Specialist, Jul. 2021, 5 pages.
Jeuken et al., "Long-term Follow-up of a Randomized Controlled Trial Comparing Scarf to Chevron Osteotomy in Hallux Valgus Correction," Foot & Ankle International, vol. 37, No. 7, 2016, pp. 687-695.
Kilmartin et al., "Combined rotation scarf and Akin osteotomies for hallux valgus: a patient focused 9 year follow up of 50 patients," Journal of Foot and Ankle Research, vol. 3, No. 2, 2010, 12 pages.
Kim et al., "A Multicenter Retrospective Review of Outcomes for Arthrodesis, Hemi-Metallic Joint Implant, and Resectional Arthroplasty in the Surgical Treatment of End-Stage Hallux Rigidus," The Journal of Foot and Ankle Surgery, vol. 51, 2012, pp. 50-56.
Kim et al., "A New Measure of Tibial Sesamoid Position in Hallux Valgus in Relation to the Coronal Rotation of the First Metatarsal in CT Scans," Foot and Ankle International, vol. 36, No. 8, 2015, pp. 944-952.
International Searching Authority, "International Search Report and Written Opinion", From Application No. PCT/US2023/074221, mailed Sep. 14, 2023, 14 pages.
"Foot and Ankle Instrument Set," Smith & Nephew, 2013, 2 pages.
"Lapidus Pearls: Gaining Joint Exposure to Decrease Non-Union," Youtube, Retrieved online from <https://www.youtube.com/watch?v =-jqJyE7pj-Y>, dated Nov. 2, 2009, 3 pages.
"Reconstructive Surgery of the Foot & Ankle," The Podiatry Institute, Update 2015, Conference Program, May 2015, 28 pages.
"Speed Continuous Active Compression Implant," BioMedical Enterprises, Inc., A120-029 Rev. 3, 2013, 4 pages.
"Visionaire: Patient Matched Cutting Blocks Surgical Procedure," Smith & Nephew, Inc., 2009, 2 pages.
Dayton et al., "A new triplanar paradigm for bunion management," Lower Extremity Review, Apr. 2015, 9 pages.
Dayton et al., "A User-Friendly Method of Pin Site Management for External Fixators," Foot and Ankle Specialist, Sep. 16, 2011, 4 pages.
Dayton et al., "American College of Foot and Ankle Surgeons' Clinical Consensus Statement: Perioperative Prophylactic Antibiotic Use in Clean Elective Foot Surgery," The Journal of Foot and Ankle Surgery, Article in Press, 2015, 7 pages.
Dayton et al., "Clarification of the Anatomic Definition of the Bunion Deformity," The Journal of Foot and Ankle Surgery, vol. 53, 2014, pp. 160-163.
Dayton et al., "Comparison of Complications for Internal and External Fixation for Charcot Reconstruction: A Systematic Review," The Journal of Foot and Ankle Surgery, Article in Press, 2015, 4 pages.

(56) References Cited

OTHER PUBLICATIONS

Dayton et al., "Complications of Metatarsal Suture Techniques for Bunion Correction: A Systematic Review of the Literature," The Journal of Foot and Ankle Surgery, Article in Press, 2015, 3 pages.
Dayton et al., "Does Postoperative Showering or Bathing of a Surgical Site Increase the Incidence of Infection? A Systematic Review of the Literature," The Journal of Foot and Ankle Surgery, vol. 52, 2013, pp. 612-614.
Dayton et al., "Dorsal Suspension Stitch: An Alternative Stabilization After Flexor Tenotomy for Flexible Hammer Digit Syndrome," The Journal of Foot and Ankle Surgery, vol. 48, No. 5, Sep./Oct. 2009, pp. 602-605.
Dayton et al., "Effectiveness of a Locking Plate in Preserving Midcalcaneal Length and Positional Outcome after Evans Calcaneal Osteotomy: A Retrospective Pilot Study," The Journal of Foot and Ankle Surgery, vol. 52, 2013, pp. 710-713.
Dayton et al., "Hallux Varus as Complication of Foot Compartment Syndrome," The Journal of Foot and Ankle Surgery, vol. 50, 2011, pp. 504-506.
Dayton et al., "Measurement of Mid-Calcaneal Length on Plain Radiographs: Reliability of a New Method," Foot and Ankle Specialist, vol. 4, No. 5, Oct. 2011, pp. 280-283.
Dayton et al., "Observed Changes in First Metatarsal and Medial Cuneiform Positions after First Metatarsophalangeal Joint Arthrodesis," The Journal of Foot and Ankle Surgery, vol. 53, 2014, pp. 32-35.
Dayton et al., "Observed Changes in Radiographic Measurements of the First Ray after Frontal Plane Rotation of the First Metatarsal in a Cadaveric Foot Model," The Journal of Foot and Ankle Surgery, Article in Press, 2014, 5 pages.
Dayton et al., "Principles of Management of Growth Plate Fractures in the Foot and Ankle," Clinics in Podiatric Medicine and Surgery, Pediatric Foot Deformities, Oct. 2013, 17 pages.
Dayton et al., "Reduction of the Intermetatarsal Angle after First Metatarsal Phalangeal Joint Arthrodesis: A Systematic Review," The Journal of Foot and Ankle Surgery, Article in Press, 2014, 4 pages.
Dayton et al., "Technique for Minimally Invasive Reduction of Calcaneal Fractures Using Small Bilateral External Fixation," The Journal of Foot and Ankle Surgery, Article in Press, 2014, 7 pages.
Dayton et al., "The Extended Knee Hemilithotomy Position for Gastrocnemius Recession," The Journal of Foot and Ankle Surgery, vol. 49, 2010, pp. 214-216.
De Geer et al., "A New Measure of Tibial Sesamoid Position in Hallux Valgus in Relation to the Coronal Rotation of the First Metatarsal in CT Scans," Foot and Ankle International, Mar. 26, 2015, 9 pages.
Decarbo et al., "Locking Plates: Do They Prevent Complications?," Podiatry Today, Apr. 2014, 7 pages.
Decarbo et al., "Resurfacing Interpositional Arthroplasty for Degenerative Joint Diseas of the First Metatarsalphalangeal Joint," Podiatry Management, Jan. 2013, pp. 137-142.
Decarbo et al., "The Weil Osteotomy: A Refresher," Techniques in Foot and Ankle Surgery, vol. 13, No. 4, Dec. 2014, pp. 191-198.
Deheer et al., "Procedure-Specific Hardware Removal After Evans Osteotomy," Journal of the American Podiatric Medical Association, vol. 110, No. 2, Mar./Apr. 2020, 7 pages.
Didomenico et al., "Correction of Frontal Plane Rotation of Sesamoid Apparatus during the Lapidus Procedure: A Novel Approach," The Journal of Foot and Ankle Surgery, vol. 53, 2014, pp. 248-251.
Didomenico et al., "Lapidus Bunionectomy: First Metatarsal-Cuneiform Arthrodesis," McGlamrys Comprehensive Textbook of Foot and Ankle Surgery, Fourth Edition, vol. 1, Chapter 31, 2013, 24 pages.
Dinapoli et al., "Metatarsal Osteotomy for the Correction of Metatarsus Adductus," Reconstructive Surgery of the Foot and Leg, 1989, pp. 242-250.
"Futura Forefoot Implant Arthroplasty Products", Tornier, Inc., 2008, 14 pages.
HAT-TRICK Lesser Toe Repair System, Foot and Ankle Technique Guide, Metatarsal Shortening Osteotomy Surgical Technique, Smith & Nephew, 2014, 16 pages.
HAT-TRICK Lesser Toe Repair System, Smith & Nephew, Brochure, Aug. 2014, 12 pages.
Hoffmann II Compact External Fixation System, Stryker, Brochure, Literature No. 5075-1-500, 2006, 12 pages.
Hoffmann II Micro Lengthener, Stryker, Operative Technique, Literature No. 5075-2-002, 2008, 12 pages.
Hoffmann Small System External Fixator Orthopedic Instruments, Stryker, retrieved Dec. 19, 2014, from the Internet: <http://www.alibaba.com/product-detail/Stryker-Hoffmann-Small-System-External-Fixator_1438850129.html>, 3 pages.
"Patient to Patient Precision, Accu-Cut, Osteotomy Guide System," BioPro, Foot & Ankle International Journal, vol. 23, No. 8, Aug. 2002, 2 pages.
"Prophecy Inbone Preoperative Navigation Guides," Wright Medical Technology, Inc., Nov. 2013, 6 pages.
Rayhack Ulnar Shortening Generation II Low-Profile Locking System Surgical Technique, Wright Medical Technology, Inc., Dec. 2013, 20 pages.
Smith & Nephew scores a HAT-TRICK with its entry into the high-growth hammer toe repair market, Smith & Nephew, Jul. 31, 2014, 2 pages.
"Lag Screw Target Bow," Stryker Leibinger GmbH & Co. KG, Germany 2004, 8 pages.
Claim Chart for Fishco, "A Straightforward Guide to the Lapidus Bunionectomy," HMP Global (Sep. 6, 2013), Exhibit B2 of Defendant Fusion Orthopedics LLC's Invalidity Contentions, No. CV-22-00490-PHX-SRB, US District Court for the District of Arizona, Aug. 27, 2022, 67 pages.
Claim Chart for Fishco, "Making the Lapidus Easy," The Podiatry Institute (Apr. 2014), Exhibit B1 of Defendant Fusion Orthopedics LLC's Invalidity Contentions, No. CV-22-00490-PHX-SRB, US District Court for the District of Arizona, Aug. 27, 2022, 97 pages.
Claim Chart for Groves Public Use (Mar. 26, 2014), Exhibit B4 of Defendant Fusion Orthopedics LLC's Invalidity Contentions, No. CV-22-00490-PHX-SRB, US District Court for the District of Arizona, Aug. 27, 2022, 161 pages.
Claim Chart for Groves, "Functional Position Joint Sectioning: Pre-Load Method for Lapidus Arthrodesis," Update 2015: Proceedings of the Annual Meeting of the Podiatry Institute, Chpt. 6, pp. 23-29 (Apr. 2015), Exhibit B3 of Defendant Fusion Orthopedics LLC's Invalidity Contentions, No. CV-22-00490-PHX-SRB, US District Court for the District of Arizona, Aug. 27, 2022, 151 pages.
Claim Chart for Mote, "First Metatarsal-Cuneiform Arthrodesis for the Treatment of First Ray Pathology: A Technical Guide," The Journal Foot & Ankle Surgery (Sep. 1, 2009), Exhibit B5 of Defendant Fusion Orthopedics LLC's Invalidity Contentions, No. CV-22-00490-PHX-SRB, US District Court for the District of Arizona, Aug. 27, 2022, 21 pages.
Claim Chart for U.S. Pat. No. 10,376,268 to Fallin et al., entitled "Indexed Tri-Planar Osteotomy Guide and Method," issued Aug. 13, 2019, Exhibit B6 of Defendant Fusion Orthopedics LLC's Invalidity Contentions, No. CV-22-00490-PHX-SRB, US District Court for the District of Arizona, Aug. 27, 2022, 155 pages.
Claim Chart for U.S. Pat. No. 8,282,645 to Lawrence et al., entitled "Metatarsal Bone Implant Cutting Guide," issued Jan. 18, 2010, Exhibit B7 of Defendant Fusion Orthopedics LLC's Invalidity Contentions, No. CV-22-00490-PHX-SRB, US District Court for the District of Arizona, Aug. 27, 2022, 76 pages.
Claim Chart for U.S. Pat. No. 9,452,057 to Dacosta et al., entitled "Bone Implants and Cutting Apparatuses and Methods," issued Apr. 8, 2011, Exhibit B8 of Defendant Fusion Orthopedics LLC's Invalidity Contentions, No. CV-22-00490-PHX-SRB, US District Court for the District of Arizona, Aug. 27, 2022, 110 pages.
Defendant Fusion Orthopedics LLC's Invalidity Contentions, No. CV-22-00490-PHX-SRB, US District Court for the District of Arizona, Aug. 27, 2022, 41 pages.
Kurup et al., "Midfoot arthritis- current concepts review," Journal of Clinical Orthopaedics and Trauma, vol. 11, 2020, pp. 399-405.

(56) References Cited

OTHER PUBLICATIONS

La Reaux et al., "Metatarsus adductus and hallux abducto valgus: their correlation," The Journal of Foot Surgery, vol. 26, No. 4, Jul. 1987, pp. 304-308, Abstract Only.
Langan et al., "Maintenance of Correction of the Modified Lapidus Procedure With a First Metatarsal to Intermediate Cuneiform Cross-Screw Technique," Foot & Ankle International, vol. 41, No. 4, Apr. 1, 2020, published online: Dec. 26, 2019, pp. 426-436.
Lapidus, "The Author's Bunion Operation From 1931 to 1959," Clinical Orthopaedics, vol. 16, 1960, pp. 119-135.
Latif et al., "First metatarsophalangeal fusion using joint specific dorsal plate with interfragmentary screw augmentation: Clinical and radiological outcomes," Foot and Ankle Surgery, vol. 25, 2019, pp. 132-136.
Le et al., "Tarsometatarsal Arthrodesis," Operative Techniques in Foot and Ankle Surgery, Section II, Chapter 40, 2011, pp. 281-285.
Lee et al., "Technique Tip: Lateral Soft-Tissue Release for Correction of Hallux Valgus Through a Medial Incision Using A Dorsal Flap Over the First Metatarsal," Foot & Ankle International, vol. 28, No. 8, Aug. 2007, pp. 949-951.
Li et al., "Evolution of Thinking of the Lapidus Procedure and Fixation," Foot and Ankle Clinics, vol. 25, No. 1, Mar. 2020, published online: Dec. 16, 2019, pp. 18 pages.
Lieske et al., "Implantation einer Sprunggelenktotalendo-prothese vom Typ Salto 2," Operative Orthopdie und Traumatologie, vol. 26, No. 4, 2014, pp. 401-413, including English Abstract on p. 403.
Little, "Joint Arthrodesis For Hallux Valgus," Clinics in Podiatric Medicine and Surgery, Hallux Abducto Valgus Surgery, updated Apr. 19, 2014, retrieved online from <https://www.footankleinstitute.com/first-metatarsophalangeal-joint-arthrodesis-in-the-treatment-of-hallux-valgus>, 7 pages.
Lopez et al., "Metatarsalgia: Assessment Algorithm and Decision Making," Foot and Ankle Clinics, vol. 24, No. 4, Dec. 2019, published online: Sep. 25, 2019, pp. 561-569.
MAC (Multi Axial Correction) Fixation System, Biomet Trauma, retrieved Dec. 19, 2014, from the Internet: <http:// footandanklefixation.com/product/biomet-trauma-mac-multi-axial-correction-fixation-system>, 7 pages.
Machacek Jr. et al., "Salvage of a Failed Keller Resection Arthroplasty," The Journal of Bone and Joint Surgery, vol. 86A, No. 6, Jun. 2004, pp. 1131-1138.
Magin, "Computernavigierter Gelenkersatz am Knie mit dem Orthopilot," Operative Orthopdie und Traumatologie, vol. 22, No. 1, 2010, pp. 63-80, including English Abstract on p. 64.
Magin, "Die belastungsstabile Lapidus-Arthrodese bei Hallux-valgus-Deformitt mittels IVP-Plattenfixateur (V-TEK- System)," Operative Orthopdie und Traumatologie, vol. 26, No. 2, 2014, pp. 184-195, including English Abstract on p. 186.
Marshall et al., "The identification and appraisal of assessment tools used to evaluate metatarsus adductus: a systematic review of their measurement properties," Journal of Foot and Ankle Research, vol. 11, No. 25, 2018, 10 pages.
McAleer et al., "A systematic approach to the surgical correction of combined hallux valgus and metatarsus adductus deformities," The Journal of Foot & Ankle Surgery, May 21, 2021, 6 pages.
McAleer et al., "Radiographic Outcomes Following Triplanar Correction of Combined Hallux Valgus and Metatarsus Adductus Deformities," ACFAS Scientific Conference, Poster, Feb. 2022, 1 page.
McCabe et al., "Anatomical reconstruction of first ray instability hallux valgus with a medial anatomical TMTJ1 plate," Foot and Ankle Surgery, vol. 27, No. 8, Dec. 2021, pp. 869-873.
Mehtar et al., "Outcomes of bilateral simultaneous hallux MTPJ fusion," Foot and Ankle Surgery, vol. 27, 2021, pp. 213-216.
Miller et al., "Variable Angle Locking Compression Plate as Alternative Fixation for Jones Fractures: A Case Series," Kansas Journal of Medicine, vol. 12, No. 2, May 2019, pp. 28-32.
Mini Joint Distractor, Arthrex, retrieved Dec. 19, 2014, from the Internet: <http://www.arthrex.com/foot-ankle/mini-joint-distractor/products>, 2 pages.
MiniRail System, Small Bone Innovations, Surgical Technique, 2010, 24 pages.
Miyake et al., "Three-Dimensional Corrective Osteotomy for Malunited Diaphyseal Forearm Fractures Using Custom-Made Surgical Guides Based on Computer Simulation," JBJS Essential Surgical Techniques, vol. 2, No. 4, 2012, 11 pages.
Mizuno et al., "Detorsion Osteotomy of the First Metatarsal Bone in Hallux Valgus," Japanese Orthopaedic Association, Tokyo, 1956; 30:813-819.
Modular Rail System: External Fixator, Smith & Nephew, Surgical Technique, 2013, 44 pages.
Monnich et al., "A Hand Guided Robotic Planning System for Laser Osteotomy in Surgery," World Congress on Medical Physics and Biomedical Engineering vol. 25/6: Surgery, Nimimal Invasive Interventions, Endoscopy and Image Guided Therapy, Sep. 7-12, 2009, pp. 59-62, (Abstract Only).
Moore et al., "Effect Of Ankle Flexion Angle On Axial Alignment Of Total Ankle Replacement," Foot and Ankle International, vol. 31, No. 12, Dec. 2010, pp. 1093-1098, (Abstract Only).
Mortier et al., "Axial Rotation of the First Metatarsal Head in a Normal Population and Hallux Valgus Patients," Orthopaedics and Traumatology: Surgery and Research, vol. 98, 2012, pp. 677-683.
Mote et al., "First Metatarsal-Cuneiform Arthrodesis for the Treatment of First Ray Pathology: A Technical Guide," JFAS Techniques Guide, vol. 48, No. 5, Sep./Oct. 2009, pp. 593-601.
Myerson, "Cuneiform-Metatarsal Arthrodesis," The Foot and Ankle, Chapter 9, 1997, pp. 107-117.
Nagy et al., "The AO Ulnar Shortening Osteotomy System Indications and Surgical Technique," Journal of Wrist Surgery, vol. 3, No. 2, 2014, pp. 91-97.
NexFix from Nexa Orthopedics, MetaFix I from Merete Medical, Inc. and The BioPro Lower Extremities from BioPro, found in Foot & Ankle International Journal, vol. 28, No. 1, Jan. 2007, 4 pages.
Nix et al., "Prevalence of hallux valgus in the general population: a systematic review and meta-analysis," Journal of Foot and Ankle Research, vol. 3, No. 21, 2010, 9 pages.
Odenbring et al., "A guide instrument for high tibial osteotomy," Acta Orthopaedica Scandinavica, vol. 60, No. 4, 1989, pp. 449-451.
Okuda et al., "Postoperative Incomplete Reduction of the Sesamoids as a Risk Factor for Recurrence of Hallux Valgus," The Journal of Bone and Joint Surgery, vol. 91-A, No. 1, Jul. 2009, pp. 1637-1645.
Okuda et al., "Proximal Metatarsal Osteotomy for Hallux Valgus: Comparison of Outcome for Moderate and Severe Deformities," Foot and Ankle International, vol. 29, No. 7, Jul. 2008, pp. 664-670.
Okuda et al., "The Shape of the Lateral Edge of the First Metatarsal Head as a Risk Factor for Recurrence of Hallux Valgus," The Journal of Bone and Joint Surgery, vol. 89, 2007, pp. 2163-2172.
Osher et al., "Accurate Determination of Relative Metatarsal Protrusion with a Small Intermetatarsal Angle: A Novel Simplified Method," The Journal of Foot & Ankle Surgery, vol. 53, No. 5, Sep./Oct. 2014, published online: Jun. 3, 2014, pp. 548-556.
Otsuki et al., "Developing a novel custom cutting guide for curved per-acetabular osteotomy," International Orthopaedics (SICOT), vol. 37, 2013, pp. 1033-1038.
Park et al., "Comparative analysis of clinical outcomes of fixed-angle versus variable-angle locking compression plate for the treatment of Lisfranc injuries," Foot and Ankle Surgery, vol. 26, 2020, pp. 338-342.
Patel et al., "Modified Lapidus Arthrodesis: Rate of Nonunion in 227 Cases," The Journal of Foot & Ankle Surgery, vol. 43, No. 1, Jan./Feb. 2004, pp. 37-42.
Pentikainen et al., "Preoperative Radiological Factors Correlated to Long-Term Recurrence of Hallux Valgus Following Distal Chevron Osteotomy," Foot & Ankle International, vol. 35, No. 12, 2014, pp. 1262-1267.
Peters et al., "Flexor Hallucis Longus Tendon Laceration as a Complication of Total Ankle Arthroplasty," Foot & Ankle International, vol. 34, No. 1, 2013, pp. 148-149.
Ray et al., "Hallux Valgus," Foot & Ankle Orthopaedics, vol. 4, No. 2, 2019, pp. 1-12.
Ray et al., "Multicenter Early Radiographic Outcomes of Triplanar Tarsometatarsal Arthrodesis With Early Weightbearing," Foot & Ankle International, vol. 40, No. 8, 2019, pp. 955-960.

(56) References Cited

OTHER PUBLICATIONS

Ray et al., "Multicenter Early Radiographic Outcomes of Triplanar Tarsometatarsal Arthrodesis With Early Weightbearing," Foot & Ankle International, vol. 40, No. 8, Aug. 1, 2019, published online: May 5, 2019, 7 pages.
Obviousness Chart, Exhibit C of Defendant Fusion Orthopedics LLC's Invalidity Contentions, No. CV-22-00490-PHX-SRB, US District Court for the District of Arizona, Aug. 27, 2022, 153 pages.
Michelangelo Bunion System, Surgical Technique, Instratek Incorporated, publication date unknown, 4 pages.
Prior Art Publications, Exhibit A of Defendant Fusion Orthopedics LLC's Invalidity Contentions, No. CV-22-00490-PHX-SRB, US District Court for the District of Arizona, Aug. 27, 2022, 3 pages.
"Arthrodesis of the Tarsometatarsal Joint," Retrieved from https://musculoskeletalkey.com/arthrodesis-of-the-tarsometatarsal-joint/, posted Apr. 18, 2019, 11 pages.
Accu-Cut Osteotomy Guide System, BioPro, Brochure, Oct. 2018, 2 pages.
"Acumed Osteotomiesystem Operationstechnik", Acumed, 2014, 19 pages (including 3 pages English translation).
Aiyer et al., "Prevalence of Metatarsus Adductus in Patients Undergoing Hallux Valgus Surgery," Foot & Ankle International, vol. 35, No. 12, 2014, pp. 1292-1297.
Albano et al., "Biomechanical Study of Transcortical or Transtrabecular Bone Fixation of Patellar Tendon Graft wih Bioabsorbable Pins in ACL Reconstruction in Sheep," Revista Brasileira de Ortopedia (Rev Bras Ortop.) vol. 47, No. 1, 2012, pp. 43-49.
Alvine et al., "Peg and Dowel Fusion of the Proximal Interphalangeal Joint," Foot & Ankle, vol. 1, No. 2, 1980, pp. 90-94.
Anderson et al., "Uncemented STAR Total Ankle Prostheses," The Journal of Bone and Joint Surgery, vol. 86(1, Suppl 2), Sep. 2004, pp. 103-111, (Abstract Only).
Arthrex, "Comprehensive Foot System," Retrieved online from <https://www.arthrex.com/resources/animation/8U3iaPvY6kO8bwFAwZF50Q/comprehensive-foot-system?referringTeam=foot_and_ankle>, dated Aug. 27, 2013, 3 pages.
Baravarian, "Why the Lapidus Procedure is Ideal for Bunions," Podiatry Today, Retrieved online from <https://www.hmpglobal-learhmpgloballe.com/site/podipodi/article/5542>, dated May 2006, 8 pages.
Bauer et al., "Offset-V Osteotomy of the First Metatarsal Shaft in Hallux Abducto Valgus," McGlamrys Comprehensive Textbook of Foot and Ankle Surgery, Fourth Edition, vol. 1, Chapter 29, 2013, 26 pages.
Bednarz et al., "Modified Lapidus Procedure for the Treatment of Hypermobile Hallux Valgus," Foot & Ankle International, vol. 21, No. 10, Oct. 2000, pp. 816-821.
Bennett et al., "Intraosseous Sliding Plate Fixation Used in Double Osteotomy Bunionectomy," Foot & Ankle International, vol. 40, No. 1, 2019, pp. 85-88.
Blomer, "Knieendoprothetik—Herstellerische Probleme und technologische Entwicklungen," Orthopade, vol. 29, 2000, pp. 688-696, including English Abstract on p. 689.
Bouaicha et al., "Fixation of Maximal Shift Scarf Osteotomy with Inside-Out Plating: Technique Tip," Foot & Ankle International, vol. 32, No. 5, May 2011, pp. 567-569.
Buda et al., "Effect of Fixation Type and Bone Graft on Tarsometatarsal Fusion," Foot & Ankle International, vol. 39, No. 12, 2018, pp. 1394-1402.
Carr et al., "Correctional Osteotomy for Metatarsus Primus Varus and Hallux Valgus," The Journal of Bone and Joint Surgery, vol. 50-A, No. 7, Oct. 1968, pp. 1353-1367.
Catanese et al., "Measuring Sesamoid Position in Hallux Valgus: When Is the Sesamoid Axial View Necessary," Foot and Ankle Specialist, 2014, 3 pages.
Chesser et al., "New Advances With The Tarsometatarsal Arthrodesis," Podiatry Today, vol. 30, No. 10, Sep. 27, 2017, 15 pages.
Chomej et al., "Lateralising DMMO (MIS) for simultaneous correction of a pes adductus during surgical treatment of a hallux valgus," The Foot, vol. 45, Dec. 2020, 33 pages.
Cichero et al., "Different fixation constructs and the risk of non-union following first metatarsophalangeal joint arthrodesis," Foot and Ankle Surgery, vol. 27, 2021, pp. 789-792.
Coetzee et al., "Revision Hallux Valgus Correction," Operative Techniques in Foot and Ankle Surgery, Section I, Chapter 15, 2011, pp. 84-96.
Coetzee et al., "The Lapidus Procedure: A Prospective Cohort Outcome Study," Foot & Ankle International, vol. 25, No. 8, Aug. 2004, pp. 526-531.
Collan et al., "The biomechanics of the first metatarsal bone in hallux valgus: A preliminary study utilizing a weight bearing extremity CT," Foot and Ankle Surgery, vol. 19, 2013, pp. 155-161.
Conti et al., "Effect of the Modified Lapidus Procedure for Hallux Valgus on Foot Width," Foot & Ankle International, Feb. 1, 2020, published online: Oct. 30, 2019, 6 pages.
Conti et al., "Effect of the Modified Lapidus Procedure on Pronation of the First Ray in Hallux Valgus," Foot & Ankle International, Feb. 1, 2020, published online: Oct. 16, 2019, 8 pages.
Cottom, "Fixation of the Lapidus Arthrodesis with a Plantar Interfragmentary Screw and Medial Low Profile Locking Plate," The Journal of Foot & Ankle Surgery, vol. 51, 2012, pp. 517-522.
Coughlin, "Fixation of the Lapidus Arthrodesis with a Plantar Interfragmentary Screw and Medial Low Profile Locking Plate," Orthopaedics and Traumatology, vol. 7, 1999, pp. 133-143.
Crawford et al., "Metatarsus Adductus: Radiographic and Pathomechanical Analysis," Chapter 5, 2014, 6 pages.
Cruz et al., "Does Hallux Valgus Exhibit a Deformity Inherent to the First Metatarsal Bone?" The Journal of Foot & Ankle Surgery, vol. 58, No. 6, Nov. 2019, pp. 1210-1214.
Curran et al., "Functional Capabilities After First Metatarsal Phalangeal Joint Arthrodesis Using a Locking Plate and Compression Screw Construct," The Journal of Foot & Ankle Surgery, vol. 61, No. 1, Jan./Feb. 2022, pp. 79-83.
D'Amico et al., "Motion of the First Ray: Clarification Through Investigation," Journal of the American Podiatry Association, vol. 69, No. 1, Jan. 1979, pp. 17-23.
Dahlgren et al., "First Tarsometatarsal Fusion Using Saw Preparation vs. Standard Preparation of the Joint: A Cadaver Study," Foot & Ankle Orthopaedics, vol. 4, No. 4, Oct. 2019, 2 pages.
Dalat et al., "Does arthrodesis of the first metatarsophalangeal joint correct the intermetatarsal M1M2 angle? Analysis of a continuous series of 208 arthrodeses fixed with plates," Orthopaedics & Traumatology: Surgery & Research, vol. 101, 2015, pp. 709-714.
Dayton et al., "Biomechanical Characteristics of Biplane Multiplanar Tension-Side Fixation for Lapidus Fusion," The Journal of Foot & Ankle Surgery, vol. 57, 2018, pp. 761-765.
Dayton et al., "Biwinged Excision for Round Pedal Lesions," The Journal of Foot and Ankle Surgery, vol. 35, No. 3, 1996, pp. 244-249.
Dayton et al., "Comparison of Radiographic Measurements Before and After Triplane Tarsometatarsal Arthrodesis for Hallux Valgus," The Journal of Foot & Ankle Surgery, vol. 59, 2020, pp. 291-297.
Dayton et al., "Comparison of Tibial Sesamoid Position on Anteroposterior and Axial Radiographs Before and After Triplane Tarsal Metatarsal Joint Arthrodesis," The Journal of Foot & Ankle Surgery, vol. 56, 2017, pp. 1041-1046.
Dayton et al., "Early Weightbearing After First Metatarsophalangeal Joint Arthrodesis: A Retrospective Observational Case Analysis," The Journal of Foot and Ankle Surgery, vol. 43, No. 3, May/Jun. 2004, pp. 156-159.
Dayton et al., "Evidence-Based Bunion Surgery: A Critical Examination of Current and Emerging Concepts and Techniques," Springer International Publishing, 2017, 254 pages.
Dayton et al., "Is Our Current Paradigm for Evaluation and Management of the Bunion Deformity Flawed? A Discussion of Procedure Philosophy Relative to Anatomy," The Journal of Foot and Ankle Surgery, vol. 54, 2015, pp. 102-111.
Dayton et al., "Medial Incision Approach to the First Metatarsophalangeal Joint," The Journal of Foot and Ankle Surgery, vol. 40, No. 6, November/Dec. 2001, pp. 414-417.
Dayton et al., "Observed Changes in Radiographic Measurements of the First Ray after Frontal and Transverse Plane Rotation of the

(56) References Cited

OTHER PUBLICATIONS

Hallux: Does the Hallux Drive the Metatarsal in a Bunion Deformity? ," The Journal of Foot and Ankle Surgery, vol. 53, 2014, pp. 584-587.
Dayton et al., "Progression of Healing on Serial Radiographs Following First Ray Arthrodesis in the Foot Using a Biplanar Plating Technique Without Compression," The Journal of Foot & Ankle Surgery, 2018, 7 pages.
Dayton et al., "Quantitative Analysis of the Degree of Frontal Rotation Required to Anatomically Align the First Metatarsal Phalangeal Joint During Modified Tarsal-Metatarsal Arthrodesis Without Capsular Balancing," The Journal of Foot and Ankle Surgery, 2015, pp. 1-6.
Dayton et al., "Reduction of the Intermetatarsal Angle after First Metatarsophalangeal Joint Arthrodesis in Patients with Moderate and Severe Metatarsus Primus Adductus," The Journal of Foot and Ankle Surgery, vol. 41, No. 5, September/Oct. 2002, pp. 316-319.
Dayton et al., "Use of the Z Osteotomy for Tailor Bunionectomy," The Journal of Foot and Ankle Surgery, vol. 42, No. 3, May/Jun. 2003, pp. 167-169.
Dayton, "Tarsal-Metatarsal Joint: Primary & Revision Arthrodesis," Apr. 2014, 38 pages.
Boffeli et al., "Can We Abandon Saw Wedge Resection in Lapidus Fusion? A Comparative Study of Joint Preparation Techniques Regarding Correction of Deformity, Union Rate, and Preservation of First Ray Length," The Journal of Foot and Ankle Surgery, vol. 58, No. 6, Nov. 2019, published online: Sep. 25, 2019, pp. 1118-1124.
Dayton et al., "Comparison of the Mechanical Characteristics of a Universal Small Biplane Plating Technique Without Compression Screw and Single Anatomic Plate With Compression Screw," The Journal of Foot & Ankle Surgery, vol. 55, No. 3, May/Jun. 2016, published online: Feb. 9, 2016, pp. 567-571.
Dayton et al., "Relationship of Frontal Plane Rotation of First Metatarsal to Proximal Articular Set Angle and Hallux Alignment in Patients Undergoing Tarsometatarsal Arthrodesis for Hallux Abducto Valgus: A Case Series and Critical Review of the Literature," The Journal of Foot & Ankle Surgery, 2013, Article in Press, Mar. 1, 2013, 7 pages.

* cited by examiner 80
104
92
92
88
136
133
90
134
RIGHT
130
135
86
132

80
86
132
135
134
88
LEFT
136
130
90
106
92
82
133
92
84

194
196
198
188
192
190
150
154

210
206
222
200

200
214
212
50
20
210
30
40
10
222

200
214
212
50
20
40
30
210
10
222
120
298

200
188
20
212
214
40
10
210
20
222

200
150
188
20
212
214
210
10
222

200
100
188
98
212
214
210
10
150
222

98
20
10
210
150
100
222
200

200
310
320
210
222

REVERSIBLE COMPRESSOR-DISTRACTOR FOR BONE REALIGNMENT PROCEDURES

CROSS-REFERENCE

This application claims the benefit of U.S. Provisional Patent Application No. 63/406,436, filed Sep. 14, 2023, the entire contents of which are incorporated herein by reference.

TECHNICAL FIELD

This disclosure relates generally to devices and techniques for repositioning bones and, more particularly, to devices and techniques for repositioning bones in the foot.

BACKGROUND

Bones within the human body, such as bones in the foot, may be anatomically misaligned. For example, one common type of bone deformity is hallux valgus, which is a progressive foot deformity in which the first metatarsophalangeal joint is affected and is often accompanied by significant functional disability and foot pain. The metatarsophalangeal joint is laterally deviated, resulting in an abduction of the first metatarsal while the phalanges adduct. This often leads to development of soft tissue and a bony prominence on the medial side of the foot, which is called a bunion.

Surgical intervention may be used to correct a bunion deformity. A variety of different surgical procedures exist to correct bunion deformities and may involve removing the abnormal bony enlargement on the first metatarsal and/or attempting to realign the first metatarsal relative to the adjacent metatarsal. Surgical instruments that can facilitate efficient, accurate, and reproducible clinical results are useful for practitioners performing bone realignment techniques.

SUMMARY

In general, this disclosure is directed to devices and techniques that can be used during a surgical bone realignment procedure. In some examples, a compressor-distractor device is described that may be used during a surgical procedure, such as a surgical procedure to correct a bunion deformity. The compressor-distractor can include first and second engagement arms that each define pin-receiving holes. The first and second engagement arms can be engaged with corresponding pins inserted into underlying bone portions. The compressor-distractor may also include an actuator operatively coupled to the first and second engagement arms. For example, the first and second engagement arms of the compressor-distractor may be movably connected to each other via a threaded rod. Rotation of an actuator knob attached to the threaded rod can cause the first and second engagement arms to move relative to each other. This can apply a compression force to the bone portions in which the pins engaged with the first and second engagement arms are inserted.

In practice, a clinician performing a surgical procedure, such a bone realignment procedure on a foot of a patient, may be provided with multiple different compressor-distractor device. The clinician may be provided with one compressor-distractor configured to be used on the right foot of the patient and another compressor-distractor configured to be used on the left foot of the patient. Each compressor-distractor may be configured for the anatomical attributes of the left and right feet, respectively, such that the compressor-distractors are not interchangeably used between a surgical procedure performed on a left foot and a surgical procedure performed on a right foot. This can introduce cost and complexity to the operating environment, necessitating additional compressor-distractor inventory raising a potential that the clinician is provided with the wrong compressor-distractor for the specific surgical procedure being performed.

In accordance with some examples of the present disclosure, a reversible compressor-distractor is described that can be used in multiple different orientations. The reversible compressor-distractor may include a first engagement arm that defines multiple different pin-receiving holes and a second engagement arm that defines at least one pin-receiving hole. The pin-receiving holes provided by the first engagement arm may be angled relative to the pin-receiving hole defined by the second engagement arm. By configuring the pin-receiving holes of the first engagement arm to be angled relative to the pin-receiving hole of the second engagement arm, a correction force may be applied to one bone portion relative to another bone portion as the compressor-distractor is engaged with pins inserted into each bone portion. For example, as the compressor-distractor is guided onto pins inserted into each bone portion, the relative angulation between a pin-receiving hole defined by the first engagement arm and a pin-receiving hole defined by the second engagement arm may cause the pins, and correspondingly bone portions into which the pins are inserted, to move relative to each other. This can impart or reinforce a corrective realignment of one bone portion relative to the other bone portion.

In some configurations, the reversible compressor-distractor is configured to be flipped (e.g., inverted 180 degrees) between a first orientation and a second orientation. One or both engagement arms of the reversible compressor-distractor may include one pin-receiving hole to be used when the reversible compressor-distractor is in the first orientation and a second pin-receiving hole to be used when the reversible compressor-distractor is in the second orientation. For example, the reversible compressor-distractor may include a pin-receiving hole extending through a first side of the first engagement arm to be used when the reversible compressor-distractor is in the first orientation and another pin-receiving hole extending through a second side of the first engagement arm to be used when the reversible compressor-distractor is in the second orientation. The two pin-receiving holes may define mirror image orientations with respect to each other, e.g., allowing the two pin-receiving holes to be interchangeably used as the reversible compressor-distractor is flipped between orientations.

The pin-receiving holes extending through the different sides of the first engagement arm can have entry and/or exit locations that are sufficiently offset from each other to help avoid the clinician inadvertently inserting the wrong pin-receiving hole. In some examples, the second engagement arm provides a single pin-receiving hole in which the exit of the pin-receiving hole when the reversible compressor-distractor is in the first orientation is used as the entrance of the pin-receiving hole when the reversible compressor-distractor is in the second orientation. The reversible compressor-distractor can be used in the first orientation for one foot (e.g., right or left foot) and the second orientation for the other foot.

The reversible compressor-distractor may be used during a surgical procedure in which one or more other surgical instruments are also used. For example, the compressor-distractor may be used during a procedure in which a bone preparation guide is also deployed for preparing the bones that are to be subsequent distracted and/or compressed together using the compressor-distractor. The bone preparation guide may be pinned to two different bone portions, which may be two different bones separated by a joint or two portions of the same bone (e.g., separated by a fracture or break). In either case, one end of the bone preparation guide may be pinned to one bone portion while another end of the bone preparation guide may be pinned to the other bone portion. The bone preparation guide may be pinned to the two bone portions using a pair of pins that extend parallel to each other through a pair of fixation apertures on the bone preparation guide, optionally along with one or more additional pins that may extend through one or more additional fixation apertures on the bone preparation guide that may be skewed or angled at a non-zero degree angle relative to the parallel pins. In some configurations, the bone preparation guide defines one or more slots through which a bone preparation instrument (e.g., cutting instrument) is inserted to prepare opposed end faces of the two bones.

After utilizing the bone preparation guide to prepare the two bone portions, the clinician may remove any angled pins (e.g., non-parallel pins) inserted through the bone preparation guide into the bone portions, leaving the parallel-aligned pins (e.g., a pair of parallel pins) in the bone portions. The bone preparation guide can be slide or translated along the parallel-aligned pins until the fixation apertures of the bone preparation guide come off the distal ends of the pins. At this point, the bone preparation guide may be separated from the pins, leaving the pins in the bone portions. The compressor-distractor can then be installed over the pins by threading the parallel-aligned pins through the pin-receiving holes of the compressor-distractor. For example, the clinician can select an orientation of the reversible compressor-distractor based on the foot being operated on and guide a pin inserted into one bone portion through a pin-receiving hole associated with the selected orientation. The clinician can also guide a pin inserted into the second bone portion through another pin-receiving hole of the compressor-distractor.

When the pin-receiving holes of the compressor-distractor are angled relative to each other, the process of installing the compressor-distractor on the pins will cause the pins to move. In particular, the pins may move from being substantially parallel-aligned to each other to a position in which the pins are angled relative to each other at a non-zero degree angle defined by the compressor-distractor in one or more planes, such as two or more planes. As a result, the first and second bone portions in which the pins are inserted may move a distance corresponding to the angular movement of the pins.

After installing the compressor-distractor on the pins, the clinician may actuate the actuator to move the first and second engagement arms away from each other and, as a result, move the bone portions away from each other. This can provide an enlarged separation gap between the bone portions for cleaning the inter-bone space in anticipation for fixation. For example, the clinician may remove bone chips and/or tissue debris from the inter-bone space between the two bone portions, further cut or prepare an end face of one or both bone portions, or otherwise prepare for fixation. The clinician may additionally or alternatively actuate the actuator to move the first and second engagement arms toward each other and, as a result, move the bone portions toward each other. The clinician may move the first and second engagement arms toward each other until the end faces of the bone portions are pressing against each other, resulting in a compressive force being applied to the bone portions. In some example, the clinician then fixates the bone portions by applying one or more fixation members to the bone portions.

In one example, a reversible compressor-distractor is described that includes a first engagement arm, a second engagement arm, and an actuator. The first engagement arm can include a first side pin-receiving hole for receiving a first pin inserted into a first bone portion; and a second side pin-receiving hole for receiving the first pin inserted into the first bone portion. The second side pin-receiving hole can be positioned on an opposite lengthwise side of the first engagement arm than the first side pin-receiving hole. The second engagement arm can include a pin-receiving hole for receiving a second pin inserted into a second bone portion. The actuator can be operatively coupled to the first engagement arm and the second engagement arm and configured to move the first engagement arm and the second engagement arm each other to move the first bone portion toward the second bone portion.

In another example, a method is described that includes inserting a first pin into a first bone portion and a second pin into a second bone portion. The method also includes selecting one of two different available orientations for a compressor-distractor, where the compressor-distractor includes a first engagement arm having a first side pin-receiving hole for use in a first one of the two different available orientations and a second side pin-receiving hole for use in a second one of the two different available orientations. The compressor-distractor also includes a second engagement arm having a pin-receiving hole. The method also involves inserting the compressor-distractor on the first pin by at least positioning the first pin through either the first side pin-receiving hole or the second side pin-receiving hole of the first engagement arm and inserting the second pin through the pin-receiving hole of the second engagement arm.

The details of one or more examples are set forth in the accompanying drawings and the description below. Other features, objects, and advantages will be apparent from the description and drawings, and from the claims.

The details of one or more examples are set forth in the accompanying drawings and the description below. Other features, objects, and advantages will be apparent from the description and drawings, and from the claims.

DETAILED DESCRIPTION

In general, the present disclosure is directed to devices and techniques for correcting a misalignment of one or more bones. The disclosed devices and techniques can be implemented in a surgical procedure in which one bone portion is realigned relative to another bone portion. In some examples, the technique is performed on one or more bones in the foot or hand, where bones are relatively small compared to bones in other parts of the human anatomy. For example, the foregoing description generally refers to example techniques performed on the foot and, more particularly a metatarsal and cuneiform of the foot. However, the disclosed techniques may be performed on other bones. In various examples, the devices and/or techniques of the disclosure may be utilized on comparatively small bones in the foot such as a metatarsal (e.g., first, second, third, fourth, or fifth metatarsal), a cuneiform (e.g., medial, intermediate, lateral), a cuboid, a phalanx (e.g., proximal, intermediate, distal), and/or combinations thereof. The bones may be separated from each other by a tarsometatarsal ("TMT") joint, a metatarsophalangeal ("MTP") joint, or other joint. Accordingly, reference to a metatarsal and cuneiform herein may be replaced with other bone pairs.

Figure 1B:
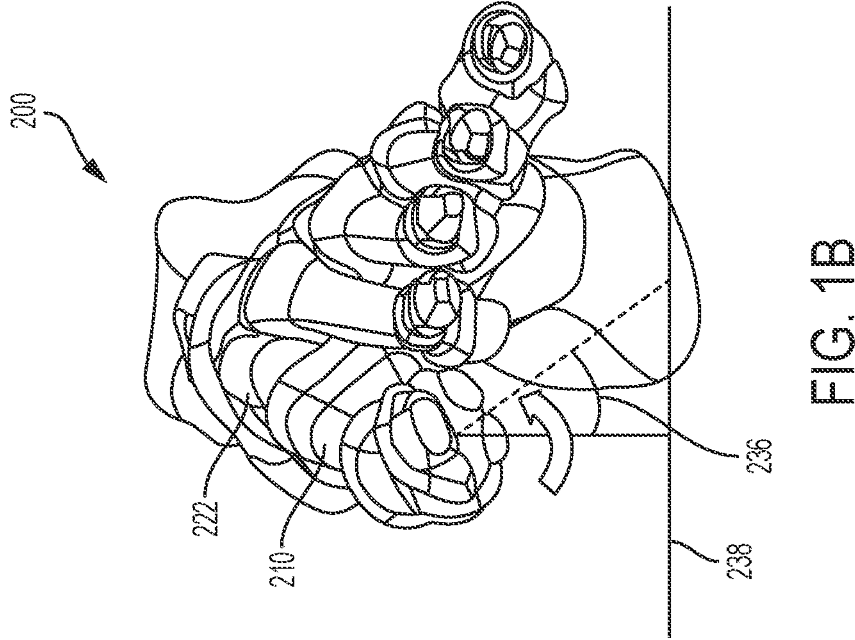
FIGS. 1A and 1B are front views of a foot showing a normal first metatarsal position and an example frontal plane rotational misalignment position, respectively.
Figure 1A:
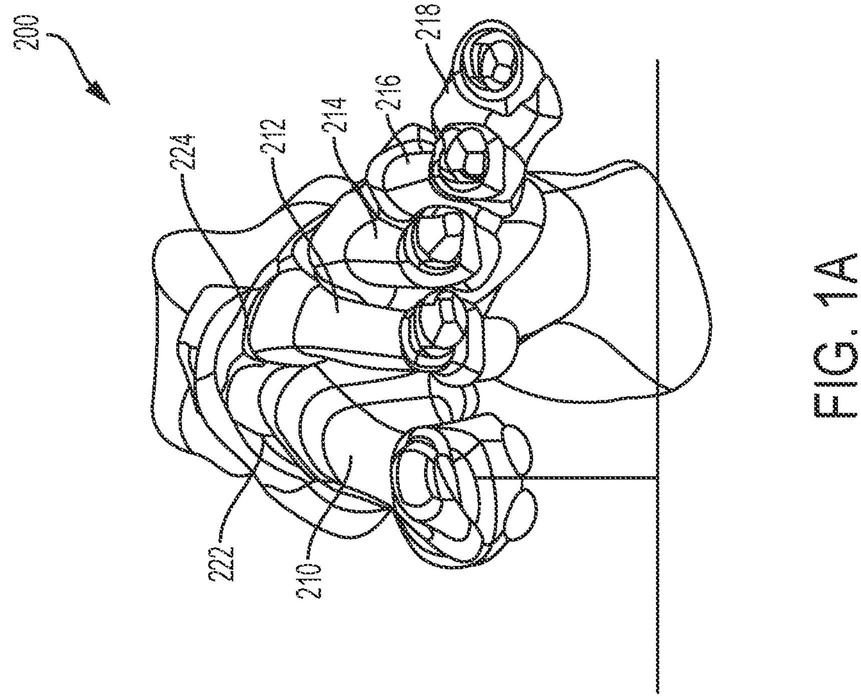
Figure 2B:
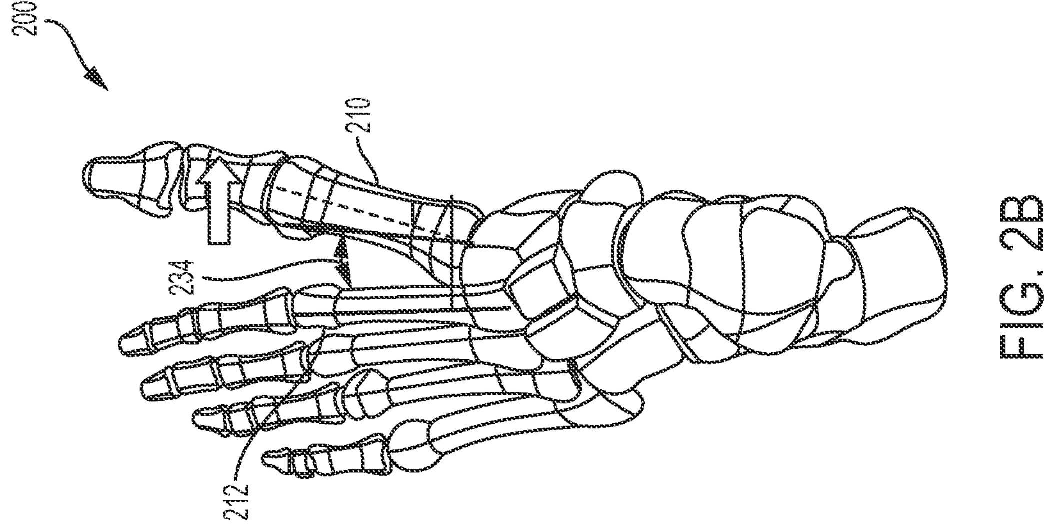
FIGS. 2A and 2B are top views of a foot showing a normal first metatarsal position and an example transverse plane misalignment position, respectively.
Figure 2A:
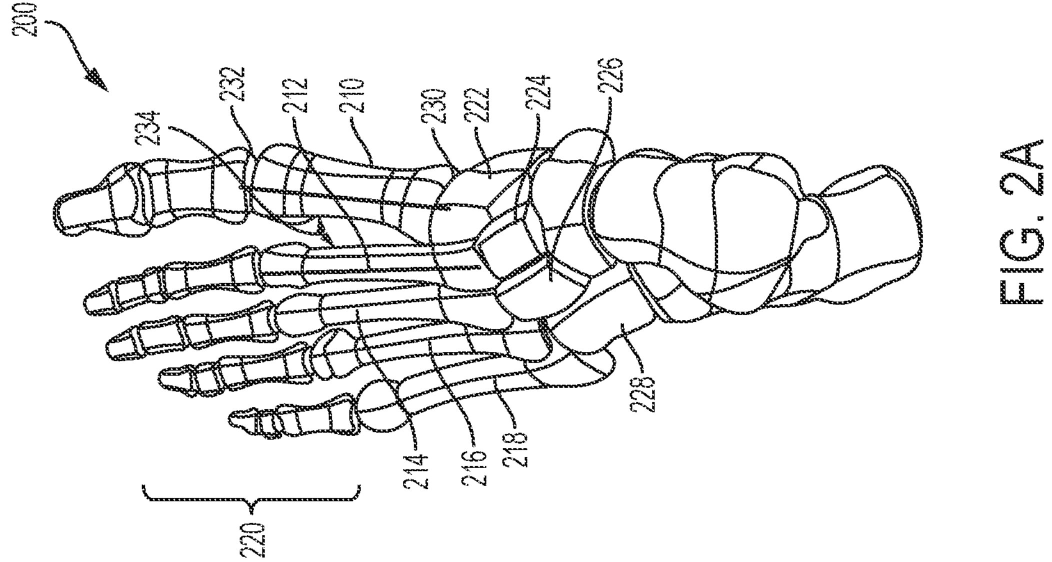
Figures 3A, 3B:
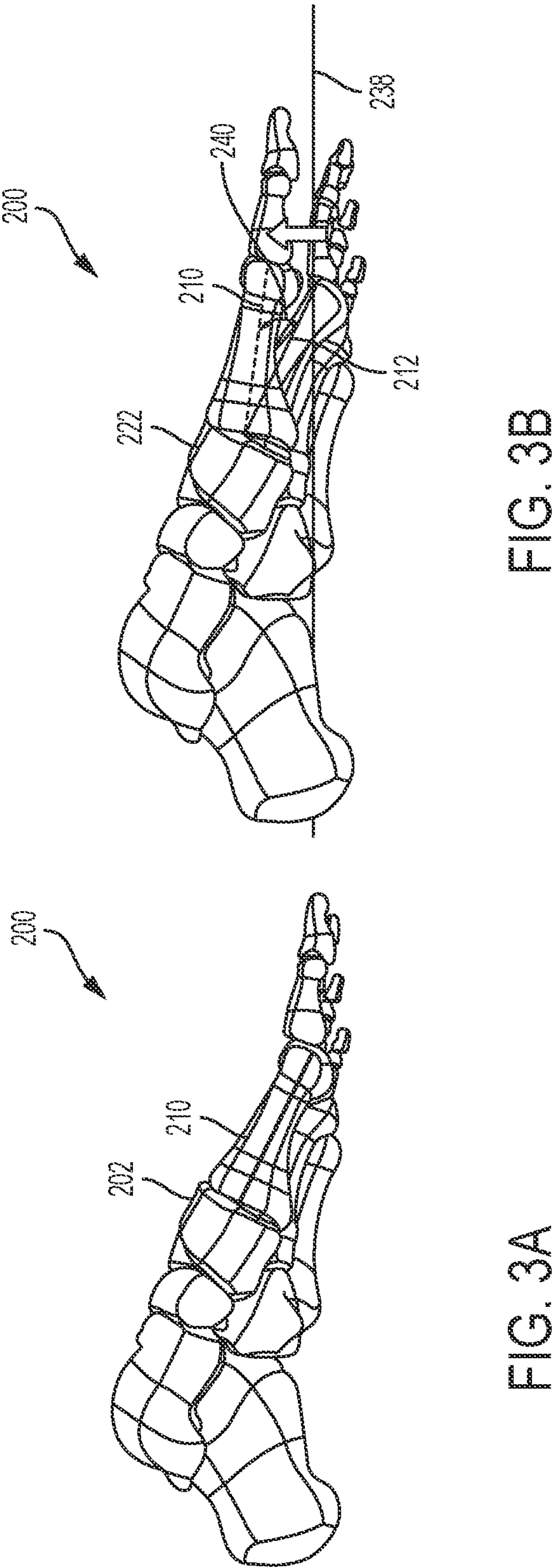
FIGS. 3A and 3B are side views of a foot showing a normal first metatarsal position and an example sagittal plane misalignment position, respectively.

FIGS. 1-3 are different views of a foot 200 showing example anatomical misalignments that may occur and be corrected according to the present disclosure. Such misalignment may be caused by a hallux valgus (bunion), natural growth deformity, or other condition causing anatomical misalignment. FIGS. 1A and 1B are front views of foot 200 showing a normal first metatarsal position and an example frontal plane rotational misalignment position, respectively. FIGS. 2A and 2B are top views of foot 200 showing a normal first metatarsal position and an example transverse plane misalignment position, respectively. FIGS. 3A and 3B are side views of foot 200 showing a normal first metatarsal position and an example sagittal plane misalignment position, respectively. While FIGS. 1B, 2B, and 3B show each respective planar misalignment in isolation, in practice, a metatarsal may be misaligned in any two of the three planes or even all three planes. Accordingly, it should be appreciated that the depiction of a single plane misalignment in each of FIGS. 1B, 2B, and 3B is for purposes of illustration and a metatarsal may be misaligned in multiple planes that is desirably corrected.

With reference to FIGS. 1A and 2A, foot 200 is composed of multiple bones including a first metatarsal 210, a second metatarsal 212, a third metatarsal 214, a fourth metatarsal 216, and a fifth metatarsal 218. The metatarsals are connected distally to phalanges 220 and, more particularly, each to a respective proximal phalanx. The first metatarsal 210 is connected proximally to a medial cuneiform 222, while the second metatarsal 212 is connected proximally to an intermediate cuneiform 224 and the third metatarsal is connected proximally to lateral cuneiform 226. The fourth and fifth metatarsals 216, 218 are connected proximally to the cuboid bone 228. The joint 230 between a metatarsal and respective cuneiform (e.g., first metatarsal 210 and medial cuneiform 222) is referred to as the tarsometatarsal ("TMT") joint. The joint 232 between a metatarsal and respective proximal phalanx is referred to as a metatarsophalangeal joint. The angle 234 between adjacent metatarsals (e.g., first metatarsal 210 and second metatarsal 212) is referred to as the intermetatarsal angle ("IMA").

As noted, FIG. 1A is a frontal plane view of foot 200 showing a typical position for first metatarsal 210. The frontal plane, which is also known as the coronal plane, is generally considered any vertical plane that divides the body into anterior and posterior sections. On foot 200, the frontal plane is a plane that extends vertically and is perpendicular to an axis extending proximally to distally along the length of the foot. FIG. 1A shows first metatarsal 210 in a typical rotational position in the frontal plane. FIG. 1B shows first metatarsal 210 with a frontal plane rotational deformity characterized by a rotational angle 236 relative to ground, as indicated by line 238.

FIG. 2A is a top view of foot 200 showing a typical position of first metatarsal 210 in the transverse plane. The transverse plane, which is also known as the horizontal plane, axial plane, or transaxial plane, is considered any plane that divides the body into superior and inferior parts. On foot 200, the transverse plane is a plane that extends horizontally and is perpendicular to an axis extending dorsally to plantarly (top to bottom) across the foot. FIG. 2A shows first metatarsal 210 with a typical IMA 234 in the transverse plane. FIG. 2B shows first metatarsal 210 with a transverse plane rotational deformity characterized by a greater IMA caused by the distal end of first metatarsal 210 being pivoted medially relative to the second metatarsal 212.

FIG. 3A is a side view of foot 200 showing a typical position of first metatarsal 210 in the sagittal plane. The sagittal plane is a plane parallel to the sagittal suture which divides the body into right and left halves. On foot 200, the sagittal plane is a plane that extends vertically and is perpendicular to an axis extending proximally to distally along the length of the foot. FIG. 3A shows first metatarsal 210 with a typical rotational position in the sagittal plane. FIG. 3B shows first metatarsal 210 with a sagittal plane rotational deformity characterized by a rotational angle 240 relative to ground, as indicated by line 238.

A reversible compressor-distractor according to the disclosure can be useful during a bone positioning procedure to correct an anatomical misalignment of a bones or bones. In some applications, the reversible compressor-distractor can help establish and/or maintain a realignment between a metatarsal and an adjacent cuneiform. The metatarsal undergoing realignment may be anatomically misaligned in the frontal plane, transverse plane, and/or sagittal plane, as illustrated and discussed with respect to FIGS. 1-3 above. Accordingly, realignment may involve releasing the misaligned metatarsal for realignment and thereafter realigning the metatarsal in one or more planes, two or more planes, or all three planes. After suitably realigning the metatarsal, the metatarsal can be fixated to hold and maintain the realigned positioned.

While a metatarsal can have a variety of anatomically aligned and misaligned positions, in some examples, the term "anatomically aligned position" means that an angle of a long axis of first metatarsal 210 relative to the long axis of second metatarsal 212 is about 10 degrees or less (e.g., 9 degrees or less) in the transverse plane and/or sagittal plane. In certain embodiments, anatomical misalignment can be corrected in both the transverse plane and the frontal plane. In the transverse plane, a normal IMA 234 between first metatarsal 210 and second metatarsal 212 is less than about 9 degrees. An IMA 234 of between about 9 degrees and about 13 degrees is considered a mild misalignment of the first metatarsal and the second metatarsal. An IMA 234 of greater than about 16 degrees is considered a severe misalignment of the first metatarsal and the second metatarsal. In some embodiments, methods and/or devices according to the disclosure are utilized to anatomically align first metatarsal 210 by reducing the IMA from over 10 degrees to about 10 degrees or less (e.g., to an IMA of 9 degrees or less, or an IMA of about 1-5 degrees), including to negative angles of about −5 degrees or until interference with the second metatarsal, by positioning the first metatarsal at a different angle with respect to the second metatarsal.

With respect to the frontal plane, a normal first metatarsal will be positioned such that its crista prominence is generally perpendicular to the ground and/or its sesamoid bones are generally parallel to the ground and positioned under the metatarsal. This position can be defined as a metatarsal rotation of 0 degrees. In a misaligned first metatarsal, the metatarsal may be axially rotated between about 4 degrees to about 30 degrees or more. In some embodiments, methods and/or devices according to the disclosure are utilized to anatomically align the metatarsal by reducing the metatarsal rotation from about 4 degrees or more to less than 4 degrees (e.g., to about 0 to 2 degrees) by rotating the metatarsal with respect to the adjacent cuneiform.

A reversible compressor-distractor according to the disclosure may be useful to distract a misaligned metatarsal from an adjacent cuneiform to provide access to the end faces of the bones and/or tarsometatarsal joint. The reversible compressor-distractor may also be useful to apply a compressive force to the metatarsal and adjacent cuneiform (e.g., after preparing the end faces of the bones) to press the bones together to facilitate fixation. Additionally or alternatively, the reversible compressor-distractor may impart and/or maintain relative movement between the metatarsal and adjacent cuneiform, such as rotation and/or pivoting of one bone relative to the other bone. For example, an angular offset provided by pin-receiving holes of the reversible compressor-distractor may be effective to move the metatarsal from an anatomically misaligned position to an anatomically aligned position. As the reversible compressor-distractor is translated over pins inserted into the metatarsal and cuneiform, the angular offset of the pin-receiving holes may cause the pins to move from being generally parallel to an angular alignment dictated by the pin-receiving holes. The resulting movement of the metatarsal relative to cuneiform caused by this movement can help position the metatarsal in an aligned position.

In some examples, the reversible compressor-distractor is configured to be interchangeably used on right and left feet by reversing the orientation of the compressor-distractor. For example, the compressor-distractor may include a first engagement arm having at least two oppositely orientated pin-receiving holes on different sides of the engagement arm. The compressor-distractor may also include a second engagement arm having at least one pin-receiving hole. In use, the clinician can select an orientation of the compressor-distractor and engage pin-receiving holes associated with the selected orientation.

Figures 4A, 4B:
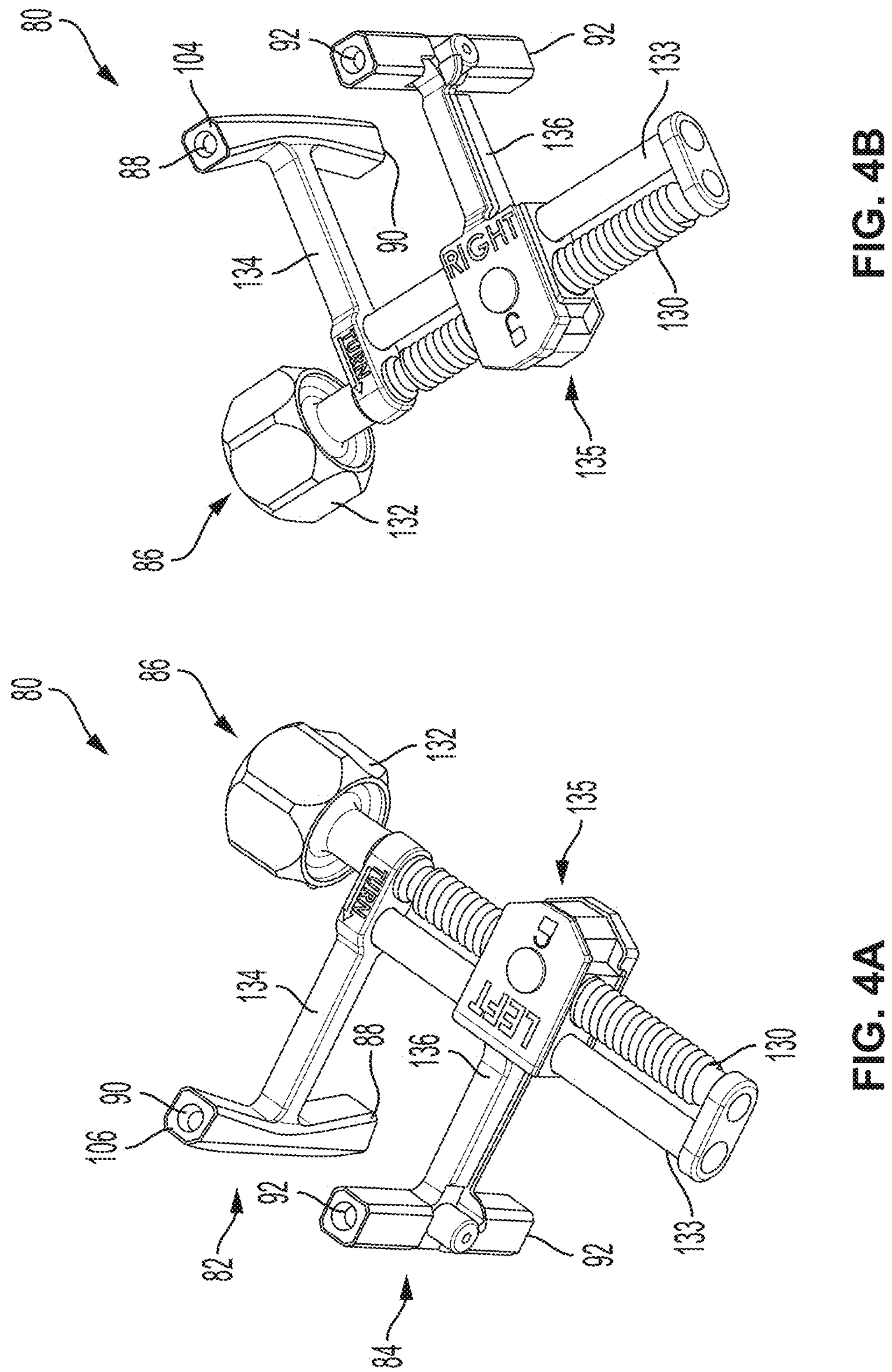
FIGS. 4A and 4B are perspective views of an example reversible compressor-distractor according to disclosure.

FIGS. 4A and 4B (collectively referred to as "FIG. 4") are perspective views of an example reversible compressor-distractor 80 according to disclosure. FIG. 4A illustrates compressor-distractor 80 in a first orientation in which a first side of the compressor-distractor (labeled left side on the example device) is facing upward (e.g., plantarly) and a second side of the compressor-distractor (labeled right side on the example device) is facing downward (e.g., dorsally). FIG. 4B illustrates compressor-distractor 80 and a second orientation in which the compressor-distractor has been flipped 180° relative to the position in FIG. 4A. In particular, in FIG. 4B, compressor-distractor 80 is positioned so that side facing downward in FIG. 4A is positioned upward in FIG. 4B and, correspondingly, the side facing upward in FIG. 4A is facing downward in FIG. 4B.

In the example of FIG. 4, compressor-distractor 80 is illustrated as having a first engagement arm 82 and a second engagement arm 84. Compressor-distractor 80 also includes an actuator 86 that is operably coupled to the first engagement arm 82 and the second engagement arm 84. Actuator 86 can be actuated to move the two engagement arms toward each other and away from each other to adjust a separation distance between the two arms. As will be discussed in greater detail, each engagement arm includes at least one pin-receiving hole that is configured to receive a pin inserted into a bone. Further, the orientation of compressor-distractor 80 may be reversed from an orientation in which an end of the first engagement arm 82 and an end of the second engagement arm 84 are positioned plantarly (with the opposite end positioned dorsally) to a flipped orientation in which the end of the first engagement arm and the end of the second engagement arm are positioned dorsally (with the opposite end positioned plantarly).

For example, first engagement arm 82 may include a first side pin-receiving hole 88 on a first side of the engagement arm (FIG. 4A) and a second side pin-receiving hole 90 on a second side of the engagement arm (FIG. 4B). Second engagement arm 84 can include one or more pin-receiving holes 92 which, in the illustrated example, is shown as a single pin-receiving hole extending from the first side of compressor-distractor 80 to the second side of compressor-distractor 80. In use, a first pin can be received in the first side pin-receiving hole 88 when compressor-distractor 80 is in a first orientation or, alternatively, the first pin can be received in the second side pin-receiving hole 90 when the compressor-distractor is in a second orientation. The pin-receiving hole 92 defined by second engagement arm 84 can receive a second pin in both the first orientation and the second orientation of compressor-distractor 80.

Figure 5A:
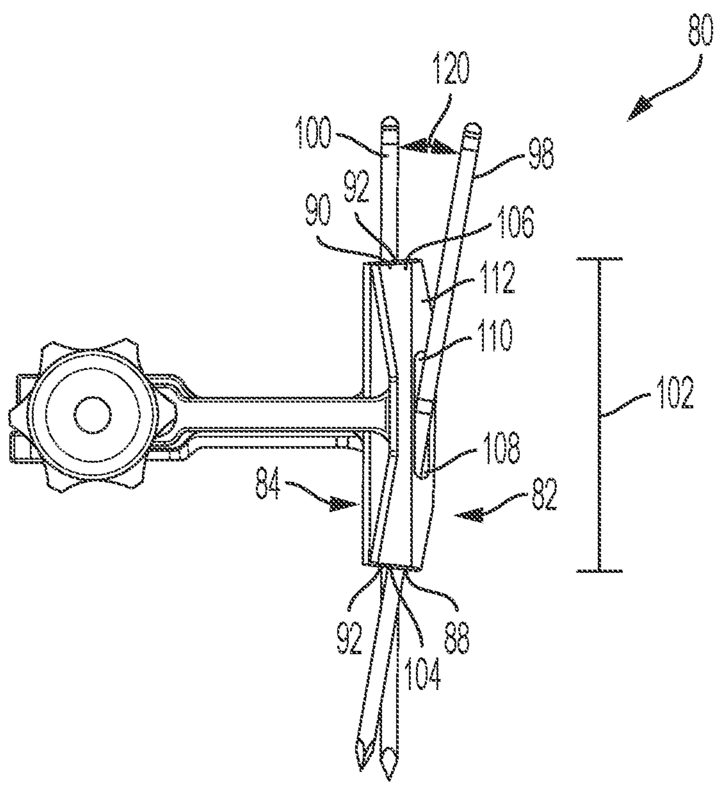
FIGS. 5A and 5B are frontal plane side views of the example reversible compressor-distractor of FIGS. 4A and 4B.
Figure 5B:
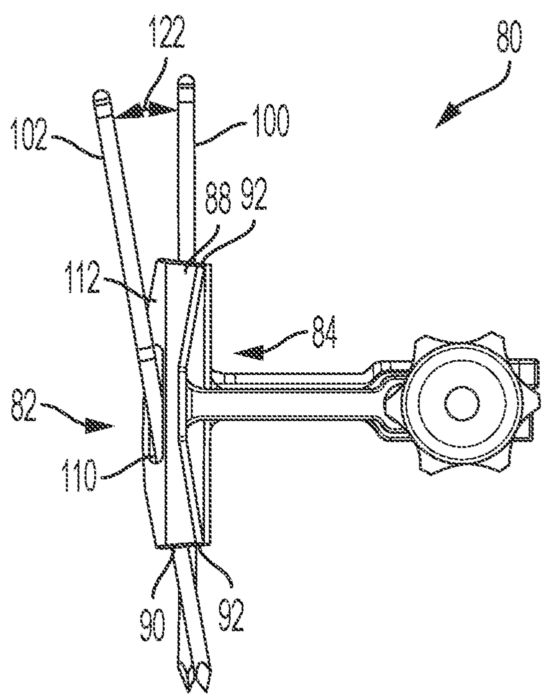
Figure 6A:
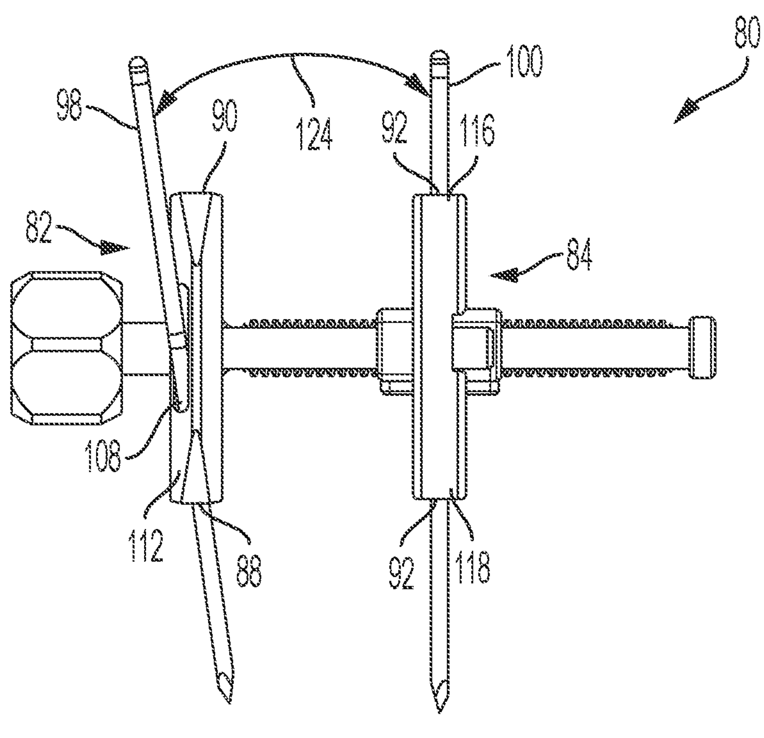
FIGS. 6A and 6B are transverse plane side views of the example reversible compressor-distractor shown in FIGS. 5A and 5B.
Figure 6B:
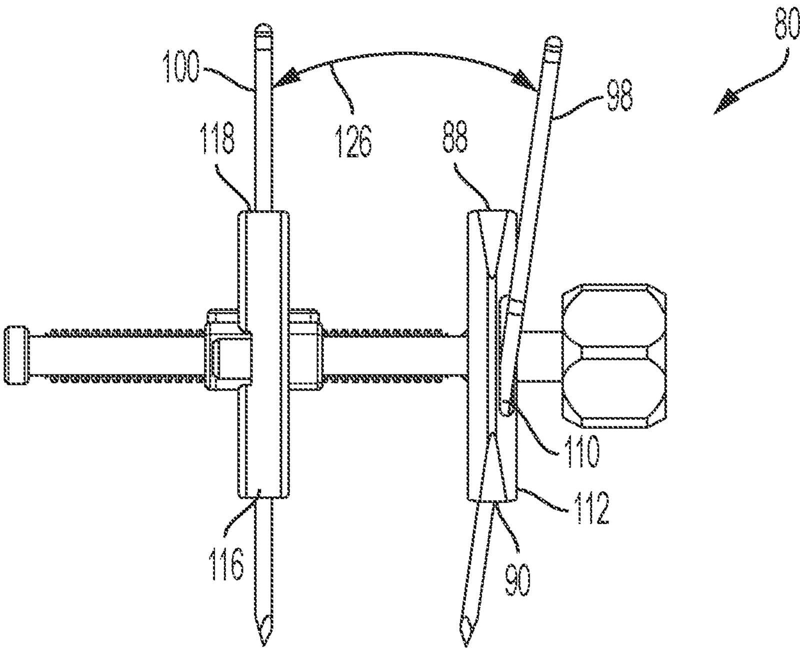

FIGS. 5A and 5B (collectively referred to as "FIG. 5") are frontal plane side views of example configuration of compressor-distractor 80 illustrating the compressor-distractor engaged with a first pin 98 and a second pin 100. FIGS. 6A and 6B (collectively referred to as "FIG. 6") are transverse plane side views of the example configuration of compressor-distractor 80 shown in FIGS. 5A and 5B, respectively. FIGS. 5A and 6A illustrate compressor-distractor 80 in a first orientation as shown in the perspective view of FIG. 4A. FIGS. 5B and 6B illustrate compressor-distractor 80 and a second orientation as shown in the perspective view of FIG. 4B. Compressor-distractor 80 has been flipped or rotated 180° about the length of the compressor-distractor between the example first orientation in the example second orientation illustrated in the figures.

As illustrated in the example of FIGS. 5 and 6, first side pin-receiving hole 88 and second side pin-receiving hole 90 of first engagement arm 82 can provide different pin-receiving hole options on opposite lengthwise extents of first engagement arm 82. For example, first engagement arm 82 can have a length 102 extending from a first end 104 of the first engagement arm to a second end 106 of the first engagement arm. First side pin-receiving hole 88 can be accessed from a first side (e.g., downward or dorsal side) of compressor-distractor 80, when the compressor-distractor is in a first orientation. First side pin-receiving hole 88 can provide a cavity extending at least partially along the length 102 of first engagement arm 82 that is configured to receive first pin 98, when compressor-distractor 80 is in a first orientation. Second side pin-receiving hole 90 can be accessed from a second side (e.g., downward or dorsal side) of compressor-distractor 80, when the compressor-distractor is in a second orientation. Second side pin-receiving hole 90 can also provide a cavity extending at least partially along the length 102 of first engagement arm 82 that is configured to receive first pin 98.

When compressor-distractor 80 is positioned in a first orientation (e.g., with first side pin-receiving hole 88 accessible from the bottom or dorsal side), second side pin-receiving hole 90 may be positioned on a second side (e.g., upward facing or plantar side) of compressor-distractor 80 and remain unused during the procedure. Similarly, when compressor-distractor 80 is inverted to be positioned in a second orientation (e.g., with second side pin-receiving hole 90 accessible from the bottom or dorsal side), first side pin-receiving hole 88 may be positioned on a first side (e.g., upward facing or plantar side) of compressor-distractor 80 and remain unused during the procedure. In this way, first engagement arm 82 of compressor-distractor 80 may provide at least two different pin-receiving holes accessible on different sides of the engagement arm, with the different pin-receiving holes being selectively used depending on the orientation of the compressor-distractor.

Each pin-receiving hole of compressor-distractor 80 can define an entrance opening through which an end of the pin enters the hole and an exit opening through which the end of the pin exits the hole after having traversed through a portion of the engagement arm defining the pin-receiving hole. In the illustrated arrangement, first side pin-receiving hole 88 is shown as defining an opening extending through the first end 104 of first engagement arm 82. Second side pin-receiving hole 90 is shown as defining an opening extending through the second end 106 of first engagement arm 82. The opening of first side pin-receiving hole 88 at the first end 104 of first engagement arm 82 may define a pin entry location in which first pin 98 enters the pin-receiving hole (e.g., when in the first orientation). The opening of second side pin-receiving hole 90 at the second end 106 of first engagement arm 82 may define a pin entry location in which first pin 98 enters the pin-receiving hole (e.g., when in the second orientation). Each of first side pin-receiving hole 88 and second side pin-receiving hole 90 may define a corresponding pin exit location.

For example, with reference to FIGS. 5 and 6, first side pin-receiving hole 88 of first engagement arm 82 can define a first pin exit 108. Second side pin-receiving hole 90 of first engagement arm 82 can define a second pin exit 110. First side pin-receiving hole 88 can define a linear pathway extending through first engagement arm 82 from the opening at the first end 104 of first engagement arm 82 to first pin exit 108. Second side pin-receiving hole 90 can define a linear pathway extending through first engagement arm 82 from the opening at the second end 106 of first engagement arm to second pin exit 110.

In the illustrated configuration, at least one pin-receiving hole of first engagement arm 82 extends through a sidewall of the engagement arm. For example, first engagement arm 82 can define at least one sidewall 112 forming a side surface of the engagement arm. First side pin-receiving hole 88 and/or second side pin-receiving hole 90 can extend through the sidewall 112. In the illustrated configuration, for example, first pin exit 108 of first side pin-receiving hole 88 and second pin exit 110 of second side pin-receiving hole 90 each extend through sidewall 112. First pin exit 108 and second pin exit 110 are shown extending through sidewall 112 at a same location about the perimeter of first engagement arm 82 (e.g., same radial location) but, in different examples, can be angularly offset from each other about the perimeter of the engagement arm.

Accordingly, first pin exit 108 can extend through the sidewall 112 of first engagement arm 82 at a first location, and second pin exit 110 can extend through the sidewall 112 of first engagement arm 82 at a second location. The first location can be offset along the length 102 of first engagement arm 82 from the second location. In some configurations, first side pin-receiving hole 88 does not intersect second side pin-receiving hole 90. In other configurations, first side pin-receiving hole 88 may intersect second side pin-receiving hole 90 (e.g., within the body of first engagement arm 82 or along an outer side surface of the first engagement arm beyond where each respective pin engagement hole exit sidewall 112.

For example, first side pin-receiving hole 88 can define a first longitudinal axis (e.g., shown by first pin 98 inserted through the first side pin-receiving hole in FIGS. 5A and 6A). Second side pin-receiving hole 90 can define a second longitudinal axis (e.g., shown by first pin 98 inserted through the second side pin-receiving hole in FIGS. 5B and 6B). The first longitudinal axis defined by first side pin-receiving hole 88 can intersect the second longitudinal axis defined by second side pin-receiving hole 90. Reference to a longitudinal axis is intended to refer to an axis extending along a length of a pin-receiving hole without necessitating any particular orientation relative to the length 102 of first engagement arm 82.

As briefly discussed above, second engagement arm 84 can also define a pin-receiving hole. Second engagement arm 84 may define multiple pin-receiving holes and can be configured with any of the pin-receiving configurations described herein in connection with first engagement arm 82. However, in the illustrated configuration, second engagement arm 84 is shown as having a single pin-receiving hole 92. Pin-receiving hole 92 can be oriented in a number of different ways relative to the length of second engagement arm 84. In the illustrated configuration, pin-receiving hole 92 extends parallel to (e.g., co-linear with) the length of second engagement arm 84.

For example, as seen in FIG. 6, second engagement arm 84 can have a length 114 extending from a first end 116 to a second end 118. The pin-receiving hole defined by second engagement arm 84 can extend through the first end 116 of the second engagement arm and through the second end 118 of the engagement arm. When compressor-distractor 80 is used in the first orientation, an opening at the first end 116 of second engagement arm 84 can define a pin entry location in which an end of second pin 100 enters the second engagement arm. In this orientation, an opening at the second end 118 of second engagement arm 84 can define a pin exit where the end of second pin 100 exits the second engagement arm. By contrast, when compressor-distractor 80 is used in the second orientation, the opening at the second end 118 of second engagement arm 84 can define the pin entry location, and the opening at the first end 116 of the second engagement arm can define the pin exit location.

During use, a selected one of first side pin-receiving hole 88 and second side pin-receiving hole 90 of first pin engagement arm 82 can receive first pin 98. In addition, the pin-receiving hole 92 defined by second engagement arm 84 can receive second pin 100. The first pin 98 and second pin 100 can be inserted into different bones or bone portions being worked upon. In the case of a bone realignment procedure, for example, first pin 98 can be inserted into a metatarsal (e.g., first metatarsal 210) and second pin 100 can be inserted into a cuneiform (e.g., medial cuneiform 222). The pin-receiving holes can anchor compressor-distractor 80 to the bones being compressed and/or distracted via the pins inserted through the holes and into the underlying bones. Additionally or alternatively, the pin-receiving holes can be used to impart relative movement between one bone in which first pin 98 is inserted and another bone in which second pin 100 is inserted.

For example, first side pin-receiving hole 88 and second side pin-receiving hole 90 may each be angled relative to one or more pin-receiving holes 92 defined by second engagement arm 84. The pin-receiving holes can be angled relative to each other at a non-zero degree angle such that, when compressor-distractor 80 is inserted over first and second pins 98, 100 (which may be a substantially parallel set of pins), the angled receiving holes causes the pins to move relative to each other to align with the pin-receiving holes. The direction and extent of movement imposed by the angled pin-receiving holes of compressor-distractor 80 may vary depending on the desired surgical application in which the compressor-distractor is being used. In the case of a misaligned metatarsal, such as a bunion procedure for instance, the pin-receiving holes may be angled to impart a frontal plane rotation and/or a sagittal plane translation. As a result, when compressor-distractor 80 is installed over pins position in the metatarsal and adjacent cuneiform, the angled pin-receiving holes may cause the metatarsal to rotate in the frontal plane relative to the cuneiform and/or translate in the sagittal plane (e.g., downwardly or plantarly) to help correct a misalignment of the metatarsal.

As discussed above, first side pin-receiving hole 88 can define a first longitudinal axis and second side pin-receiving hole 90 can define a second longitudinal axis. In addition, the pin-receiving hole 92 through second engagement arm 84 can define a third longitudinal axis (e.g., shown by second pin 100 inserted through the pin-receiving hole in FIGS. 5 and 6). The first longitudinal axis defined by first side pin-receiving hole 88 and/or the second longitudinal axis defined by second side pin-receiving hole 90 can be angled relative to the third longitudinal axis defined by pin-receiving hole 92 and one or more planes, such as in two or more planes. For example, the first longitudinal axis defined by first side pin-receiving hole 88 can be angled relative to the third longitudinal axis defined by pin-receiving hole 92 in one or both of a frontal plane and a sagittal plane. The second longitudinal axis defined by second side pin-receiving hole 90 can be angled relative to the third longitudinal axis defined by pin-receiving hole 92 in one or both of the frontal plane and the sagittal plane. In some configurations, either the first longitudinal axis or the second longitudinal axis is not angled relative to the third longitudinal axis but, instead, is parallel to the third longitudinal axis.

FIG. 5 illustrates example frontal plane angular offsets between the first longitudinal axis defined by first side pin-receiving hole 88 and the third longitudinal axis defined by pin-receiving hole 92 as well as between the second longitudinal axis defined by second side pin-receiving hole 90 and the third longitudinal axis defined by pin-receiving hole 92. In this example, the first longitudinal axis defined by first side pin-receiving hole 88 is angled relative to the third longitudinal axis defined by pin-receiving hole 92 in the frontal plane by an angle 120. The second longitudinal axis defined by second side pin-receiving hole 90 is angled relative to the third longitudinal axis defined by pin-receiving hole 92 in the frontal plane by an angle 122. While angles 120 and 122 may vary, in some examples, each angle may range from 2° to 20°, such as from 6° to 15°, or from 8° to 12°, or approximately 10°. The respective longitudinal axes may be offset in a direction that causes the metatarsal to rotate laterally as the compressor-distractor 80 is installed over first and second pins 98, 100. For example, when compressor-distractor 80 is positioned on the medial side of the foot, the relative frontal plane angulation between the pin-receiving holes may cause first pin 98 to rotate toward the lateral side of the foot relative to second pin 100.

In addition to or in lieu of providing a fontal plane angulation, compressor-distractor 80 may be configured to impart sagittal plane rotation, when the compressor-distractor 80 is installed over first and second pins 98, 100. For example, when installed over first and second pins 98, 100 positioned in the metatarsal and cuneiform (e.g., substantially parallel pins), the relative angulation of the pin-receiving holes may cause the metatarsal to rotate or flex plantarly (e.g., such that the distal end of the metatarsal is rotated plantarly about the TMT joint).

FIG. 6 illustrates example sagittal plane offsets between the first longitudinal axis defined by first side pin-receiving hole 88 and the third longitudinal axis defined by pin-receiving hole 92 as well as between the second longitudinal axis defined by second side pin-receiving hole 90 and the third longitudinal axis defined by pin-receiving hole 92. In this example, the first longitudinal axis defined by first side pin-receiving hole 88 is angled relative to the third longitudinal axis defined by pin-receiving hole 92 in the sagittal plane by an angle 124. The second longitudinal axis defined by second side pin-receiving hole 90 is angled relative to the third longitudinal axis defined by pin-receiving hole 92 in the sagittal plane by an angle 126. While angles 124, 126 may vary, in some examples, each angle may range from 2° to 12°, such as from 5° to 9°, or from 6° to 8°, or approximately 7°. The pin-receiving holes may be offset relative to each other in a direction that causes the metatarsal to rotate (e.g., downwardly or plantarly) in the sagittal plane as the compressor-distractor 80 is installed over first and second pins 98, 100.

First side pin-receiving hole 88 may define a same relative angle or angles, 120, 124 relative to pin-receiving hole 92 as the angle or angles 122, 124 defined between the second side pin-receiving hole 90 in pin-receiving hole 92. For example, one or more angles defined between the first longitudinal axis and the third longitudinal axis may be equal and opposite to one or more corresponding angles defined between the second longitudinal axis and the third longitudinal axis. When so configured, first side pin-receiving hole 88 and second side pin-receiving hole 90 may define a mirrored relationship with respect to each other. In other words, the angular relationship between first side pin-receiving hole 88 and pin-receiving hole 92 may be the same as the angular relationship between second side pin-receiving hole 90 in pin-receiving hole 92. This can configure first side pin-receiving hole 88 and second side pin-receiving hole 90 to provide the same angular relationship with pin-receiving hole 92 when compressor-distractor 80 is a reverse between the first and second orientations. In other configurations, however, first side pin-receiving hole 88 may have one or more different angles relative to pin-receiving hole 92 in the one or more corresponding angles defined between second side pin-receiving hole 90 in pin-receiving hole 92.

In general, features described as pin-receiving holes may be void spaces extending through a portion of compressor-distractor 80 and configured (e.g., sized and/or shaped) to pass a pin inserted into a bone therethrough. While the pin-receiving holes may have any polygonal (e.g., square, rectangle) or arcuate (e.g., curved, elliptical) shape, the pin-receiving holes may typically have a circular cross-sectional shape. In some examples, the pin-receiving holes have a diameter ranging from 0.1 mm to 10 mm, such as from 0.5 mm to 4 mm. The pin-receiving holes may have a length (e.g., extending through the thickness of first engagement arm 82 or second engagement arm 84) ranging from 5 mm to 50 mm, such as from 10 mm to 25 mm.

As briefly discussed above in connection with FIG. 4, compressor-distractor 80 can open and close to compress and distract the bones to which to the compressor-distractor is secured. To facilitate movement, compressor-distractor 80 is illustrated as having an actuator 86. Actuator 86 is configured to control movement of first engagement arm 82 relative to second engagement arm 84. Actuator 86 may be implemented using any feature that provides controllable relative movement between the two engagement arms, such as rotary movement, sliding movement, or other relative translation. In some configurations, actuator 86 is configured to move first and second engagement arms 82, 84 at least 1 mm away from each other, such as a distance ranging from 1 mm to 45 mm, a distance ranging from 1 mm to 5 mm, or a distance ranging from 1 mm to 2.5 mm during distraction. Actuator 86 may be actuated during compression until the faces of the bones to which compressor-distractor 80 is attached are suitably compressed and/or the sidewall faces of first and second engagement arms 82, 84 contact each other.

In the example of FIG. 4, actuator 86 is illustrated as including a shaft 130 operatively connected to the first engagement arm 82 and the second engagement arm 84. Shaft 130 may be threaded and actuator 86 may further include a knob 132 coupled to the shaft. Rotation of knob 132 in one direction may cause first engagement arm 82 to move closer to second engagement arm 84, while rotation of the knob in the opposite direction can cause the first engagement arm to move away from the second engagement arm.

First engagement arm 82 and/or second engagement arm 84 may be directly connected to shaft 130 or may be indirectly connected via one or more intermediate portions. For example, as illustrated, compressor-distractor 80 includes a first bridging arm 134 between actuator 86 and first engagement arm 82, particularly between shaft 130 connected to actuator 86 and first engagement arm 82. Compressor-distractor 80 also includes a second bridging arm 136 between actuator 86 and second engagement arm 84, particularly between shaft 130 connected to actuator 86 and second engagement arm 84. As illustrated, first bridging arm 134 and second bridging arm 136 extend generally orthogonally from a lengthwise extent of first engagement arm 82 and second engagement arm 84, respectively. For example, first bridging arm 134 and second bridging arm 136 may be connected to first engagement arm 82 and second engagement arm 84, respectively, at approximately a midpoint along the length of each engagement arm. This can help allow compressor-distractor 80 to be flipped between orientations and used interchangeably between different orientations.

To secure actuator 86 to compressor-distractor 80, the actuator may be fixedly connected to one of the engagement arms. For example, shaft 130 of actuator 86 may be fixedly attached along its length to first engagement arm 82 and rotatable relative to the second engagement arm 84. As a result, when knob 132 is rotated, second engagement arm 84 may move along the length of shaft 130 towards and/or away from first engagement arm 82. This provides relative movement between the two arms while first engagement arm 82 remains in a fixed position relative to actuator 86.

In some examples, the mechanical advantage provided by actuator 86 can be controlled to help limit peak torque and prevent overtightening (over compression) of the bone portions connected to compressor-distractor 80. The mechanical advantage can be controlled by controlling the geometry of knob 132, the thread lead of shaft 130, and/or drag (e.g., mechanical losses from friction). In some examples, the thread lead of shaft 130 is greater than 1.5 mm per turn, such as greater than 2.0 mm per turn, or greater than 2.5 mm per turn, such as from 2.0 to 3.0 mm per turn. Accordingly, peak torque input from an average user may be less than 30 pounds of force, such as less than 25 pounds of force.

To help stabilize first engagement arm 82 relative to second engagement arm 84 during movement along shaft 130, compressor-distractor 80 may also include one or more unthreaded shafts extending parallel to the threaded shaft. In FIG. 4, for example, actuator 86 has an unthreaded shaft 133 extending parallel to threaded shaft 130 and helps stabilize second engagement arm 84 as it moves along the threaded shaft towards and away from first engagement arm 82.

During actuation of actuator 86, compressor-distractor 80 may have a tendency to move up first pin 98 and/or second pin 100. To help secure compressor-distractor 80 to one or both pins, the compressor-distractor may include one or locking mechanisms. The locking mechanism can interface with a pin engaged with compressor-distractor to lock the compressor-distractor to pin (e.g., at a particular sagittal plane position). In FIG. 4, compressor-distractor 80 is illustrated as including a locking mechanism 135.

Figure 7A:
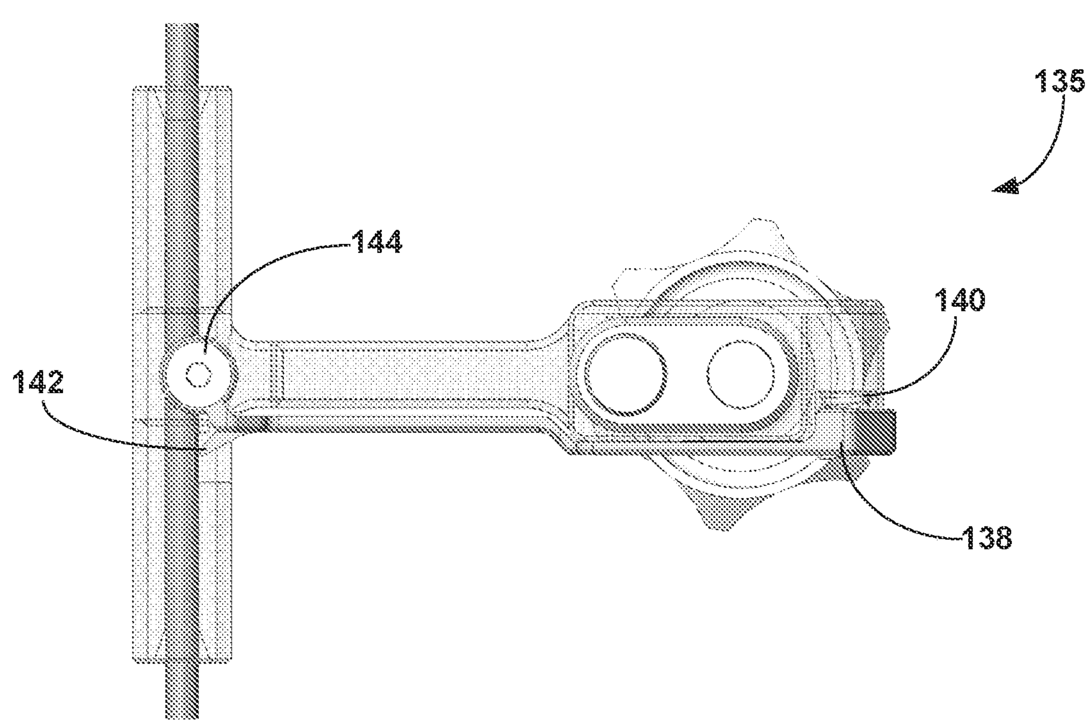
FIGS. 7A and 7B are side sectional illustrations showing an example configuration of a locking mechanism.
Figure 7B:
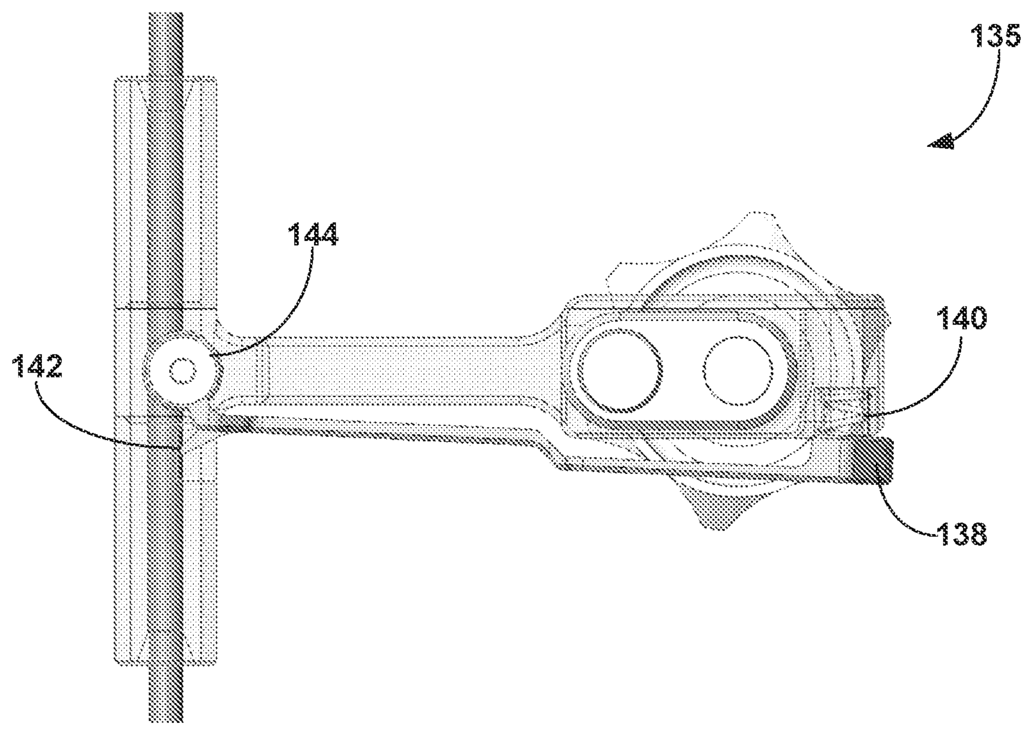

FIGS. 7A and 7B are side sectional illustrations showing an example configuration of locking mechanism 135. FIG. 7A illustrates locking mechanism 135 in an unlocked position. FIG. 7B illustrates locking mechanism 135 in a locked position. In the illustrated example, locking mechanism 135 includes a locking arm 138 operatively connected to a spring 140. Locking arm 138 has a contact end 142 configured to press against first pin 98 or second pin 100. Locking arm 138 can rotate about a pivot connection 144. A center of rotation of pivot connection 144 may be aligned with an edge of the pin being locked. Contact end 142 of locking arm 138 may provide an orthogonal moment to the pin being locked, e.g., when spring 140 is extended in the locking position. For example, the force applied by contact end 142 may be applied approximately 90 degrees relative to the length of the pin being locked. This can provide bi-directional locking, e.g., resisting relative movement between the pin and contact end 142 independent of whether compressor-distractor 80 is used in the first orientation or the second orientation, which may bias the compressor-distractor along the length of the pin in opposite directions depending on the orientation of the compressor-distractor.

Compressor-distractor 80 may be fabricated from any suitable material or combination of materials, such as metal (e.g., stainless steel) and/or polymeric materials. In some configurations, compressor-distractor 80 is fabricated from a radiolucent material such that it is relatively penetrable by X-rays and other forms of radiation, such as thermoplastics and carbon-fiber materials. Such materials are useful for not obstructing visualization of bones using an imaging device when the bone positioning guide is positioned on bones.

While compressor-distractor 80 has generally been described as having a first engagement arm 82 having first and second side pin-receiving holes angled in one or more planes relative to an orthogonal pin-receiving hole 92 defined by second engagement arm 84 (e.g., to receive second pin 100 extending orthogonally in the dorsal-to-plantar direction), other configurations of pin-receiving holes can be used. In general, relative angles between sets of pin-receiving holes defined by first engagement arm 82 and second engagement arm 84 may be achieved by relatively angling the pin-receiving holes of both arms.

Figure 8A:
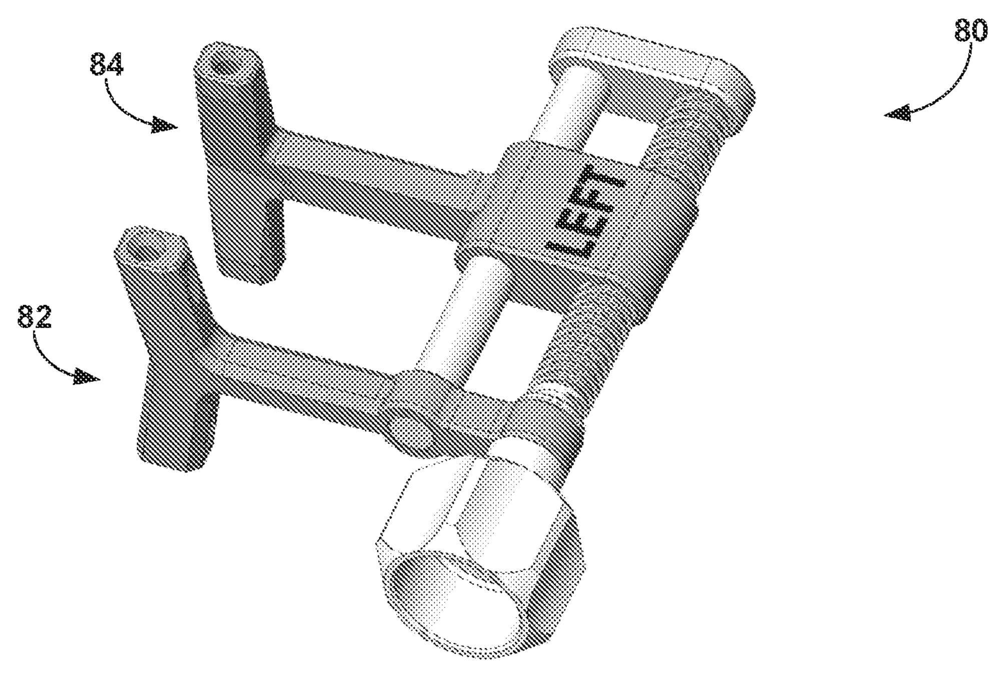
FIGS. 8A and 8B are first and second side views of another example configuration of a reversible compressor-distractor.
Figure 8B:
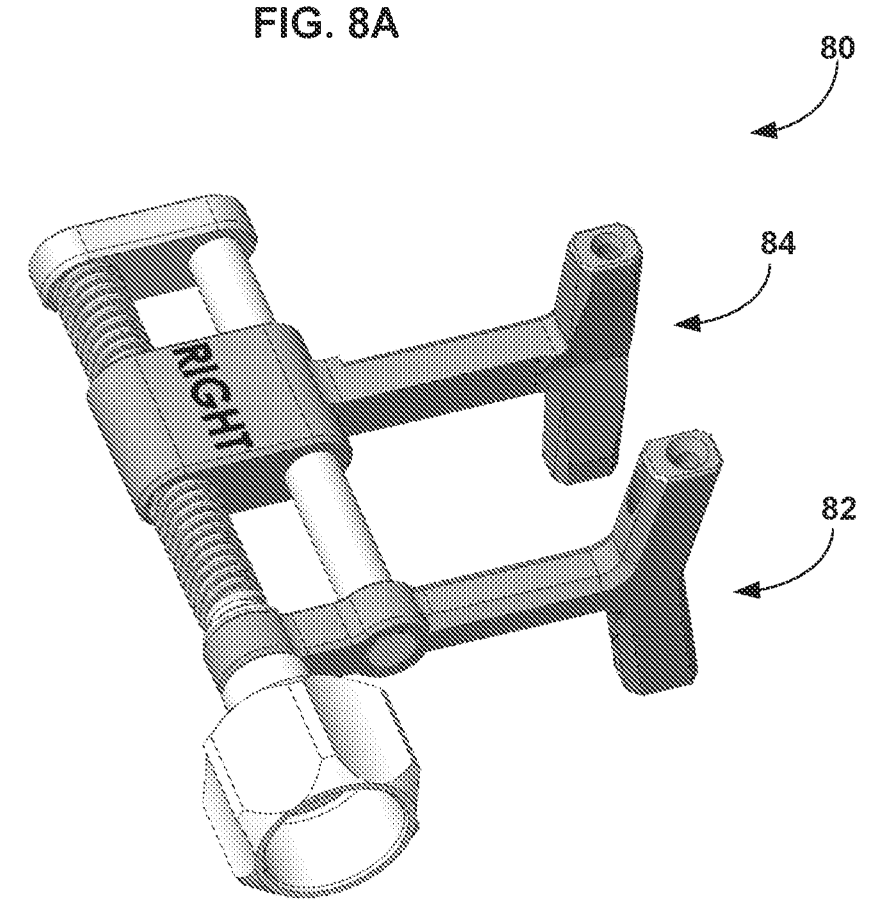

For example, instead of pin-receiving hole 92 of second engagement arm 84 extending through the first and second ends of the second engagement arm, the pin-receiving hole may be angled and extend out through a sidewall of the second engagement arm. When so configured, second engagement arm may also include a first side pin-receiving hole (e.g., optionally with a first pin exit hole through a sidewall of the engagement arm) and a second side pin-receiving hole (e.g., optionally with a second pin exit hole through a sidewall of the engagement arm). FIGS. 8A and 8B are first and second side views of another example configuration of compressor-distractor 80 in which the second engagement arm does not include an orthogonal pin-receiving hole extending through a length of the engagement arm but instead includes off-axis pin-receiving holes.

Figure 9:
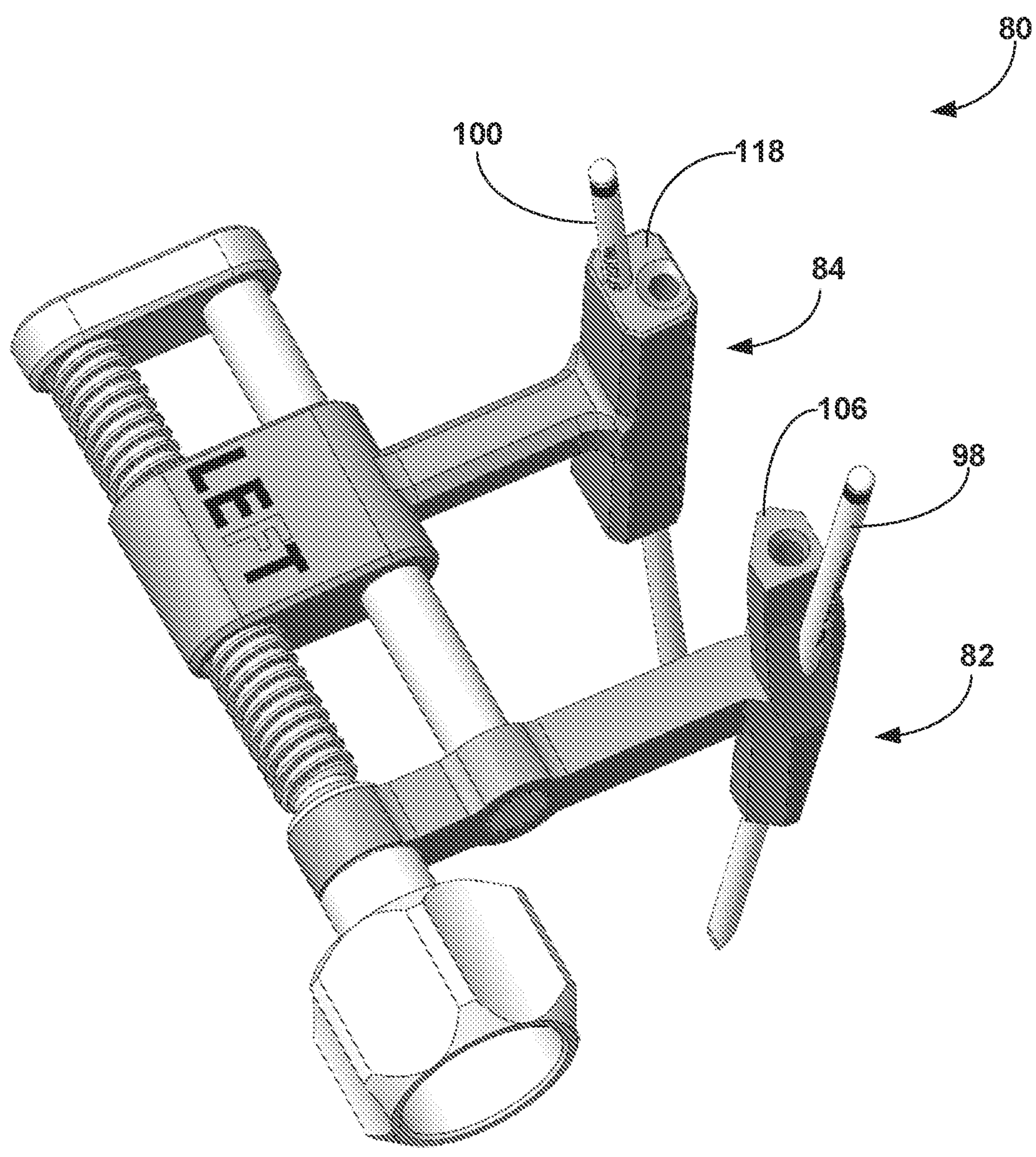
FIG. 9 is a perspective view of another example configuration of a reversible compressor-distractor.

In addition, while compressor-distractor 80 has generally been described as having a first engagement arm 82 having first and second side pin-receiving holes with pin exit locations extending through a sidewall of the engagement arm, in other configurations, one or both of the first and second side pin-receiving holes may have a pin entrance on one end of the engagement arm and a pin exit on another end of the engagement arm. This may position the pin entrance for a pin-receiving hole to be used in one orientation of compressor-distractor 80 adjacent to the pin exit for a pin-receiving hole to be used in a second orientation of the compressor-distractor. FIG. 9 is a perspective view of another example configuration of compressor-distractor 80 in which the first and second side pin-receiving holes have an adjacent pin entrance and pin exit through an end of the engagement arm.

A compressor-distractor according to the disclosure may be used as part of a surgical procedure in which at least two pins are inserted into different bones or different portions of the same bone. The at least two pins may be inserted in generally parallel alignment and/or the pins may be realigned during the surgical procedure so as to be substantially parallel (e.g., prior to installation of compressor-distractor 80). The two pins may be substantially parallel in that the pins are positioned side-by-side and have substantially the same distance continuously between the two pins in each of the three planes (e.g., the distance varies by less than 10%, such as less than 5% across the lengths of the pins in any given plane, with different continuous distances in different planes). Compressor-distractor 80 can be inserted over the parallel pins by threading the parallel pins into the pin-receiving holes of the device, thereby causing the pins to move from a substantially parallel alignment to an angled alignment dictated by the angulation of the pin-receiving holes. Compressor-distractor 80 may then be used to distract the bone portions into which the pins are inserted (e.g., by actuating actuator 86 to draw the bone portions away from each other) and/or compress the bone portions into which the pins are inserted (e.g., by actuating actuator 86 to move the bone portions towards each other).

In some examples, compressor-distractor 80 is used as part of a metatarsal realignment procedure in which a metatarsal is realigned relative to an adjacent cuneiform and/or metatarsal in one or more planes, such as two or three planes. Additional details on example bone realignment techniques and devices with which compressor-distractor 80 may be used are described in U.S. Pat. No. 9,622,805, titled "BONE POSITIONING AND PREPARING GUIDE SYSTEMS AND METHODS," filed on Dec. 28, 2015 and issued Apr. 18, 2017, and U.S. Pat. No. 9,936,994, titled "BONE POSITIONING GUIDE," filed on Jul. 14, 2016 and issued on Apr. 10, 2018; US Patent Publication No. 2017/0042599 titled "TARSAL-METATARSAL JOINT PROCEDURE UTILIZING FULCRUM," filed on Aug. 14, 2016; and U.S. Provisional Patent Application No. 63/406,486 titled "MINIMALLY INVASIVE METATARSAL REALIGNMENT," filed concurrently herewith. The entire contents of each of these documents are hereby incorporated by reference.

The pins over which compressor-distractor 80 is installed may be used to pin and/or guide another medical instrument used during the surgical technique. For example first and second pins 98, 100 may be used to pin a first medical instrument to the bones or bone portions being operated upon. The medical instrument can be removed over the parallel pins, leaving the pins inserted into the bone or bone portions, and compressor-distractor 80 subsequently placed over the pins.

For example, in the case of a metatarsal realignment procedure, first and second pins 98, 100 may be used to pin a bone preparation guide to a foot being operated upon. The bone preparation guide can be used to prepare an end face of a metatarsal and an adjacent end face of a corresponding cuneiform. The bone preparation guide can be taken off the first and second pins and compressor-distractor 80 installed on the pins.

For example, the clinician can select one of two different available orientations in which to use compressor-distractor 80 (e.g., with the first side positioned plantarly or the second side positioned plantarly). The clinician can select the desired orientation by flipping the compressor-distractor (e.g., 180 degrees about the length of the device) from the first one of the two different available orientations to the second one of the two different available orientations. One orientation may correspond to a procedure performed on a right foot of the patient while the other orientation may correspond to a procedure performed on a left foot of the patient.

With the desired orientation of compressor-distractor 80 selected, the clinician can insert the compressor-distractor on the first and second pins 98, 100 by aligning pin entrances associated with the selected orientation of the compressor-distractor with the ends of the pins inserted into bones. The clinician can advance compressor-distractor 80 down on the pins, e.g., until the ends of the pins project out of corresponding pin exits. In some examples, the clinician advance compressor-distractor 80 down on the pins until the ends of the first and send engagement arms contact underlying skin and/or bone. The relatively large, substantially planar end faces of the engagement arms may minimize soft tissue damage when the first and second pins 98, 100 are inserted percutaneously and the ends of the engagement arms contact underlying skin. In either case, the relative angulation of the pin-receiving holes defined by the arms may cause the first and second pins 98, 100 (and, correspondingly, bone portions in which the pins are inserted) to move relative to each other. With compressor-distractor 80 positioned on first and second pins 98, 100, the compressor-distractor can be manipulated to open the joint space between the metatarsal and cuneiform, e.g., to facilitate joint cleanup, and/or manipulated to compress the two bones together for fixation.

Figure 10:
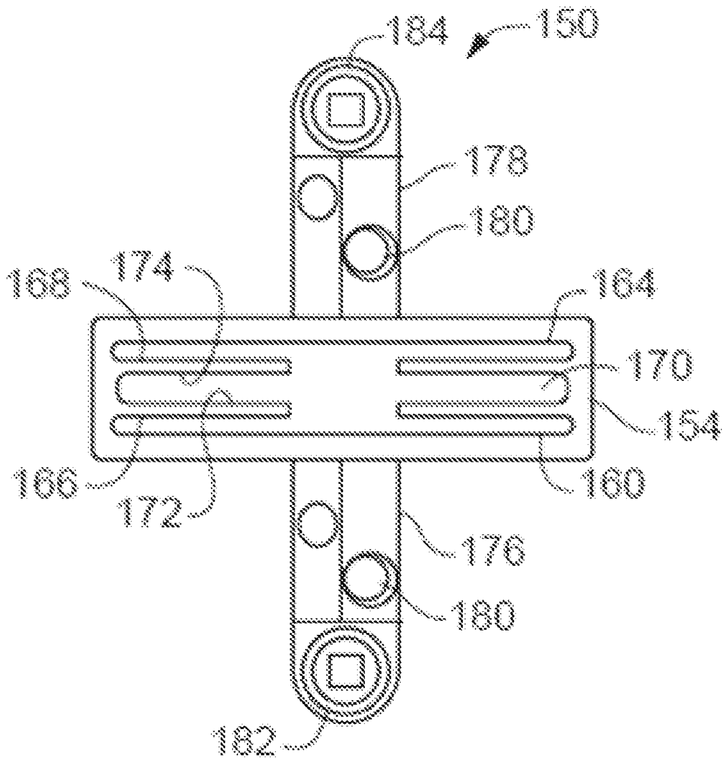
FIG. 10 is a top plan view of an example bone preparation guide that can be used with a compressor-distractor.

FIG. 10 illustrates an example bone preparation guide 150 that may be used as part of a surgical procedure involving compressor-distractor 80. In some examples, bone preparation guide 150 includes a body 154 defining a first guide surface 160 to define a first preparing plane and a second guide surface 164 to define a second preparing plane. A tissue removing instrument (e.g., a saw, rotary bur, osteotome, etc., not shown) can be aligned with the surfaces to remove tissue (e.g., remove cartilage or bone and/or make cuts to bone). The first and second guide surfaces 160, 164 can be spaced from each other by a distance, (e.g., between about 2 millimeters and about 10 millimeters, such as between about 4 and about 7 millimeters). In the embodiment shown, the first and second guide surfaces are parallel, such that cuts to adjacent bones using the guide surfaces will be generally parallel.

In some configurations, as shown in FIG. 10, a first facing surface 166 is positioned adjacent the first guide surface 160 and/or a second facing surface 168 is positioned adjacent the second guide surface 164. In such configurations, the distance between the first guide surface and the first facing surface defines a first guide slot, and the distance between the second guide surface and the second facing surface defines a second guide slot. Each slot can be sized to receive a tissue removing instrument to prepare the bone ends. The first and second slots may be parallel or skewed. In the illustrated example, the facing surfaces each contain a gap, such that the surface is not a single, continuous surface. In other embodiments, the facing surfaces can be a single, continuous surface lacking any such gap.

An opening 170 can be defined by the body 154 between the first and second guide surfaces. The opening can be an area between the guide surfaces useful for allowing a practitioner to have a visual path to bones during bone preparation and/or to receive instruments. In the configuration shown, the opening extends across the body and a distance from a surface 172 opposite of the first facing surface 166 to a surface 174 opposite of the second facing surface 168.

The illustrated bone preparation guide also includes a first end 176 extending from the body 154 in a first direction and a second end 178 extending from the body in a second direction. The second direction can be different than the first direction (e.g., an opposite direction). As shown, each of the first end and the second end can include at least one fixation aperture 180 configured to receive a fixation pin to secure the bone preparation guide to an underlying bone. For example, first end 176 of bone preparation guide 150 may define a first fixation aperture through which first pin 98 (FIG. 5) is inserted and the second end 178 of bone preparation guide 150 may define a second fixation aperture through which second pin 100 (FIG. 5) is inserted. These two fixation apertures may or may not be parallel aligned, such that first and second pins 98, 100 extend through the holes parallel to each other. The first end 176 and/or the second end 178 of bone preparation guide 150 may also defined one or more additional fixation apertures that are angled (at a non-zero degree angle) or otherwise skewed relative to the two parallel fixation apertures.

In use, a clinician may insert the two pins (e.g., parallel pins) through fixation apertures 180 and may optionally insert one or more angled pins through the one or more angled fixation apertures. This combination of parallel and angled pins may prevent bone preparation guide 150 from being removed from the underlying bones being worked upon. When the clinician has completed using the bone preparation guide, the angled pin or pins may be removed leaving the two parallel pins inserted into the underlying bones. Bone preparation guide 150 can be slid or otherwise moved up and off the parallel pins and compressor-distractor 80 thereafter inserted down over the pins.

In some examples as shown in FIG. 10, bone preparation guide 150 can also include a first adjustable stabilization member 182 engaged with the first end 176 and/or a second adjustable stabilization member 184 engaged with the second end 178. Each of the members can be threaded and engage a threaded aperture defined by the ends. The elevation of each end can be adjusted with respect to a bone by adjusting the stabilization member. In some embodiments, as shown, the stabilization members are cannulated such that they can receive a fixation pin.

Figure 11:
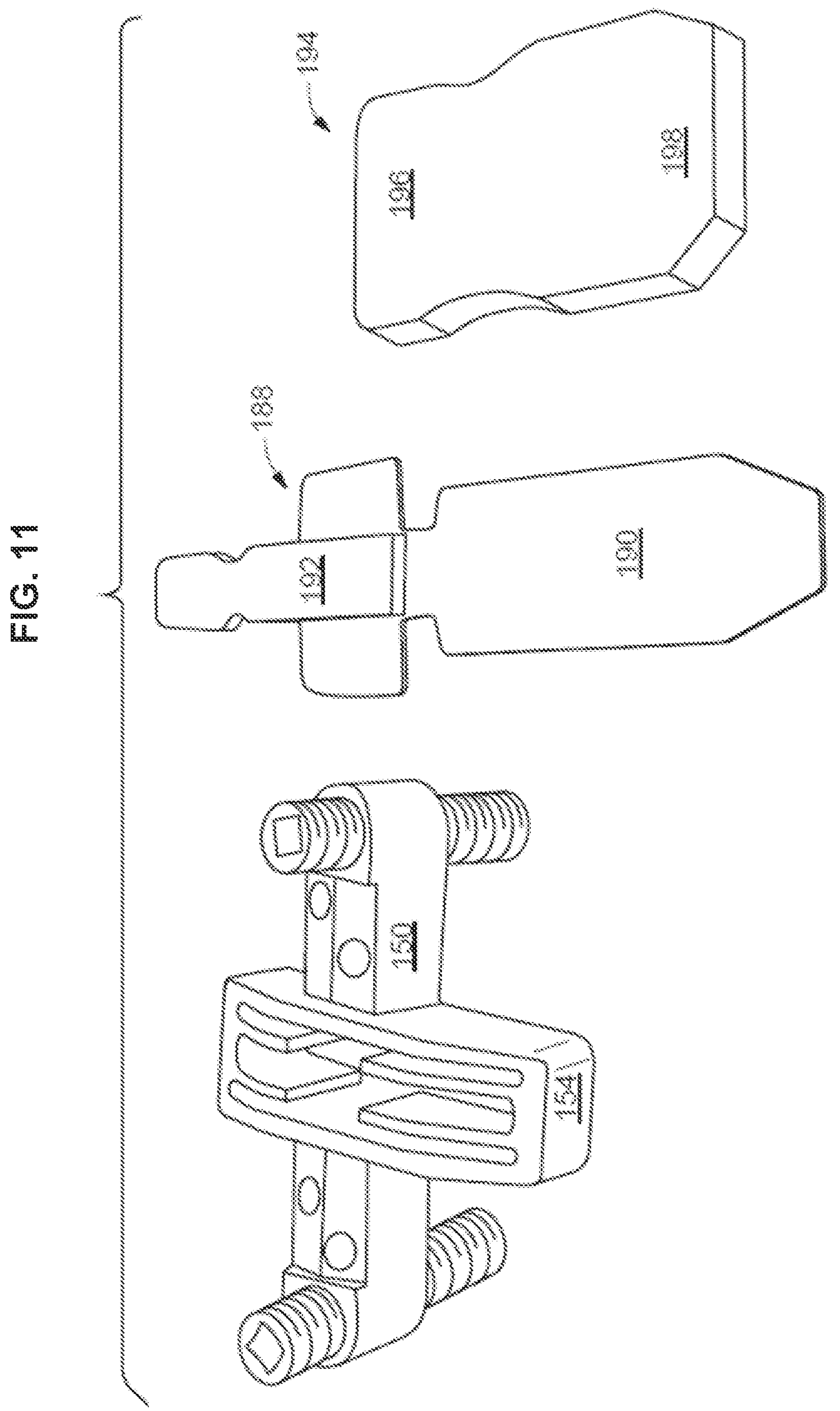
FIG. 11 is a perspective view of an example bone preparation guide, spacer, and tissue removing instrument check member that can be used with a compressor-distractor.

With reference to FIG. 11, bone preparation guide 150 may include or be used with a spacer 188 that extends downward from the body 154. Spacer 188 may be configured to be placed into a joint (e.g., within the TMT joint). In some embodiments, the spacer 188 is selectively engageable with the body of the bone preparation guide and removable therefrom. The spacer can have a first portion 190 configured to extend into a joint space and a second portion 192 engageable with the body 154. In the embodiment shown, the spacer can be received within opening 170, such that the spacer extends from the body in between the first and second guide surfaces. Such a spacer can be useful for positioning the body at a desired position with respect to a joint and for properly positioning the guide with respect to bones to be cut in more than one plane (e.g., three planes selected from more than one of a frontal plane, a transverse plane, and a sagittal plane). The distance between the spacer and the first guide surface can define a length of tissue removal (e.g., bone or cartilage to be cut) from a first bone, and the distance between the spacer and the second guide surface can define a length of tissue removal (e.g., bone or cartilage to be cut) from a second bone.

As also shown in FIG. 11, bone preparation guide 150 may include or be used with a tissue removal location check member 194. Tissue removal check member 194 may be engageable with the body 154 and configured to extend to a first bone and a second bone. The tissue removal location check member can have a first portion 196 configured to extend into contact with first and second bones and a second portion 198 engageable with the body. In the embodiment shown, the tissue removal check member 194 is configured to extend in the body 154 at both the first and second guiding surfaces. The tissue removal location check member 194 may be useful for allowing a practitioner to see where a tissue removing instrument guided by the surfaces will contact the bone to be prepared.

Bone preparation facilitated by bone preparation guide 150 can be useful, for instance, to facilitate contact between leading edges of adjacent bones, separated by a joint, or different portions of a single bone, separated by a fracture, such as in a bone alignment and/or fusion procedure. A bone may be prepared using one or more bone preparation techniques. In some applications, a bone is prepared by cutting the bone. The bone may be cut transversely to establish a new bone end facing an opposing bone portion. Additionally or alternatively, the bone may be prepared by morselizing an end of the bone. The bone end can be morselized using any suitable tool, such as a rotary bur, osteotome, or drill. The bone end may be morselized by masticating, fenestrating, crushing, pulping, and/or breaking the bone end into smaller bits to facilitate deformable contact with an opposing bone portion.

During a surgical technique utilizing compressor-distractor 80, a bone may be moved from an anatomically misaligned position to an anatomically aligned position with respect to another bone. Further, both the end of the moved bone and the facing end of an adjacent end may be prepared for fixation. In some applications, the end of at least one of the moved bone and/or the other bone is prepared after moving the bone into the aligned position. In other applications, the end of at least one of the moved bone and/or the other bone is prepared before moving the bone into the aligned position.

Movement of one bone relative to another bone can be accomplished using one or more instruments and/or techniques. In some examples, bone movement is accomplished using a bone positioning device that applies a force to one bone at a single location, such that the bone both translates and rotates in response to the force. This may be accomplished, for example, using a bone positioning device that engages and/or applies a force between a bone to be moved (e.g., a metatarsal) and another bone (e.g. an anchoring bone, such as another metatarsal or a cuneiform). In some examples, the bone positioning device includes a bone engagement member, a tip, a mechanism to urge the bone engagement member and the tip towards each other, and an actuator to actuate the mechanism. Additionally or alternatively, bone movement may be accomplished using compressor-distractor 80 by imparting movement to one bone relative to another bone as the compressor-distractor is positioned on the pins, causing the pins to move out of their alignment and resulting in movement of the underlying bones in one plane (e.g., frontal plane, sagittal plane, transverse plane), two or more planes, or all three planes. As yet a further addition or alternative, a clinician may facilitate movement by physically grasping a bone, either through direct contact with the bone or indirectly (e.g., by inserting a K-wire, grasping with a tenaculum, or the like), and moving his hand to move the bone.

An example method for preforming a bone alignment procedure utilizing a compressor-distractor according to the disclosure will now be described with respect to FIGS. 12-19 depicting a foot 200 having a first metatarsal 210, a medial cuneiform 222, and a second metatarsal 212. Unless otherwise indicated, the example steps described can be carried out in any order and need not be performed in the order described.

Figure 12:
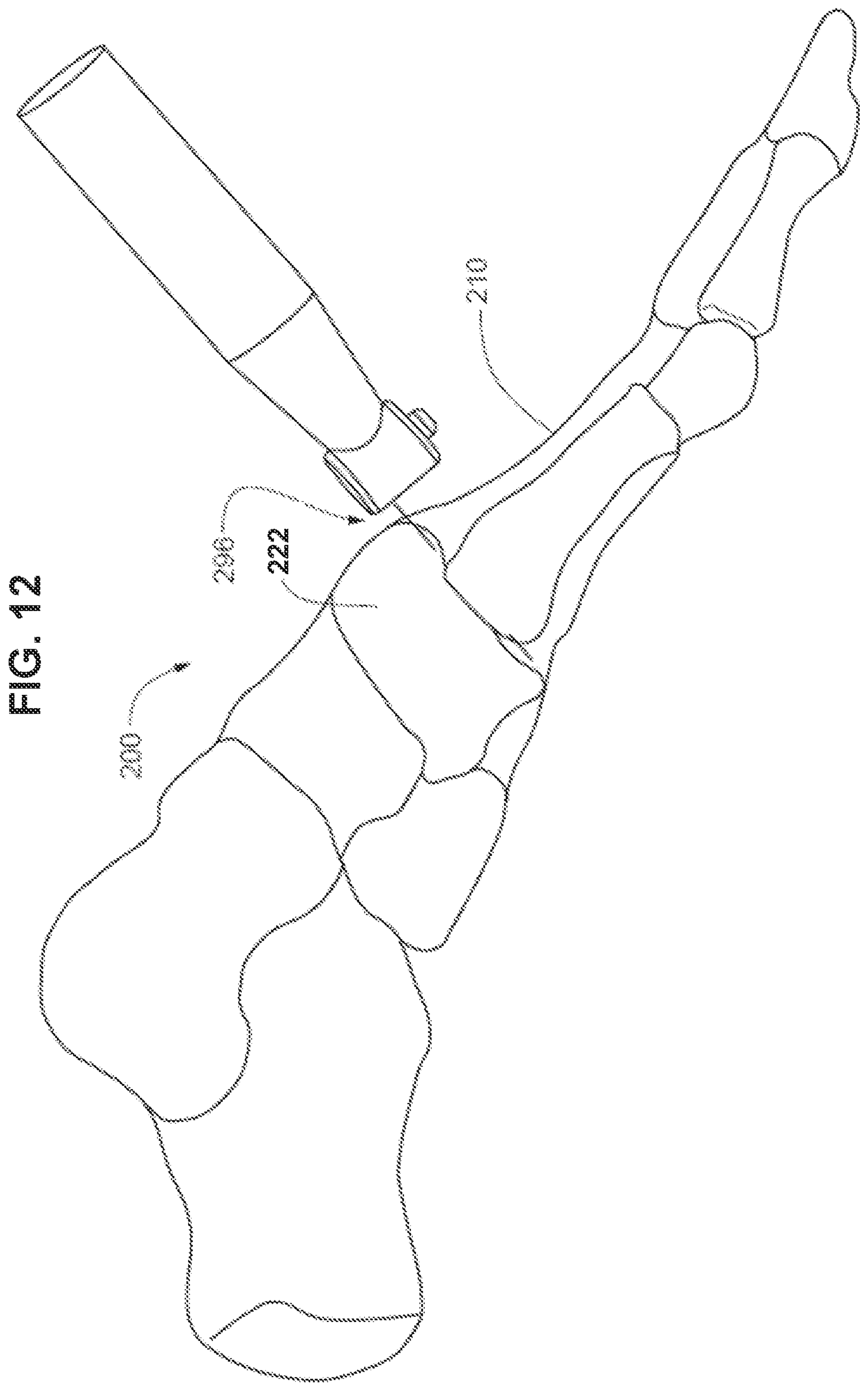
FIG. 12 is a side perspective view of a foot depicting a bone preparation instrument inserted into a joint.
Figure 13:
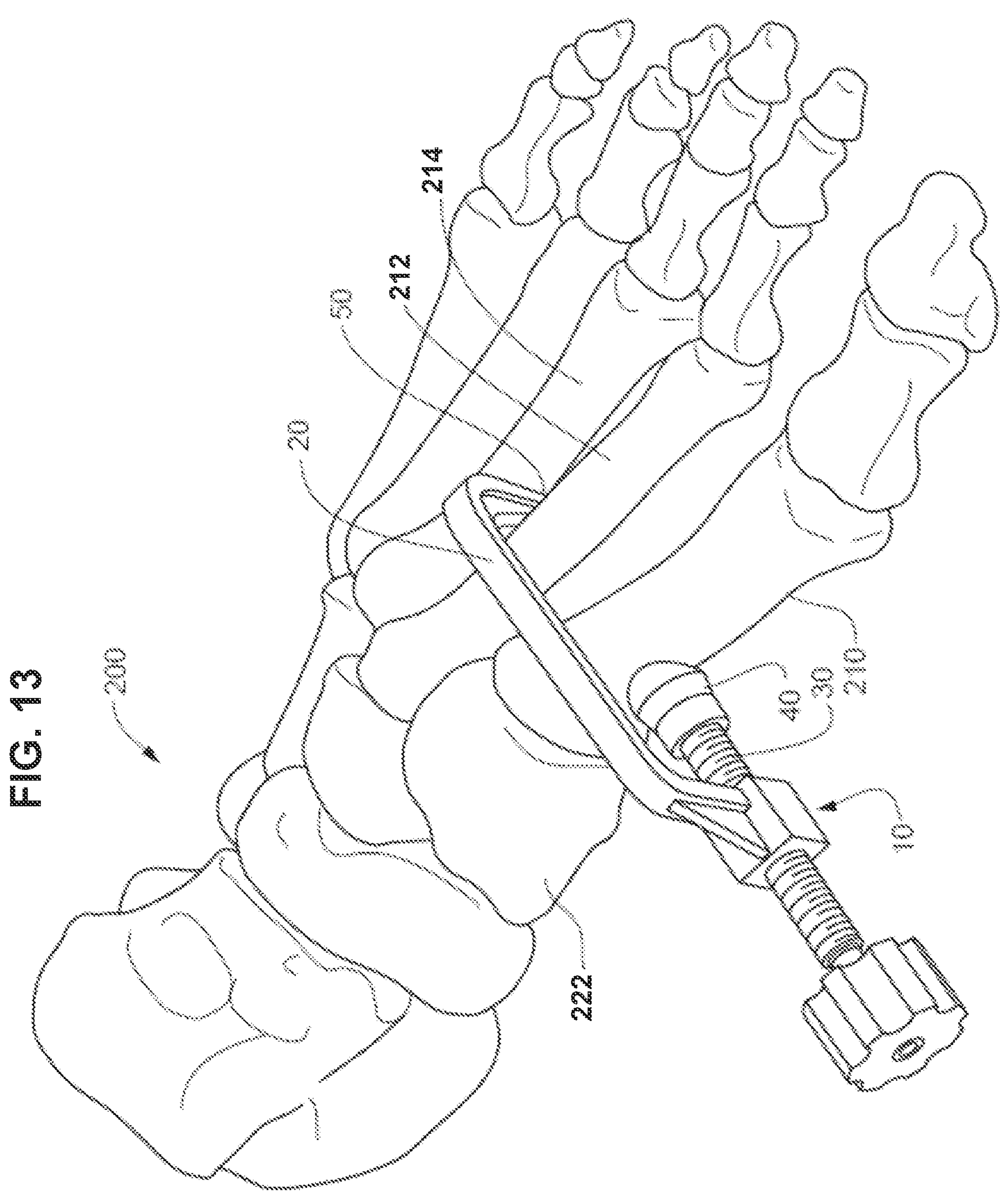
FIG. 13 is a perspective view of a foot depicting a bone positioning guide on the foot prior to an alignment of a first metatarsal.
Figure 14:
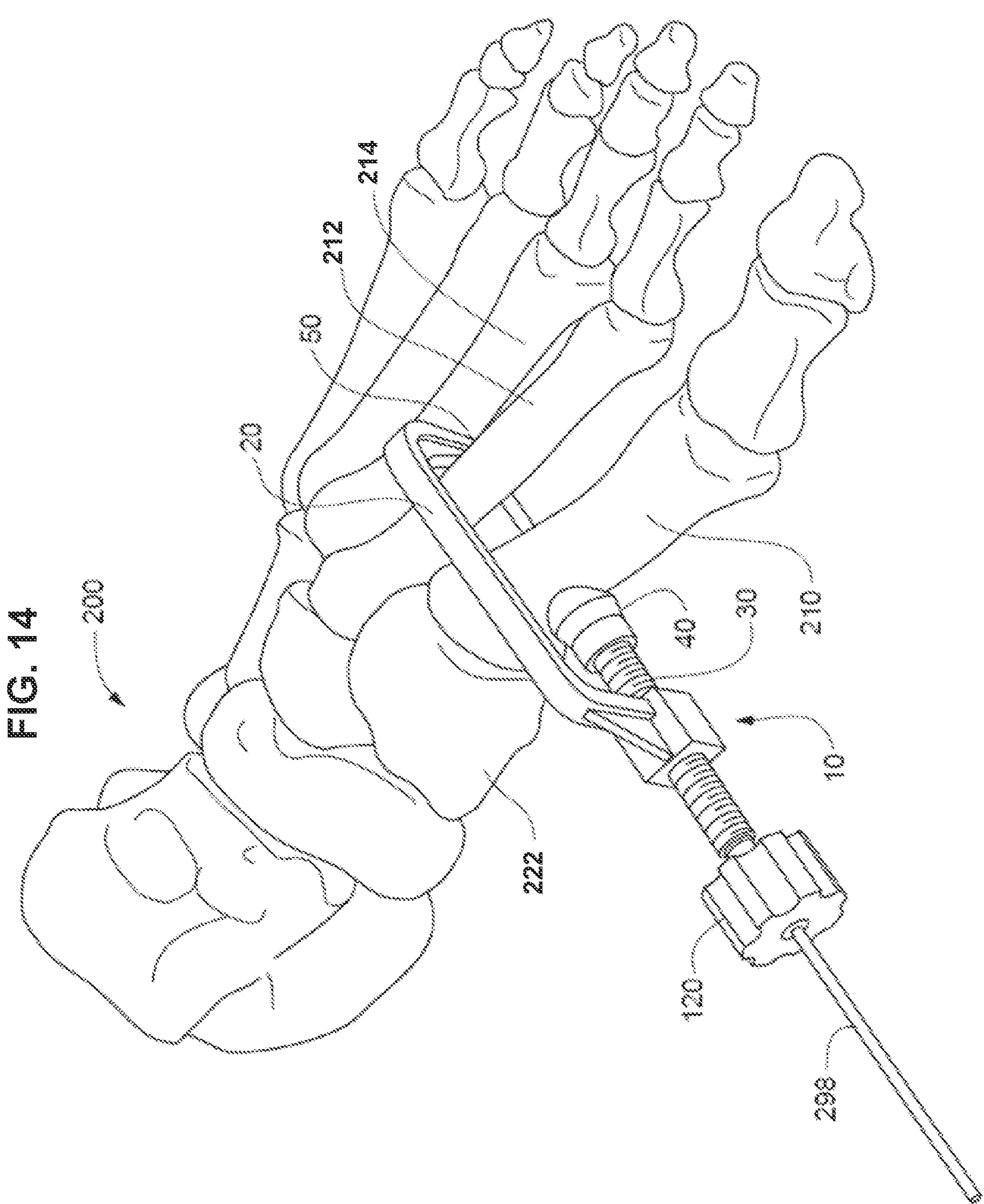
FIG. 14 is a perspective view of a foot depicting a bone positioning guide on the foot after an alignment of a first metatarsal.

After customary surgical preparation and access, a bone preparation instrument 296 can be inserted into the joint (e.g., first tarsal-metatarsal joint) to release soft tissues and/or excise the plantar flare from the base of the first metatarsal 210, as shown in FIG. 12. Excising the plantar flare may involve cutting plantar flare off the first metatarsal 210 so the face of the first metatarsal is generally planar. This step helps to mobilize the joint to facilitate a deformity correction. In some embodiments, the dorsal-lateral flare of the first metatarsal may also be excised to create space for the deformity correction (e.g., with respect to rotation of the first metatarsal). In certain embodiments, a portion of the metatarsal base facing the medial cuneiform can be removed during this mobilizing step.

An incision can be made and, if a bone positioning instrument is going to be used, a tip 50 of a bone positioning guide 10 inserted on the lateral side of a metatarsal other than the first metatarsal 210, such as the second metatarsal 212. As shown in FIG. 10, the tip can be positioned proximally at a base of the second metatarsal 212 and a third metatarsal 214 interface. A surface of a bone engagement member 40 can be placed on the proximal portion of the first metatarsal 210. In some embodiments, the bone engagement member engages a medial ridge of the first metatarsal 210. As shown, the body 20 of the positioning guide can be generally perpendicular to the long axis of the second metatarsal 212.

In applications utilizing bone positioning guide 10, the actuator on the bone positioning guide can be actuated to reduce the angle (transverse plane angle between the first metatarsal and the second metatarsal) and rotate the first metatarsal about its axis (frontal plane axial rotation). The first metatarsal 210 can be properly positioned with respect to the medial cuneiform 222 by moving the bone engagement member 40 bone positioning guide with respect to the tip 50 of the bone positioning guide. In some embodiments, such movement simultaneously pivots the first metatarsal with respect to the cuneiform and rotates the first metatarsal about its longitudinal axis into an anatomically correct position to correct a transverse plane deformity and a frontal plane deformity. Again, however, other applications utilizing compressor-distractor 80 may be performed without utilizing bone positioning guide 10 and/or utilizing a bone positioning guide of different design.

Figure 15:
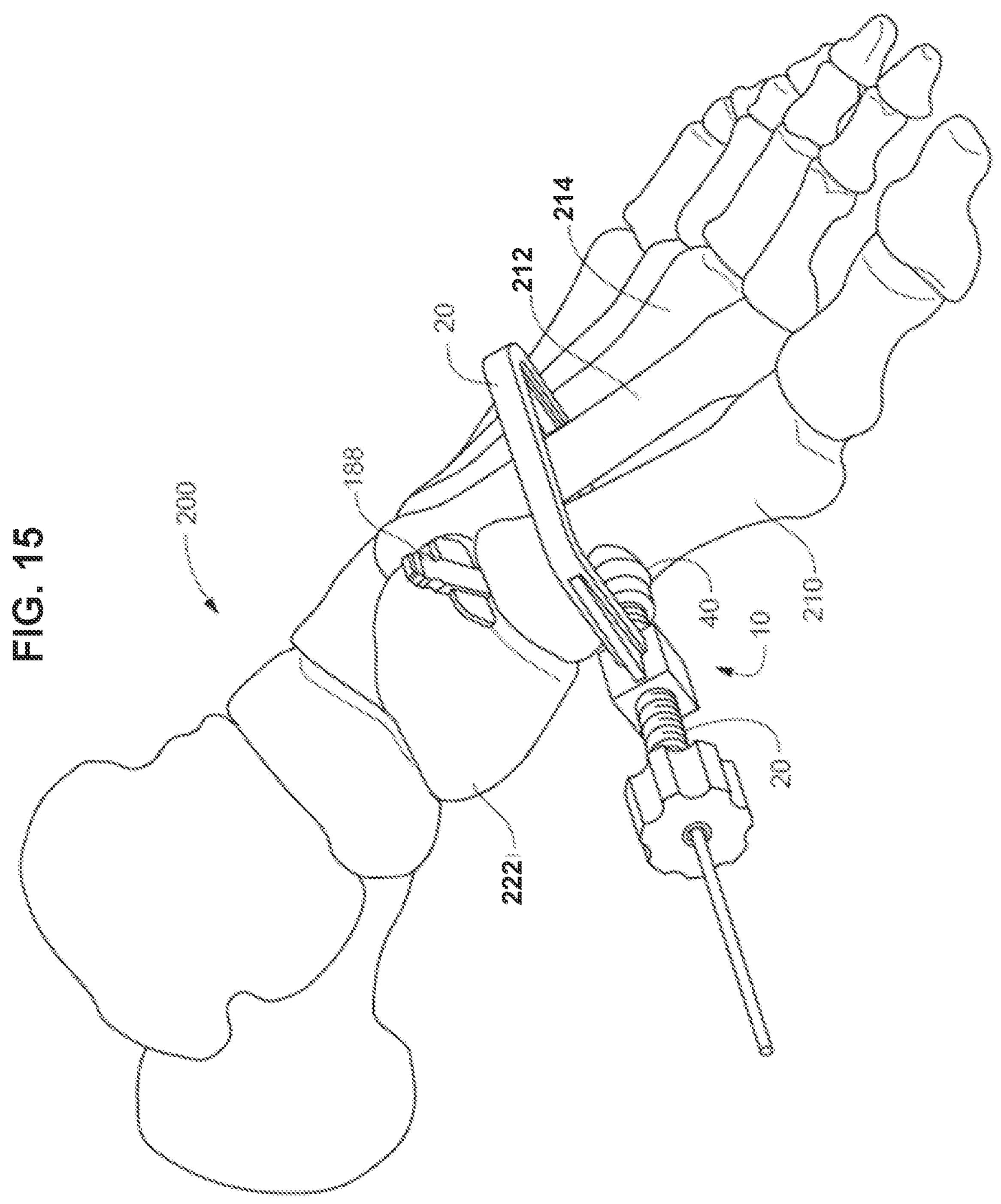
FIG. 15 is a perspective view of a foot depicting a bone positioning guide on the foot after an alignment of a first metatarsal and with a spacer inserted into a joint space.
Figure 16:
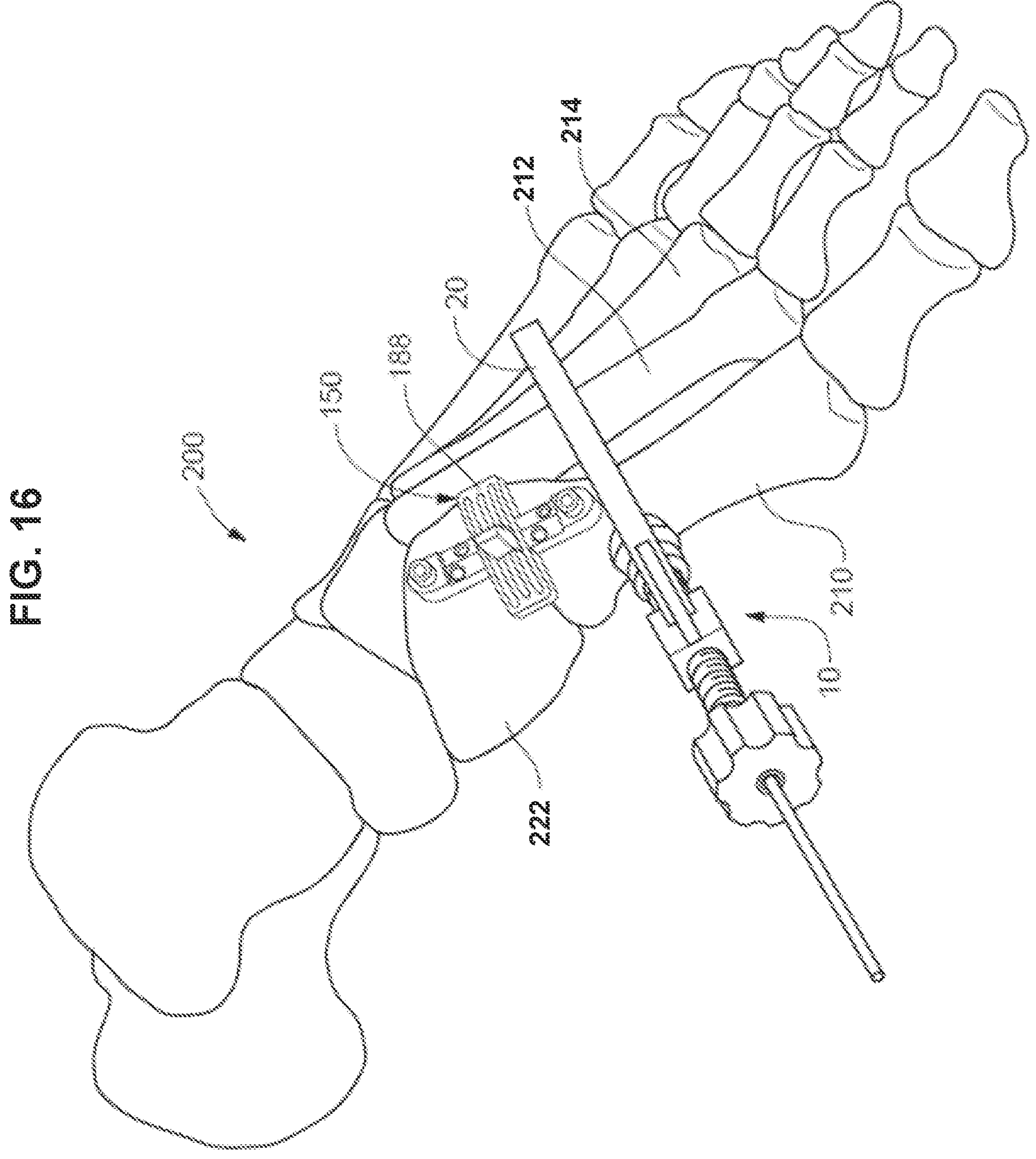
FIG. 16 is a perspective view of a foot depicting a bone preparation guide positioned on the foot.

Independent of whether bone positioning guide 10 is used, an example technique may include positioning joint spacer 188 can be positioned within the joint between the first metatarsal and the medial cuneiform, as illustrated in FIG. 15. Bone preparation guide 150 can be placed over the joint spacer 188 as shown in FIG. 16 and engaged with the joint spacer to set a position and orientation of the bone preparation guide relative to the joint. In other embodiments, bone preparation guide 150 is placed on the bones without using joint spacer 188 to aid with positioning.

Figure 17:
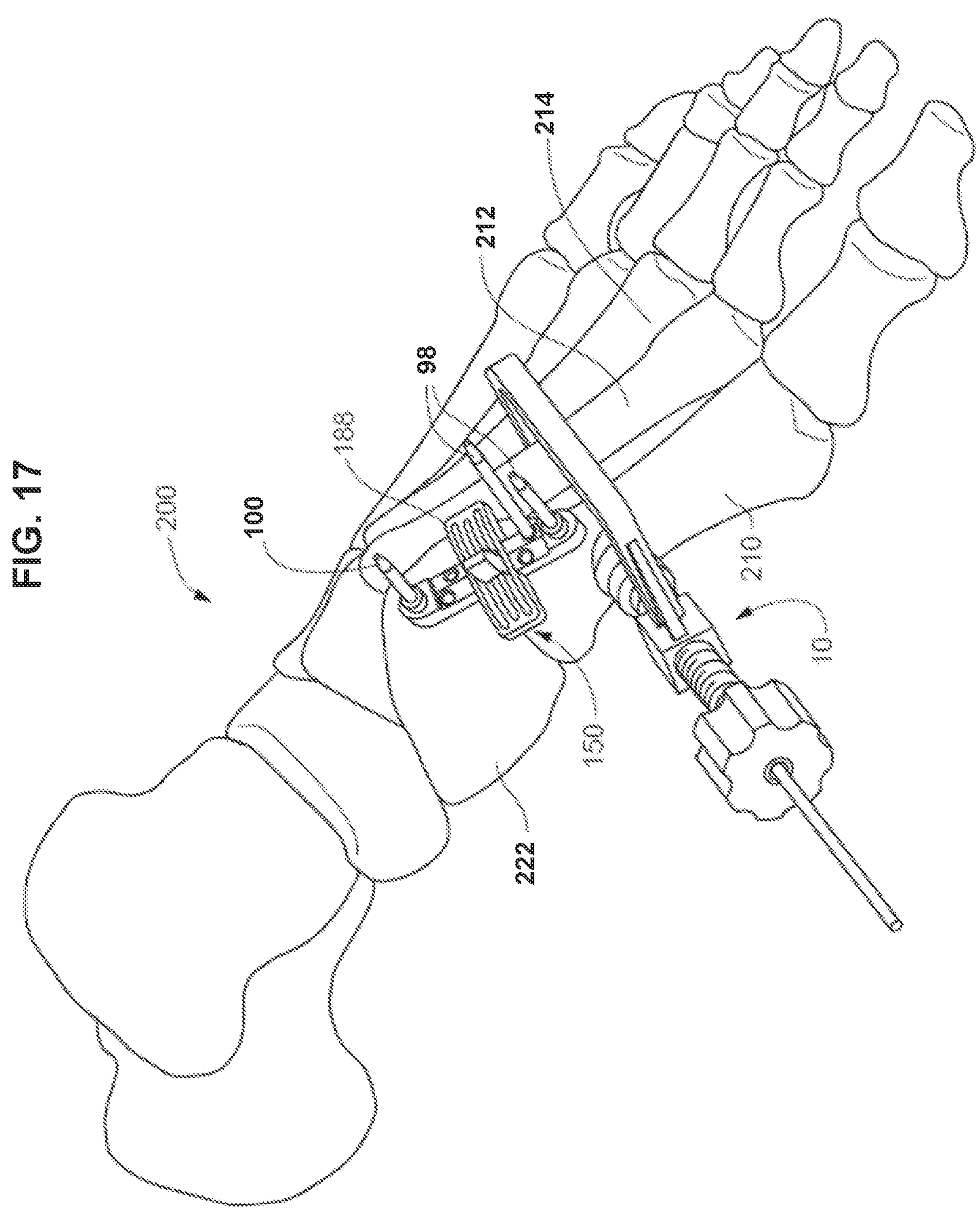
FIG. 17 is a perspective view of a foot depicting a bone preparation guide on the foot with pins inserted through the bone preparation guide.

As depicted in FIG. 17, one or more fixation pins can be inserted into apertures of the bone preparation guide 150 to secure the guide to the first metatarsal 210 and the medial cuneiform 222. The fixation pins inserted into the apertures of bone preparation guide 150 includes a first fixation pin 98 and second fixation pin 100. The first and second fixation pins 98, 100 may be inserted in substantially parallel alignment. The first and second fixation pins 98, 100 may project at least 25 mm above the surface of the bones into which the pins are inserted, such as at least 50 mm, or at least 75 mm. One or more additional pins can be inserted at an angle or in a converging orientation to help prevent movement of the bone preparation guide 150 during a tissue removing step. After insertion of the pins, the spacer 188 (if used) can optionally be removed in embodiments having a selectively engageable spacer.

In some applications, the end of the first metatarsal 210 facing the medial cuneiform 222 can be prepared with a tissue removing instrument 296 guided by a guide surface of bone preparation guide 150 (e.g., inserted through a slot defined by a first guide surface and a first facing surface). In some embodiments, the first metatarsal 210 end preparation is done after at least partially aligning the bones, e.g., by actuating bone positioning guide 10 before preparing the end of first metatarsal 210. In other embodiments, the first metatarsal 210 end preparation is done before the alignment of the bones, e.g., by preparing the end of the first metatarsal 210 before installing compressor-distractor 80 to cause realignment.

In addition to preparing the end of first metatarsal 210, the end of the medial cuneiform 222 facing the first metatarsal 210 can be prepared with the tissue removing instrument 296 guided by a guide surface of bone preparation guide 150 (e.g., inserted through a slot defined by a second guide surface and a second facing surface). In some embodiments, the medial cuneiform 222 end preparation is done after the alignment of the bones. In yet other embodiments, the medial cuneiform 222 end preparation is done before the alignment of the bones. In embodiments that include cutting bone or cartilage, the cuneiform cut and the metatarsal cut can be parallel, conforming cuts. In some examples, a saw blade can be inserted through a first slot to cut a portion of the medial cuneiform and the saw blade can be inserted through a second slot to cut a portion of the first metatarsal.

Figure 18:
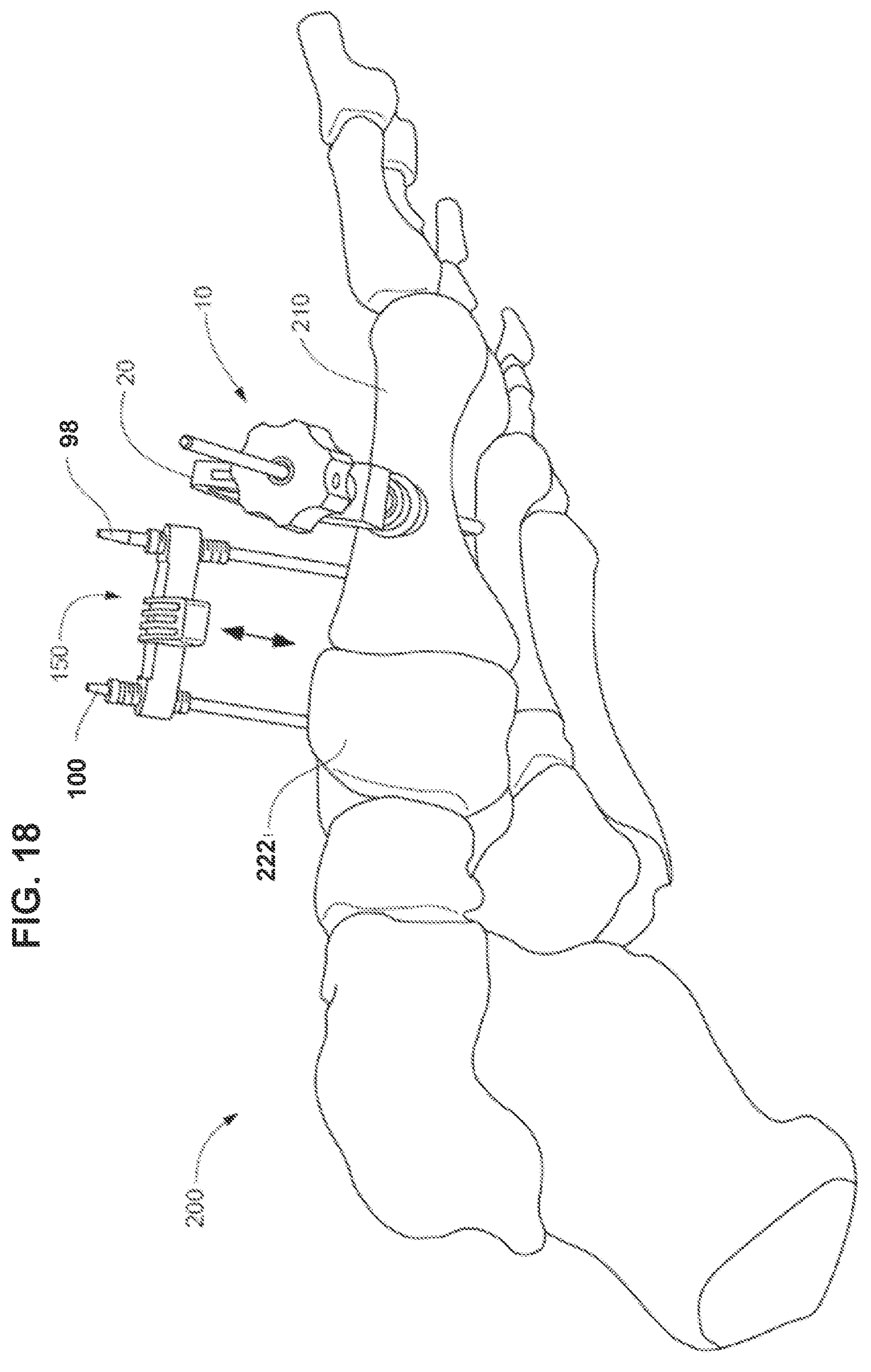
FIG. 18 is a perspective view of a foot depicting a removal of a bone preparation guide.

Any angled/converging pins can be removed and the bone preparation guide 150 can be lifted off the first and second pins 98, 100, as shown in FIG. 18. These pins, which may or may not be substantially parallel pins, can receive compressor-distractor 80. For example, the clinician can align entrance locations of selected pin-receiving holes with the pins and then slide compressor-distractor 80 down over the pins toward the underlying bones and/or skin covering the bones. The clinician may adjust the spacing between first engagement arm 82 and second engagement arm 84 by actuating actuator 86 until the separation distance corresponds to the spacing between first and second pins 98, 100, before installing the compressor-distractor down over the pins. In the process of inserting compressor-distractor 80 on the pins, the angulation between the pin-receiving holes can cause first and second pins 98, 100 to shift to an alignment corresponding to the angular position of the pin-receiving holes. As the first and second pins 98, 100 move relative to each other, first metatarsal 210 may move relative to medial cuneiform 222 a direction and distance corresponding to the movement of first pin 98 relative to second pin 100.

In applications where bone positioning guide 10 is utilized, the bone positioning guide may be removed before or after bone preparation guide 150 is removed and compressor-distractor 80 is installed. In either case, in some examples, a temporary fixation device such as an olive pin, k-wire, or other fixation structure may be used to maintain the position of the underlying bones (e.g., first metatarsal 210 relative to medial cuneiform 222) while bone preparation guide 150 is removed and compressor-distractor 80 is installed.

With compressor-distractor 80 pinned to underlying bones (e.g., first metatarsal 210 and medial cuneiform 222), actuator 86 may be actuated to distract the underlying bones. For example, the clinician may turn knob 132 to cause second engagement arm 84 to move away from first engagement arm 82, opening or enlarging a gap between the underlying bones. When pinned to first metatarsal 210 and medial cuneiform 222, the clinician can actuate actuator 86 to open the TMT joint.

With the underlying bones distracted, the clinician may clean or otherwise prepare the space between the bones and/or the end face of one or both bones. The clinician may clean the space by removing excess cartilage, bone, and/or other cellular debris that may natively exist or may have been created during the bone preparation step that may inhibit infusion.

Figure 19:
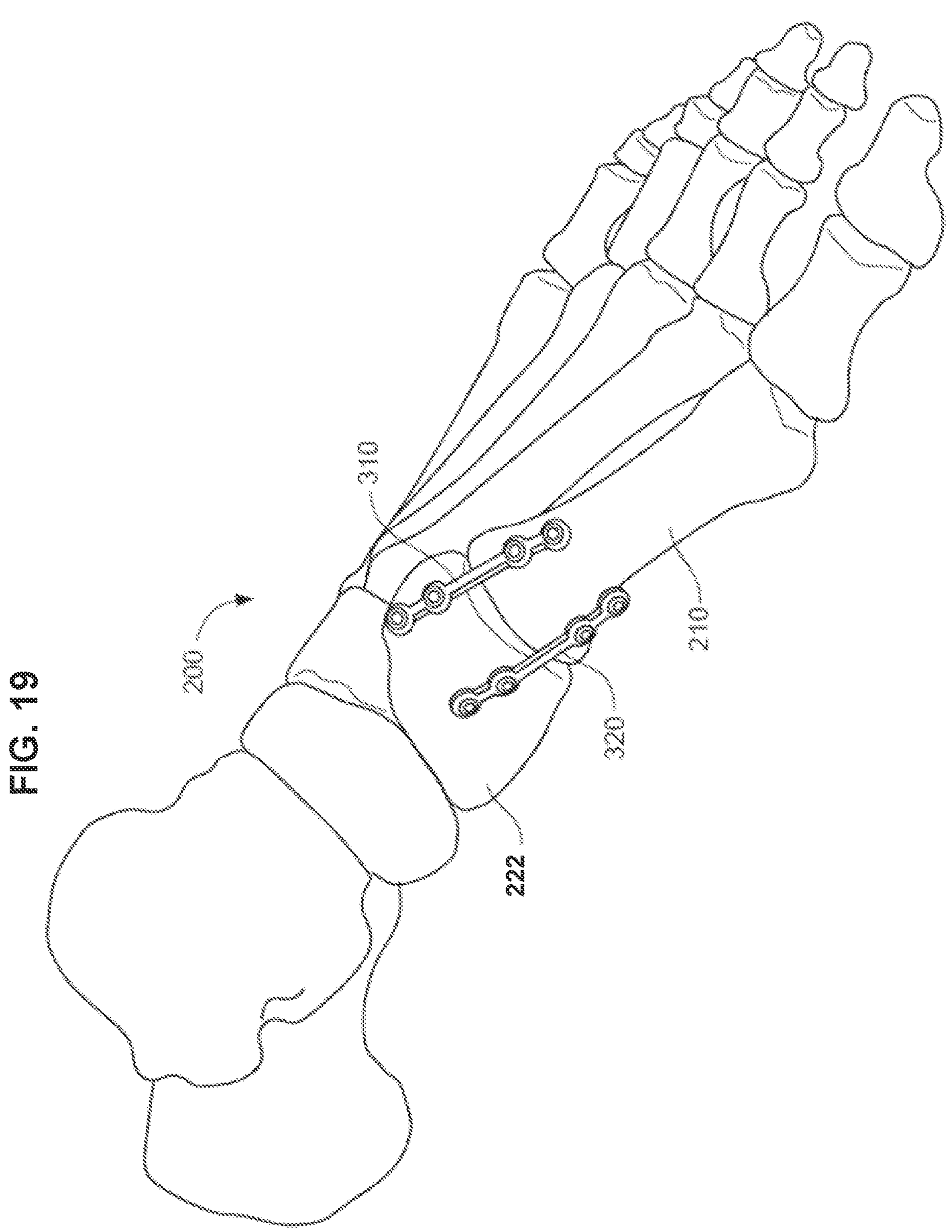
FIG. 19 is a side perspective view of a foot depicting bone plates across a joint between first and second bones.

Independent of whether the clinician utilizes compressor-distractor 80 to distract the underlying bones for cleaning, the clinician may actuate actuator 86 to compress the bones together for permanent fixation infusion. The clinician may turn knob 132 to cause second engagement arm 84 to move toward first engagement arm 82, for example until the end faces of the underlying bones contact each other and/or a compressive force is applied through pins 98, 100 to the end faces. With the two end faces pressed together via compressor-distractor 80, the clinician may provisionally or permanently fixate the bones or bones portions together. For example, one or more bone fixation devices can be applied across the joint and to the two bones to stabilize the joint for fusion, such as two bone plates positioned in different planes. FIG. 19 illustrates an example fixation device arrangement that includes a first bone plate 310 positioned on a dorsal-medial side of the first metatarsal and medial cuneiform and a second bone plate 320 positioned on a medial-plantar side of the first metatarsal and the medial cuneiform. In other embodiments, one or more staples or other implants can be used in addition to or in lieu of a plate.

Compressor-distractor devices and techniques have been described. In some examples, a compressor-distractor according to disclosure is included in a disposable, sterile kit that includes associated surgical instrumentation, such as bone positioning guide and/or a preparation guide described herein. Other components that may be included within the sterile kit include bone fixation devices, bone fixation screws, pins for insertion into pin-receiving holes, and the like.

Various examples have been described. These and other examples are within the scope of the following claims.

The invention claimed is:

1. A reversible compressor-distractor comprising:

(a) a first engagement arm comprising:

(i) a first side pin-receiving hole for receiving a first pin inserted into a first bone portion, the first side pin-receiving hole extending from a first pin entry opening to a first pin exit opening; and (ii) a second side pin-receiving hole for receiving the first pin inserted into the first bone portion, wherein the second side pin-receiving hole is on an opposite lengthwise side of the first engagement arm than the first side pin-receiving hole, and the second side pin-receiving hole extends from a second pin entry opening to a second pin exit opening;

(b) a second engagement arm comprising a pin-receiving hole for receiving a second pin inserted into a second bone portion; and (c) an actuator operatively coupled to the first engagement arm and the second engagement arm, the actuator being configured to move the first engagement arm and the second engagement arm each other to move the first bone portion toward the second bone portion.

2. The reversible compressor-distractor of claim 1, wherein:

the first engagement arm has a length extending from a first end to a second end;

the first side pin-receiving hole extends through the first end of the first engagement arm; and the second side pin-receiving hole extends through the second end of the first engagement arm.

3. The reversible compressor-distractor of claim 2, wherein:

the first engagement arm has a sidewall;

the first side pin-receiving hole extends from the first end of the first engagement arm through the sidewall at a first location; and the second side pin-receiving hole extends from the second end of the first engagement arm through the sidewall at a second location.

4. The reversible compressor-distractor of claim 3, wherein the first location is offset along the length of the first engagement arm from the second location.

5. The reversible compressor-distractor of claim 3, wherein:

the first side pin-receiving hole defines the first pin entry opening at the first location of the sidewall and the first pin exit opening at the first end of the first engagement arm; and the second side pin-receiving hole defines the second pin entry opening at the second location of the sidewall and the second pin exit opening at the second end of the first engagement arm.

6. The reversible compressor-distractor of claim 2, wherein a longitudinal axis defined by the first side pin-receiving hole intersects a longitudinal axis defined by the second side pin-receiving hole at a location between the first end and the second end of the first engagement arm.

7. The reversible compressor-distractor of claim 1, wherein the reversible compressor-distractor is configured to be flipped from a first orientation in which a first end is positioned closer to the first bone portion than a second end and the first pin is inserted through the first side pin-receiving hole to a second orientation in which the second end is positioned closer to the first bone portion than the first end and the first pin is inserted through the second side pin-receiving hole.

8. The reversible compressor-distractor of claim 1, wherein:

the second engagement arm has a length extending from a first end to a second end; and the pin-receiving hole extends from the first end through the second end of the second engagement arm.

9. The reversible compressor-distractor of claim 1, wherein:

the first side pin-receiving hole defines a first longitudinal axis;

the second side pin-receiving hole defines a second longitudinal axis;

the pin-receiving hole of the second engagement arm defines a third longitudinal axis; and the first longitudinal axis and the second longitudinal axis are each angled relative to the third longitudinal axis.

10. The reversible compressor-distractor of claim 9, wherein an angle between the first longitudinal axis and the third longitudinal axis is equal and opposite to an angle between the second longitudinal axis and the third longitudinal axis.

11. The reversible compressor-distractor of claim 9, wherein:

the first longitudinal axis is angled relative to the third longitudinal axis in one or both of a frontal plane and a sagittal plane; and the second longitudinal axis is angled relative to the third longitudinal axis in one or both of the frontal plane and the sagittal plane.

12. The reversible compressor-distractor of claim 11, wherein the first longitudinal axis and the second longitudinal axis are each angled relative to the third longitudinal axis in the frontal plane at an angle ranging from 2 degrees to 20 degrees.

13. The reversible compressor-distractor of claim 11, wherein the first longitudinal axis and the second longitudinal axis are each angled relative to the third longitudinal axis in the sagittal plane at an angle ranging from 5 degrees to 12 degrees.

14. The reversible compressor-distractor of claim 1, wherein the actuator comprises a threaded shaft operatively connected to the first engagement arm and the second engagement arm and at least one unthreaded shaft extending parallel to the threaded shaft.

15. The reversible compressor-distractor of claim 1, further comprising a first bridging arm between the actuator and the first engagement arm and a second bridging arm between the actuator and the second engagement arm.

16. The reversible compressor-distractor of claim 1, further comprising a locking mechanism configured to lock a position of one or both of the first pin and the second pin, when inserted into the reversible compressor-distractor.

17. The reversible compressor-distractor of claim 16, wherein the locking mechanism comprise a locking arm operatively connected to a spring, and the locking arm has a contact end configured to press against one of the first pin or the second pin.

18. The reversible compressor-distractor of claim 17, wherein the locking arm is configured to apply an orthogonal moment to one of the first pin or the second pin.

* * * * *